United States Patent
Andrews et al.

(10) Patent No.: US 8,012,983 B2
(45) Date of Patent: Sep. 6, 2011

(54) SUBSTITUTED TRIAZOLOPYRAZINES USEFUL FOR THE TREATMENT OF DEGENERATIVE AND INFLAMMATORY DISEASES

(75) Inventors: Martin James Inglis Andrews, Mechelen (BE); Mark Stuart Chambers, Saffron Walden (GB); Hervé Van De Poël, Saffron Walden (GB); Grégory Louis Joseph Bar, Mechelen (BE)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 12/436,219

(22) Filed: May 6, 2009

(65) Prior Publication Data
US 2009/0286798 A1   Nov. 19, 2009

Related U.S. Application Data

(60) Provisional application No. 61/126,833, filed on May 7, 2008, provisional application No. 61/145,827, filed on Jan. 20, 2009.

(51) Int. Cl.
*A61K 31/4965* (2006.01)
(52) U.S. Cl. ............ 514/255.05; 544/349; 544/350; 546/268.1; 548/470; 548/482; 549/505
(58) Field of Classification Search ............ 514/255.05; 544/349, 350; 546/268.1; 548/470, 482; 549/505
See application file for complete search history.

(56) References Cited

U.S. PATENT DOCUMENTS

| | | | |
|---|---|---|---|
| 7,186,832 B2 | 3/2007 | Sun et al. | |
| 2005/0009832 A1 | 1/2005 | Sun et al. | |
| 2008/0090818 A1* | 4/2008 | Andrews et al. ........... | 514/233.2 |

FOREIGN PATENT DOCUMENTS

| WO | 9964582 | 12/1999 |
|---|---|---|
| WO | 02056888 | 7/2002 |
| WO | 2007138072 | 12/2006 |
| WO | 2007131991 | 11/2007 |
| WO | 2008138842 | 11/2008 |
| WO | 2008138843 | 11/2008 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Choy EH, Panayi GS. (2001). N Engl J Med 344: 907-16. "Cytokine pathways and joint inflammation in rheumatoid arthritis."
Firestein GS. (2003). Nature. 423:356-61. "Evolving concepts of rheumatoid arthritis."
Smolen JS, Steiner G. (2003). Nat Rev Drug Discov. 2: 473-88. "Therapeutic strategies for rheumatoid arthritis".
Lee DM, Weinblatt ME (2001). Lancet. 358: 903-11. "Rheumatoid arthritis."
"Kremer J. M. et al. (2003).N Engl J Med. 349:1907-1915. Treatment of rheumatoid arthritis by selective inhibitors of t-cell activation with fusion protein CTLA4lg".
Edwards J. C.W. et al. (2004) N Engl J Med. 350:2572-2581. "Efficacy of B-cell targeted therapy with rituximab in patients with rheumatoid arthritis".
O'Dell Jr et al. (2002) Arthritis Rheum. 46:1164-70. "Treatment of rheumatoid arthritis with methotrexate and hydroxychloroquine methotrexate and sulfasalazine, . . . ".
St Clair EW et al. (2004). Arthritis Rheum. 50 :3432-43. Combination of infliximab and methotrexate therapy for early rheumatoid arthritis: a randomized, controlled trial.
Gomez-Reino JJ, et al. (2003). Arthritis Rheum. 48: 2122-7. "Treatment of rheumatoid arthritis with tumor necrosis factor inhibitors may predispose to significant increase . . . ".
O'Dell Jr. (2004). N Engl J Med. 350(25):2591-602. "Therapeutic strategies for rheumatoid arthritis."
New L, Jiang Y, Han J. (2003) Mol Biol Cell. 14(6):2603-16. "Regulation of PRAK subcellular location by p38 MAP kinases."

(Continued)

*Primary Examiner* — James O Wilson
*Assistant Examiner* — Douglas M Willis
(74) *Attorney, Agent, or Firm* — Klauber & Jackson LLC

(57) ABSTRACT

Novel [1.2.4]triazolo[1,5-a]pyrazine and imidazo[1,2-a] pyrazine compounds are disclosed that have a formula represented by the following:

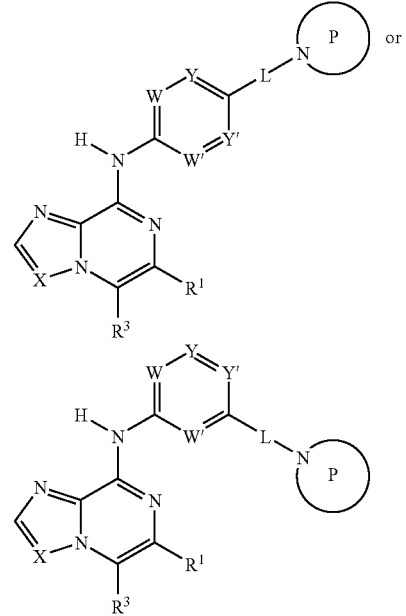

The compounds may be prepared as pharmaceutical compositions, and may be used for the prevention and treatment of a variety of conditions in mammals including humans, including by way of non-limiting example, pain, inflammation, and others.

12 Claims, 7 Drawing Sheets

OTHER PUBLICATIONS

Shi Y et al. (2003). Mol Cell Biol. 23:7732-41. "Elimination of protein kinase MK5/PRAK activity by targeted homologous recombination."

Seternes OM. (2004). EMBO J. 23:4780-91. "Activation of MK5/PRAK by the atypical MAP kinase ERK3 defines a novel signal transduction pathway."

Andreakos E, et al. (2003). Arthritis Rheum. 48: 1901-12. "Heterogeneous requirement of IkB kinase 2 for inflammatory cytokine and matrix metalloproteinase production in RA".

Cunnane G, et al. (2001). Arthritis Rheum 44: 2263-74. "Early joint erosion and serum levels of matrix metalloproteinase 1, matrix metalloproteinase 3, . . . ".

Coussens LM, et al. (2002). Science 295: 2387-92. "Matrix metalloproteinase inhibitors and cancer: trials and tribulations".

Creemers EE, et al. (2001). Circ Res. 2001 89:201-10 "Matrix metalloproteinase inhibition after myocardial infarction".

Gapski R, et al. (2004). J Periodontol. 75:441-52. "Confusion between definitive and exploratory clinical therapy trials: when to believe and when to question".

Reif S et al. (2005) Digestion. 71:124-130. "Matrix metalloproteinases 2 and 9 are markers of inflammation but not of the degree of fibrosis in chronic hepatitis C".

Rosenberg GA. (2002). Glia. 39:279-91. "Matrix metalloproteinases in neuroinflammation".

Schanstra JP, et al. (2002). J Clin Invest. 110:371-9. "In vivo bradykinin B2 receptor activation reduces renal fibrosis".

Suzuki R, et al. (2004). Treat Respir Med. 3:17-27. "Matrix metalloproteinase in the pathogenesis of asthma and COPD".

Bundgaard, H. (1992). Adv Drug Deliv Rev. 8, 1-38. "Means to enhance penetraction. (1) Prodrugs as means to improve the delivery of peptide drugs".

N. Kakeya et al, Chem. Pharm. Bull., 32, 692 (1984); "Studies on prodrugs of cephalosporins . . . ".

J.H. Jones et al., J. Med. Chem. 1969, 12, 285-87. "Pyrazine diuretics. VII. N-Amidino-3-substituted pyrazinecarboxamides."

H. Newman et al., J. Heterocycl. Chem, 1974, 11, 449-451. "The preparation of 2,5-diazabicycio[2.2.2]octane: A bridged piperazine."

D. Barlocco et al., J. Med.Chem., 1998, 41, 674-681. "Mono- and distributed Disubstituted-3,8-diazabicyclo[3.2.1] octane Derivatives as Analgesics . . .".

DiMauro et al., J. Med. Chem.,2008, 51, 1681-1694. "Structure-Guided Design of Aminopyrimidine Amides as Potent, Selective Inhibitors of Lymphocyte Specific Kinase."

J.M. Keith et al., Bioorg. Med Chem Lett, 2008; 4838-4843. "Thiadiazolopiperazinyl ureas as inhibitors of fatty acid amide hydrolase."

* cited by examiner

Schematic view of a normal joint and its changes in rheumatoid arthritis
(From Smolen and Steiner, 2003).

\* p<0,05    \*\* p<0,01    \*\*\* p<0,001

SEQUENCE LISTING

<160> NUMBER OF SEQ ID NOS: 6

<210> SEQ ID NO 1
<211> LENGTH: 19
<212> TYPE: DNA
<213> ORGANISM: artificial
<220> FEATURE:
<223> OTHER INFORMATION: Target sequence

<400> SEQUENCE: 1

-continued

```
gctgaccctg aagttcatc                                                    19

<210> SEQ ID NO 2
<211> LENGTH: 19
<212> TYPE: DNA
<213> ORGANISM: Artificial
<220> FEATURE:
<223> OTHER INFORMATION: Target Sequence

<400> SEQUENCE: 2
ggttacctaa gggtgtggc                                                    19

<210> SEQ ID NO 3
<211> LENGTH: 19
<212> TYPE: DNA
<213> ORGANISM: Artificial
<220> FEATURE:
<223> OTHER INFORMATION: Target sequence

<400> SEQUENCE: 3
ctctgagtgc agtgaaatc                                                    19

<210> SEQ ID NO 4
<211> LENGTH: 19
<212> TYPE: DNA
<213> ORGANISM: Artificial
<220> FEATURE:
<223> OTHER INFORMATION: Target sequence

<400> SEQUENCE: 4
acaagagcaa gatgtggac                                                    19

<210> SEQ ID NO 5
<211> LENGTH: 19
<212> TYPE: DNA
<213> ORGANISM: Artificial
<220> FEATURE:
<223> OTHER INFORMATION: Target sequence

<400> SEQUENCE: 5
cggcacttta cagagaagc                                                    19

<210> SEQ ID NO 6
<211> LENGTH: 19
<212> TYPE: DNA
<213> ORGANISM: Artificial
<220> FEATURE:
<223> OTHER INFORMATION: Target sequence

<400> SEQUENCE: 6
atgatgtgtg ccacacacc                                                    19
```

SUBSTITUTED TRIAZOLOPYRAZINES USEFUL FOR THE TREATMENT OF DEGENERATIVE AND INFLAMMATORY DISEASES

RELATED APPLICATIONS

The present application claims the benefit under 35 U.S.C. §119 of U.S. Provisional Application No. 61/126,833, filed May 7, 2008, and U.S. Provisional Application No. 61/145,827, filed Jan. 20, 2009, the contents of each of which are hereby incorporated by reference in their entireties.

FIELD OF THE INVENTION

The present invention relates to a class of fused pyrazine compounds capable of binding to the active site of a serine/threonine kinase, the expression of which is involved in the pathway resulting in the degradation of extra-cellular matrix (ECM), joint degeneration and diseases involving such degradation and/or inflammation.

Diseases involving the degradation of extra-cellular matrix include, but are not limited to, psoriatic arthritis, juvenile arthritis, early arthritis, reactive arthritis, osteoarthritis, rheumatoid arthritis, ankylosing spondylitis, osteoporosis, muskulo skeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, rheumatoid arthritis, osteoarthritis, and ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Although it is widely accepted that RA is an auto-immune disease, there is no consensus concerning the precise mechanisms driving the 'initiation stage' of the disease. What is known is that the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). When the disease progresses, the cellular activation and cytokine production cascade becomes self-perpetuating. At this early stage, the destruction of joint structures is already very clear. Thirty percent of the patients have radiographic evidence of bony erosions at the time of diagnosis and this proportion increases to 60 percent after two years.

Histological analysis of the joints of RA patients clearly evidences the mechanisms involved in the RA-associated degradative processes. This analysis shows that the main effector responsible for RA-associated joint degradation is the pannus, where the synovial fibroblast, by producing diverse proteolytic enzymes, is the prime driver of cartilage and bone erosion. A joint classically contains two adjacent bones that articulate on a cartilage layer and are surrounded by the synovial membrane and joint capsule. In the advanced RA patient, the synovium of the joint increases in size to form the pannus, due to the proliferation of the synovial fibroblasts and the infiltration of mononuclear cells such as T-cells, B-cells, monocytes, macrophages and neutrophils. The pannus mediates the degradation of the adjacent cartilage, leading to the narrowing of the joint space, and has the potential to invade adjacent bone and cartilage. As bone and cartilage tissues are composed mainly of collagen type I or II, respectively, the pannus destructive and invasive properties are mediated by the secretion of collagenolytic proteases, principally the matrix metallo proteinases (MMPs). The erosion of the bone under and adjacent to the cartilage is also part of the RA process, and results principally from the presence of osteoclasts at the interface of bone and pannus. Osteoclasts are multinucleated cells that, upon adhesion to the bone tissue, form a closed compartment, within which the osteoclasts secrete proteases (Cathepsin K, MMP9) that degrade the bone tissue. The osteoclast population in the joint is abnormally increased by osteoblast formation from precursor cells induced by the secretion of the receptor activator of NFκB ligand (RANKL) by activated SFs and T-cells.

Various collagen types have a key role in defining the stability of the extracellular matrix (ECM). Collagen type I and collagen type II, for example, are the main components of bone and cartilage, respectively. Collagen proteins typically organise into multimeric structures referred to as collagen fibrils. Native collagen fibrils are very resistant to proteolytic cleavage. Only a few types of ECM-degrading proteins have been reported to have the capacity to degrade native collagen: MMPs and Cathepsins. Among the Cathepsins, cathepsin K, which is active mainly in osteoclasts, is the best characterised. Among the MMPs, MMP1, MMP2, MMP8 MMP13 and MMP14 are known to have collagenolytic properties. The correlation between an increased expression of MMP1 by synovial fibroblasts (SFs) and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation. Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, muscular skeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reiff et al., 2005), cardio-vascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

The 471-amino acid serine/threonine kinase identified as Mitogen-Activated Protein Kinase-Activated Protein Kinase 5 (MAPKAPK5 or PRAK) is expressed in a wide panel of tissues. The protein contains its catalytic domain at the N-terminal end and both a nuclear localization signal (NLS) and nuclear export signal (NES) at its C-terminal end. Endogenous MAPKAPK5 is predominantly present in the cytoplasm, but stress or cytokine activation of the cells mediates its translocation into the nucleus (New et al., 2003). This event is dependent on phosphorylation of MAPKAPK5. Thr182 is the regulatory phosphorylation site of MAPKAPK5. Although the p38α kinase is able to phosphorylate MAPKAPK5 in an overexpression setting, experiments with endogenous MAPKAPK5 do not support this hypothesis (Shi et al., 2003). MAPKAPK5 knock-out mice have been generated that are viable and fertile. The phenotype of these mice is quite different from that of mice deficient for MAPKAPK2, a MAPKAPK5 related kinase that is regulated by p38α (Shi et al., 2003). This indicates that the function of each protein is distinct and that neither kinase can compensate for the other's activity. Taken together, MAPKAPK5 and MAPKAPK2 represent distinct targets with a non-redundant role. MAPK6 (also referred to as ERK3) has recently been identified as a physiologically relevant substrate for MAPKAPK5, defining a novel signal transduction pathway (Seternes et al., 2004).

BACKGROUND OF THE INVENTION

NSAIDS (Non-steroidal anti-inflammatory drugs) are used to reduce the pain associated with RA and improve life quality of the patients. These drugs will not, however, put a brake on the RA-associated joint destruction.

Corticosteroids were found to decrease the progression of RA as detected radiographically and are used at low doses to treat part of the RA patients (30 to 60%). Serious side effects, however, are associated with long corticosteroid use (skin thinning, osteoporosis, cataracts, hypertension, and hyperlipidemia).

Synthetic DMARDs (Disease-Modifying Anti-Rheumatic Drugs) (e.g. methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve an ACR50 score after 24 months treatment with methotrexate. This means that, according to the American College of Rheumatology, only 30% of the patients do achieve a 50% improvement of their symptoms (O'Dell et al., 1996). In addition, the precise mechanism of action of DMARDs is often unclear.

Biological DMARDs (Infliximab, Etanercept, Adalimumab, Rituximab, Abatacept) are therapeutic proteins that do inactivate cytokines (e.g. TNF-α) or cells (e.g. B-cells or T-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR50) in disease symptoms in 50-60% of patients after 12 months therapy (St Clair et al., 2004). Some adverse events warnings for anti-TNF-α drugs exist, shedding a light on the side effects associated to this type of drugs. Increased risk for infections (tuberculosis), hematologic events and demyelinating disorders have been described for the TNF-α blockers (see also Gomez-Reino et al., 2003). Besides the serious side effects, the TNF-α blockers do also share the general disadvantages of the biological class of therapeutics, which are the unpleasant way of administration (frequent injections accompanied by infusion site reactions) and the high production cost. Newer agents in late development phase target cytokines such as IL-6, T-cell co-stimulatory molecules and B-cells. The efficacy of these agents is expected to be similar to that of the TNF-α blockers. The fact that a variety of targeted therapies have similar but limited efficacies, suggests that there is a multiplicity of pathogenic factors for RA. This is also indicative for the deficiencies in our understanding of pathogenic events relevant to RA.

The current therapies for RA are not satisfactory due to a limited efficacy (no adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

US 2005/0009832 describes substituted imidazo[1,2-a]pyrazine-8-yl-amines as modulators of protein kinases, including MAPKAPK5. WO02/056888 describes inhibitors of MAPKAPK5 as TNF modulators able to regulate the expression of certain cytokines. Neither of these prior art references discloses any compound within the scope of the class of compounds described herein below.

SUMMARY OF THE INVENTION

The present invention is based on the discovery that MAPKAPK5 functions in the pathway that results in the expression of MMP1, and that inhibitors of MAPKAPK5 activity, such as the compounds of the present invention, are useful for the treatment of diseases involving the abnormally high expression of MMP activity.

The compounds of the invention may be described generally as [1.2.4]triazolo[1,5-a]pyrazines and imidazo[1,2-a]pyrazines substituted in the 5-position by an aryl or heteroaryl group, and an in the 8-position by a heteroarylamino group.

The compounds of the invention may show less toxicity, good absorption, good half-life, good solubility, low protein binding affinity, less drug-drug interaction, and good metabolic stability. In a particular aspect, the compounds of the present invention exhibit unexpected significant improvements in pharmacological properties, in particular improved efficacy and improved tolerability.

More particularly, the present invention relates to a compound of the invention according to Formula (Ia) or (Ib):

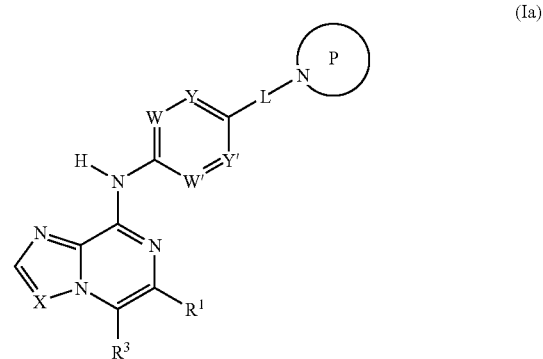

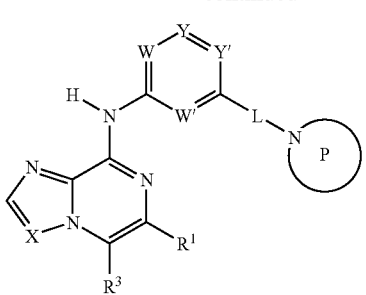

(Ib)

wherein
each of W, W', Y, and Y' is independently $CR^{2a}$ or N; provided that no more than two of W, W', Y, and Y' can be N at the same time;
X is N or CH;
L is selected from a single bond, —CO—, —SO—, —$SO_2$—, —$N(R^{2c})CO$—, and —$N(R^{2c})SO_2$—;
the ring P is substituted or unsubstituted:

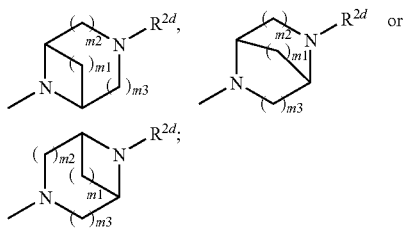

R' is H, or substituted or unsubstituted $C_1$-$C_6$ alkyl;
each $R^{2a}$ is independently selected from H, substituted or unsubstituted $C_1$-$C_6$ alkyl, $C_1$-$C_6$ alkoxy, cyano, and halo;
each $R^{2c}$ is selected from H and $C_1$-$C_6$ alkyl;
$R^{2d}$ is H, $C_3$-$C_8$ cycloalkyl, or $C_1$-$C_6$ alkyl optionally substituted with halo, amido, or $C_3$-$C_8$ cycloalkyl; each m1, m2 and m3 is independently 1 or 2; and
$R^3$ is selected from substituted or unsubstituted $C_1$-$C_6$ alkyl, substituted or unsubstituted cycloalkyl, substituted or unsubstituted heterocycloalkyl, substituted or unsubstituted aryl, and substituted or unsubstituted heteroaryl.

In one embodiment, with respect to a compound of the invention according to Formula I or Ib, $R^1$ is H, Me, Et, i-Pr or $CF_3$.

In one embodiment, with respect to a compound of the invention according to Formula Ia or Ib, $R^1$ is H.

In another embodiment, with respect to a compound of the invention according to Formula Ia or Ib, $R^3$ is selected from substituted or unsubstituted phenyl.

In another embodiment, with respect to a compound of the invention according to Formula Ia or Ib, $R^3$ is selected from substituted or unsubstituted pyridyl.

In another embodiment, with respect to a compound of the invention according to Formula Ia or Ib, $R^3$ is selected from phenyl, indolyl, isoinolyl, pyrrolyl, furanyl, thienyl, pyrazolyl, oxazolyl, and thiazolyl, each of which may be substituted or unsubstituted.

In a preferred embodiment, with respect to a compound of the invention according to Formula Ia or Ib, $R^3$ is substituted or unsubstituted furanyl.

In a further aspect, the present invention provides pharmaceutical compositions comprising a compound of the invention, and a pharmaceutical carrier, excipient or diluent. In this aspect of the invention, the pharmaceutical composition can comprise one or more of the compounds of the invention described herein. Moreover, the compounds of the invention useful in the pharmaceutical compositions and treatment methods disclosed herein, are all pharmaceutically acceptable as prepared and used.

Another aspect of this invention relates to the use of a compound of the invention in a therapeutic method, a pharmaceutical composition, and the manufacture of such composition, useful for the treatment of diseases involving inflammation, collagen degradation, and in particular, diseases characteristic of abnormal matrix metallo protease (MMP1) and/or Mitogen-Activated Protein-Kinase Activated Protein Kinase 5 (MAPKAPK5) activity, of which rheumatoid arthritis (RA) is a particular such disease. This invention also relates to processes for the preparation of the compounds of the invention.

Other objects and advantages will become apparent to those skilled in the art from a consideration of the ensuing detailed description, considered in conjunctin with the following illustrative drawings.

DETAILED DESCRIPTION OF THE INVENTION

Definitions

Figure 1:
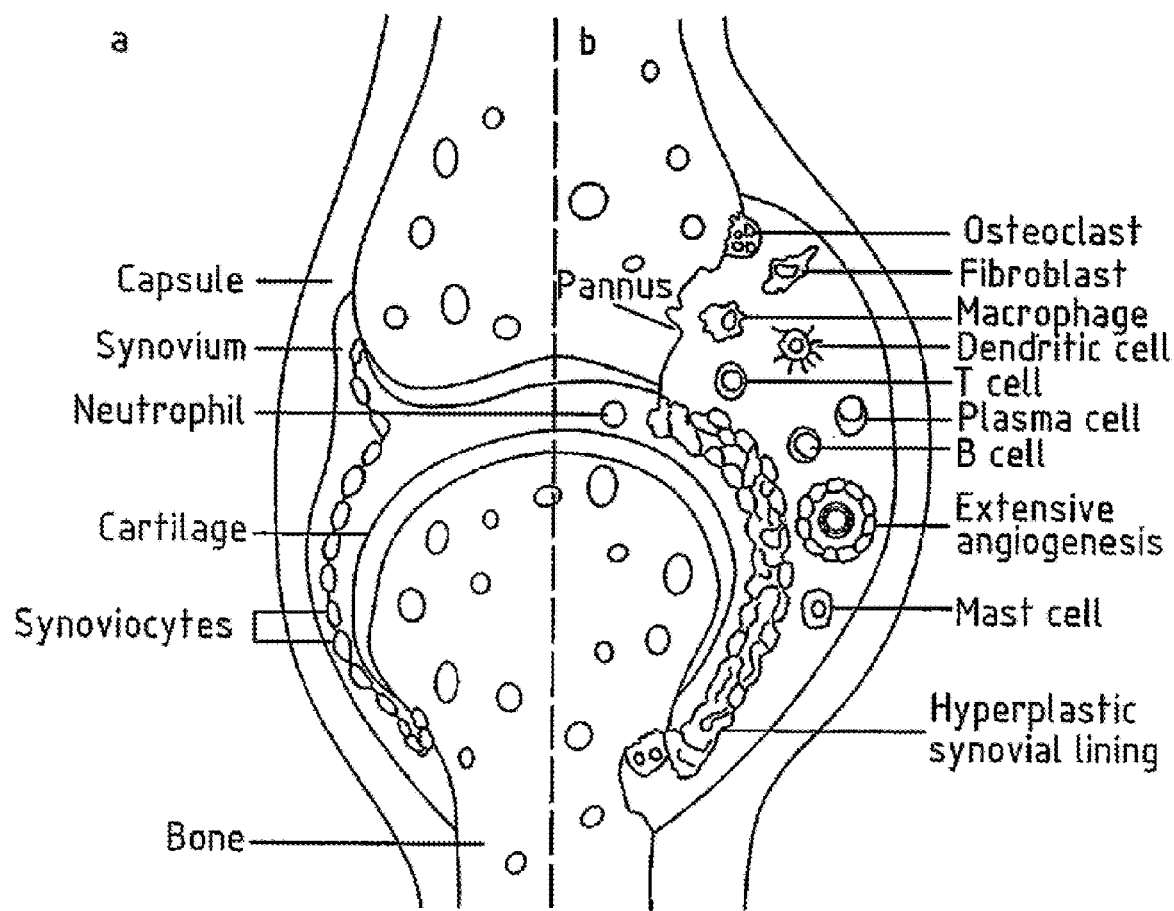
FIG. 1. This diagram shows the striking histological differences between a healthy joint and that of a RA patient.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below.

Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)R$^{20}$, where R$^{20}$ is hydrogen, C$_1$-C$_8$ alkyl, C$_3$-C$_{10}$ cycloalkyl, C$_3$-C$_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
C$_1$-C$_8$ alkyl, substituted with halo or hydroxy; or
C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Acylamino' refers to a radical —NR$^{22}$C(O)R$^{23}$, where R$^{22}$ is hydrogen, C$_1$-C$_8$ alkyl, C$_3$-C$_{10}$ cycloalkyl, 4-10 membered heterocycloalkyl, C$_6$-C$_{10}$ aryl, arylalkyl, 5-10 memberd heteroaryl or heteroarylalkyl and R$^{23}$ is hydrogen, C$_1$-C$_8$ alkyl, C$_3$-C$_{10}$ cycloalkyl, 4-10 membered heterocycloalkyl, C$_6$-C$_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Exemplary 'acylamino' groups are —NR$^{21'}$C(O)—C$_1$-C$_8$ alkyl, —NR$^{21'}$C(O)—(CH$_2$)$_t$(C$_6$-C$_{10}$ aryl), —NR$^{21'}$C(O)—(CH$_2$)$_t$(5-10 membered heteroaryl), —NR$^{21'}$C(O)—(CH$_2$)$_t$(C$_3$-C$_{10}$ cycloalkyl), and —NR$^{21'}$C(O)—(CH$_2$)$_t$(4-10 membered heterocycloalkyl), wherein t is an integer from 0 to 4, each R$^{21'}$ independently represents H or C$_1$-C$_8$ alkyl.

'Substituted Acylamino' refers to a radical —NR$^{24}$C(O)R$^{25}$, wherein:
R$^{24}$ is independently
H, C$_1$-C$_8$ alkyl, substituted with halo or hydroxy; or
C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and
R$^{25}$ is independently
H, C$_1$-C$_8$ alkyl, substituted with halo or hydroxy; or
C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl;
provided at least one of R$^{24}$ and R$^{25}$ is other than H.

'Alkoxy' refers to the group —OR$^{26}$ where R$^{26}$ is C$_1$-C$_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, C$_6$-C$_{10}$ aryl, —O— aryl, carboxyl, cyano, C$_3$-C$_{10}$ cycloalkyl, 4-10 membered heterocycloalkyl, halogen, 5-10 membered heteroaryl, hydroxyl, nitro, thioalkoxy, thio-O-aryl, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, OCH$_2$CH$_2$NMe$_2$.

'Alkoxycarbonyl' refers to a radical —C(O)—OR$^{27}$ where R$^{27}$ represents an C$_1$-C$_8$ alkyl, C$_3$-C$_{10}$ cycloalkyl, C$_3$-C$_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—C$_1$-C$_8$ alkyl, —C(O)O—(CH$_2$)$_t$(C$_6$-C$_{10}$ aryl), —C(O)O—(CH$_2$)$_t$(5-10 membered heteroaryl), —C(O)O—(CH$_2$)$_t$(C$_3$-C$_{10}$ cycloalkyl), and —C(O)O—(CH$_2$)$_t$(4-10 membered heterocycloalkyl), wherein t is an integer from 1 to 4.

'Substituted Alkoxycarbonyl' refers to a radical —C(O)—OR$^{28}$ where R$^{28}$ represents:
C$_1$-C$_8$ alkyl, C$_3$-C$_{10}$ cycloalkyl, C$_3$-C$_{10}$ cycloalkylalkyl, or 4-10 membered heterocycloalkylalkyl, each of which is substituted with halo, substituted or unsubstituted amino, or hydroxy; or
C$_6$-C$_{10}$ aralkyl, or 5-10 membered heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'—O-arylcarbonyl' refers to a radical —C(O)—OR$^{29}$ where R$^{29}$ represents an C$_6$-C$_{10}$ aryl, as defined herein. Exemplary "—O-arylcarbonyl" groups is —C(O)O—(C$_6$-C$_{10}$ aryl).

'Substituted —O-arylcarbonyl' refers to a radical —C(O)—OR$^{30}$ where R$^{30}$ represents a
C$_6$-C$_{10}$ aryl, substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Hetero-O-arylcarbonyl' refers to a radical —C(O)—OR$^{31}$ where R$^{31}$ represents a 5-10 membered heteroaryl, as defined herein.

'Substituted Hetero-O-arylcarbonyl' refers to a radical —C(O)—OR$^{32}$ where R$^{32}$ represents a:
5-10 membered heteroaryl, substituted with unsubstituted C$_1$-C$_4$ alkyl, halo, unsubstituted C$_1$-C$_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—O$R^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-aryl, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R''', —SO$_2$NR''R''', —C(O)R''', —C(O)OR''', —OC(O)R''', —NR'''C(O)R''', —C(O)NR''R''', —NR''R''', or —(CR'''R'''')$_m$OR'''; wherein each R'' is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

'Amino' refers to the radical —NH$_2$.

'Substituted amino' refers to an amino group substituted with one or more of those groups recited in the definition of 'substituted' herein, and particularly refers to the group —N($R^{33}$)$_2$ where each $R^{33}$ is independently selected from:
hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or
$C_1$-$C_8$ alkyl, substituted with halo or hydroxy; or
—(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or
both $R^{33}$ groups are joined to form an alkylene group.

When both $R^{33}$ groups are hydrogen, —N($R^{33}$)$_2$ is an amino group. Exemplary 'substituted amino' groups are —NR$^{33'}$—$C_1$-$C_8$ alkyl, —NR$^{33'}$—(CH$_2$)$_t$($C_6$-$C_{10}$ aryl), —NR$^{33'}$—(CH$_2$)$_t$(5-10 membered heteroaryl) —NR$^{33'}$—(CH$_2$)$_t$($C_3$-$C_{10}$ cyclo alkyl), and —NR$^{33'}$—(CH$_2$)$_t$(4-10 membered heterocycloalkyl), wherein t is an integer from 0 to 4, each $R^{33'}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{34}$, wherein $R^{34}$ is $C_1$-$C_8$ alkyl.

'Substituted Alkylamino' refers to the group —NHR$^{35}$, wherein $R^{35}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —NR$^{36}$R$^{37}$, wherein $R^{36}$ is $C_6$-$C_{10}$ aryl and $R^{37}$ is $C_1$-$C_8$ alkyl.

'Substituted Alkylarylamino' refers to the group —NR$^{38}$R$^{39}$, wherein $R^{38}$ is $C_6$-$C_{10}$ aryl and $R^{39}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —NHR$^{40}$ where $R^{40}$ is selected from $C_6$-$C_{10}$ aryl and 5-10 membered heteroaryl as defined herein.

'Substituted Arylamino' refers to the group —NHR$^{41}$, wherein $R^{41}$ is independently selected from $C_6$-$C_{10}$ aryl and 5-10 membered heteroaryl; and any aryl or heteroaryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Dialkylamino' refers to the group —NR$^{42}$R$^{43}$, wherein each of $R^{42}$ and $R^{43}$ are independently selected from $C_1$-$C_8$ alkyl.

'Substituted Dialkylamino' refers to the group —NR$^{44}$R$^{45}$, wherein each of $^{44}$ and $R^{45}$ are independently selected from $C_1$-$C_8$ alkyl; and the alkyl group is independently substituted with halo, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Diarylamino' refers to the group —NR$^{46}$R$^{47}$, wherein each of $R^{46}$ and $R^{47}$ are independently selected from $C_6$-$C_{10}$ aryl.

"Aminosulfonyl" or "Sulfonamide" refers to the radical —S(O$_2$)NH$_2$.

"Substituted aminosulfonyl" or "substituted sulfonamide" refers to a radical such as —S(O$_2$)N(R$^{48}$)$_2$ wherein each R$^{48}$ is independently selected from:

H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{48}$ is other than H.

Exemplary 'substituted aminosulfonyl' or 'substituted sulfonamide' groups are —S(O$_2$)N(R$^{48'}$)—C$_1$-C$_8$ alkyl, —S(O$_2$)N(R$^{48'}$)—(CH$_2$)$_t$(C$_6$-C$_{10}$ aryl), —S(O$_2$)N(R$^{48'}$)—(CH$_2$)$_t$(5-10 membered heteroaryl), —S(O$_2$)N(R$^{48'}$)—(CH$_2$)$_t$(C$_3$-C$_{10}$ cycloalkyl), and —S(O$_2$)N(R$^{48'}$)—(CH$_2$)$_t$(4-10 membered heterocycloalkyl), wherein t is an integer from 0 to 4; each R$^{48'}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of any aryl group present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, C$_1$-C$_8$ alkyl, C$_1$-C$_8$ haloalkyl, C$_1$-C$_8$ haloalkoxy, cyano, hydroxy, C$_1$-C$_8$ alkoxy, and amino.

Examples of representative substituted aryls include the following

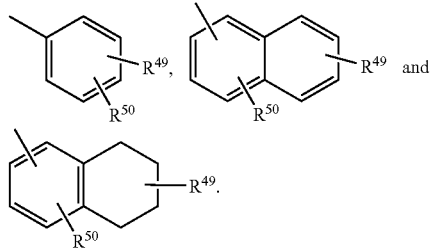

In these formulae one of R$^{49}$ and R$^{50}$ may be hydrogen and at least one of R$^{49}$ and R$^{50}$ is each independently selected from C$_1$-C$_8$ alkyl, 4-10 membered heterocycloalkyl, alkanoyl, C$_1$-C$_8$ alkoxy, hetero-O-aryl, alkylamino, arylamino, heteroarylamino, NR$^{51}$COR$^{52}$, NR$^{51}$SOR$^{52}$NR$^{51}$SO$_2$R$^{52}$, COOalkyl, COOaryl, CONR$^{51}$R$^{52}$, CONR$^{51}$OR$^{52}$, NR$^{51}$R$^{52}$, SO$_2$NR$^{51}$R$^{52}$, S-alkyl, SOalkyl, SO$_2$alkyl, Saryl, SOaryl, SO$_2$aryl; or R$^{49}$ and R$^{50}$ may be joined to form a cyclic ring (saturated or unsaturated) from 5 to 8 atoms, optionally containing one or more heteroatoms selected from the group N, O or S. R$^{51}$, and R$^{52}$ are independently hydrogen, C$_1$-C$_8$ alkyl, C$_1$-C$_4$ haloalkyl, C$_3$-C$_{10}$ cycloalkyl, 4-10 membered heterocycloalkyl, C$_6$-C$_{10}$ aryl, substituted aryl, 5-10 membered heteroaryl.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted C$_1$-C$_4$ alkyl, halo, cyano, unsubstituted C$_1$-C$_4$ alkoxy, unsubstituted C$_1$-$_4$ haloalkyl, unsubstituted C$_1$-C$_4$ hydroxyalkyl, or unsubstituted C$_1$-C$_4$ haloalkoxy or hydroxy.

'Azido' refers to the radical —N$_3$.

'Carbamoyl or amido' refers to the radical —C(O)NH$_2$.

'Substituted Carbamoyl or substituted amido' refers to the radical —C(O)N(R$^{53}$)$_2$ wherein each R$^{53}$ is independently H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{53}$ is other than H.

Exemplary 'Substituted Amido/Carbamoyl' groups are —C(O) NR$^{53'}$—C$_1$-C$_8$ alkyl, —C(O)NR$^{53'}$—(CH$_2$)$_t$(C$_6$-C$_{10}$ aryl), —C(O)N$^{53'}$—(CH$_2$)$_t$(5-10 membered heteroaryl), —C(O)NR$^{53'}$—(CH$_2$)$_t$(C$_3$-C$_{10}$ cycloalkyl), and —C(O) NR$^{53'}$—(CH$_2$)$_t$(4-10 membered heterocycloalkyl), wherein t is an integer from 0 to 4, each R$^{53'}$ independently represents H or C$_1$-C$_8$ alkyl and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, cyclohexyl, cycloheptyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative aryl having hetero atoms containing substitution include the following:

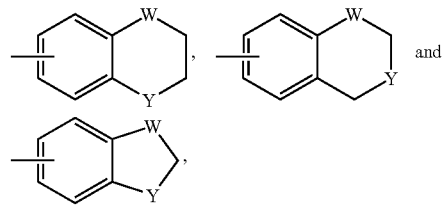

wherein each W is selected from $C(R^{54})_2$, $NR^{54}$, O and S; and each Y is selected from carbonyl, $NR^{54}$, O and S; and $R^{54}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative heteroaryls include the following:

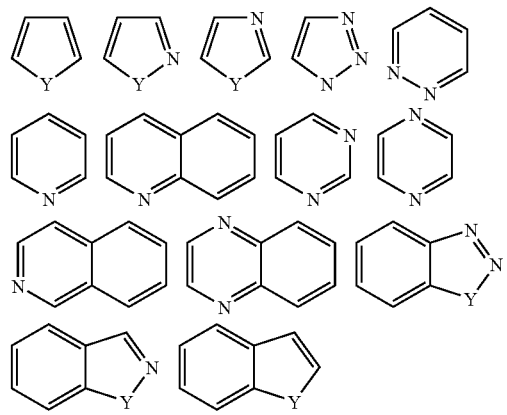

wherein each Y is selected from carbonyl, N, $NR^{55}$, O and S; and $R^{55}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

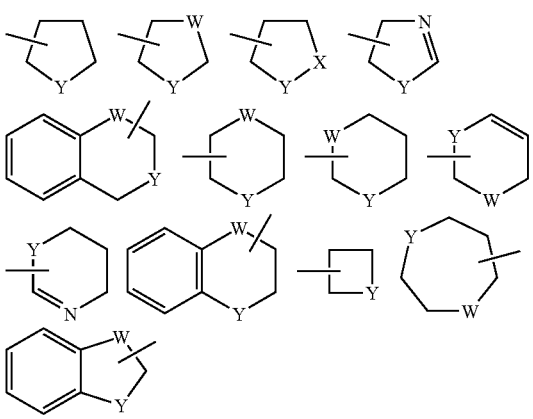

wherein each W is selected from CR$^{56}$, C(R$^{56}$)$_2$, NR$^{56}$, O and S; and each Y is selected from NR$^{56}$, O and S; and R$^{56}$ is independently hydrogen, C$_1$-C$_8$ alkyl, C$_3$-C$_{10}$ cycloalkyl, 4-10 membered heterocycloalkyl, C$_6$-C$_{10}$ aryl, 5-10 membered heteroaryl, These heterocycloalkyl rings may be optionally substituted with one or more groups selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-aryl, azido, carboxyl, cyano, cycloalkyl, halogen, hydroxy, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —R$^{57}$, —O$^-$, =O, —OR$^{57}$, —SR$^{57}$, —S$^-$, =S, —NR$^{57}$R$^{58}$, =NR$^{57}$, —CCl$_3$, —CF$_3$, —CN, —OCN, —SCN, —NO, —NO$_2$, =N$_2$, —N$_3$, —S(O)$_2$O$^-$, —(O)$_2$OH, —S(O)$_2$R$^{57}$, —OS(O$_2$)O$^-$, —OS(O)$_2$R$^{57}$, —P(O)(O$^-$)$_2$, —P(O)(OR$^{57}$)(O$^-$), —OP(O)(OR$^{57}$)(OR$^{58}$), —C(O)R$^{57}$, —C(S)R$^{57}$, —C(O)OR$^{57}$, —C(O)NR$^{57}$R$^{58}$, —C(O)O$^-$, —C(S)OR$^{57}$, —NR$^{59}$C(O)NR$^{57}$R$^{58}$, —NR$^{59}$C(S)NR$^{57}$R$^{58}$, —NR$^{60}$C(NR$^{59}$)NR$^{57}$R$^{58}$ and —C(NR$^{59}$)NR$^{57}$R$^{58}$;

wherein each R$^{57}$, R$^{58}$, R$^{59}$ and R$^{60}$ are independently:

hydrogen, C$_1$-C$_8$ alkyl, C$_6$-C$_{10}$ aryl, arylalkyl, C$_3$-C$_{10}$ cycloalkyl, 4-10 membered heterocycloalkyl, 5-10 membered heteroaryl, heteroarylalkyl; or C$_1$-C$_8$ alkyl substituted with halo or hydroxy; or C$_6$-C$_{10}$ aryl, 5-10 membered heteroaryl, C$_6$-C$_{10}$ cycloalkyl or 4-10 membered heterocycloalkyl substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from: halo, cyano, nitro, trifluoromethyl, trifluoromethoxy, azido, —NR'"SO$_2$R'", —SO$_2$NR"R'", —C(O)R", —C(O)OR", —OC(O)R", —NR'"C(O)R", —C(O)NR"R'", —NR"R'", —(CR'"R'")$_m$OR'", wherein, each R" is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each R'" independently represents H or C$_1$-C$_6$alkyl.

'Substituted sulfanyl' refers to the group —SR$^{61}$, wherein R$^{61}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$(C$_3$-C$_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —SR$^{62}$ where R$^{62}$ is a C$_1$-C$_8$ alkyl or group as defined herein. Representative examples include, but are not limited to, methylthio, ethylthio, propylthio and butylthio.

'Substituted Alkylthio' or 'substituted alkylsulfanyl' refers to the group —SR$^{63}$ where R$^{63}$ is a C$_1$-C$_8$ alkyl, substituted with halo, substituted or unsubstituted amino, or hydroxy.

'Cycloalkylthio' or 'Cycloalkylsulfanyl' refers to a radical —SR$^{64}$ where R$^{64}$ is a C$_3$-C$_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —SR$^{65}$ where R$^{65}$ is a C$_3$-C$_{10}$ cycloalkyl, substituted with halo, substituted or unsubstituted amino, or hydroxy.

'Arylthio' or 'Arylsulfanyl' refers to a radical —SR$^{66}$ where R$^{66}$ is a C$_6$-C$_{10}$ aryl group as defined herein.

'Heteroarylthio' or 'Heteroarylsulfanyl' refers to a radical —SR$^{67}$ where R$^{67}$ is a 5-10 membered heteroaryl group as defined herein.

'Substituted sulfinyl' refers to the group —S(O)R$^{68}$, wherein R$^{68}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfinyl' groups are —S(O)—(C$_1$-C$_8$ alkyl) and —S(O)—(C$_3$-C$_{10}$ cycloalkyl), —S(O)—(CH$_2$)$_t$(C$_6$-C$_{10}$ aryl), —S(O)—(CH$_2$)$_t$(5-10 membered heteroaryl), —S(O)—(CH$_2$)$_t$(C$_3$-C$_{10}$ cycloalkyl), and —S(O)-(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —S(O)R$^{69}$ where R$^{69}$ is a C$_1$-C$_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —S(O)R$^{70}$ where R$^{70}$ is a C$_1$-C$_8$ alkyl group as defined herein, substituted with halo, substituted or unsubstituted amino, or hydroxy.

'Cycloalkylsulfinyl' refers to a radical —S(O)R$^{71}$ where R$^{71}$ is a C$_3$-C$_{10}$ cycloalkyl or group as defined herein. Representative examples include, but are not limited to, cyclopropylsulfinyl, cyclohexylsulfinyl, and cyclopentylsulfinyl.

'Substituted cycloalkylsulfinyl' refers to the group —S(O)R$^{72}$ where R$^{72}$ is a C$_3$-C$_{10}$ cycloalkyl, substituted with halo, substituted or unsubstituted amino, or hydroxy.

'Arylsulfinyl' refers to a radical —S(O)R$^{73}$ where R$^{73}$ is a C$_6$-C$_{10}$ aryl group as defined herein.

'Heteroarylsulfinyl' refers to a radical —S(O)R$^{74}$ where R$^{74}$ is a 5-10 membered heteroaryl group as defined herein.

'Substituted sulfonyl' refers to the group —S(O)$_2$R$^{75}$, wherein R$^{75}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfonyl' groups are —S(O)$_2$—(C$_1$-C$_8$ alkyl) and —S(O)$_2$—(C$_3$-C$_{10}$ cycloalkyl), —S(O)$_2$—(CH$_2$)$_t$(C$_6$-C$_{10}$ aryl), —S(O)$_2$—(CH$_2$)$_t$(5-10 membered heteroaryl), —S(O)$_2$—(CH$_2$)$_t$(C$_3$-C$_{10}$ cycloalkyl), and —S(O)$_2$—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$R$^{76}$ where R$^{76}$ is an C$_1$-C$_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$R$^{77}$ where R$^{77}$ is an C$_1$-C$_8$ alkyl group as defined herein, substituted with halo, substituted or unsubstituted amino, or hydroxy.

'Cycloalkylsulfonyl' refers to a radical —S(O)$_2$R$^{78}$ where R$^{78}$ is a C$_3$-C$_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$R$^{79}$ where R$^{79}$ is a C$_3$-C$_{10}$ cycloalkyl, substituted with halo, substituted or unsubstituted amino, or hydroxy.

'Arylsulfonyl' refers to a radical —S(O)$_2$R$^{80}$ where R$^{80}$ is an C$_6$-C$_{10}$ aryl group as defined herein.

'Heteroarylsulfonyl' refers to a radical —S(O)$_2$R$^{81}$ where R$^{81}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$OR$^{82}$, wherein R$^{82}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'Substituted sulfo' or 'sulfonic acid ester' groups are —S(O)$_2$—O—(C$_1$-C$_8$ alkyl) and —S(O)$_2$—O—(C$_3$-C$_{10}$ cycloalkyl), —S(O)$_2$—O—(CH$_2$)$_t$(C$_6$-C$_{10}$ aryl), —S(O)$_2$—O—(CH$_2$)$_t$(5-10 membered heteroaryl), —S(O)$_2$—O—(CH$_2$)$_t$(C$_3$-C$_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound of the invention that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein the term 'compound(s) of the invention', and equivalent expressions, are meant to embrace compounds according to any one of the Formula(e) as herein described, which expression includes the pharmaceutically acceptable salts, the solvates of the compounds, and the solvates of the pharmaceutically acceptable salts, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of a compound of the invention may have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $_{18}$F, $^{15}$O and $^{13}$N, and would be useful in Positron Emission Topography (PET) studies for examining substrate receptor occupancy.

All isotopic variants of a compound of the invention provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Such tautomers, as appropriate, are encompassed within the compounds of the invention as disclosed herein.

Tautomeric forms may be relevant to the attainment of the optimal chemical reactivity and biological activity of a compound of interest.

A compound of the invention may possess one or more asymmetric centers; such a compound can therefore be produced as an individual (R)- or (S)-stereoisomer or as a mixture thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is based on the discovery that MAPKAPK5 functions in the pathway that results in the expression of MMP1, and that inhibitors of MAPKAPK5 activity, such as the compounds of the invention, are useful for the treatment of diseases involving the abnormally high expression of MMP activity.

The compounds of the invention may be described generally as [1.2.4]triazolo[1,5-a]pyrazines and imidazo[1,2-a]pyrazines substituted in the 5-position by an aryl or heteroaryl group, and an in the 8-position by a heteroarylamino group.

The compounds of the invention may show less toxicity, good absorption, good half-life, good solubility, low protein binding affinity, less drug-drug interaction, and good metabolic stability. In a particular aspect, the compounds of the invention exhibit unexpected significant improvements in pharmacological properties, in particular improved efficacy and improved tolerability.

More particularly, the present invention relates to a compound of the invention according to Formula Ia or Ib:

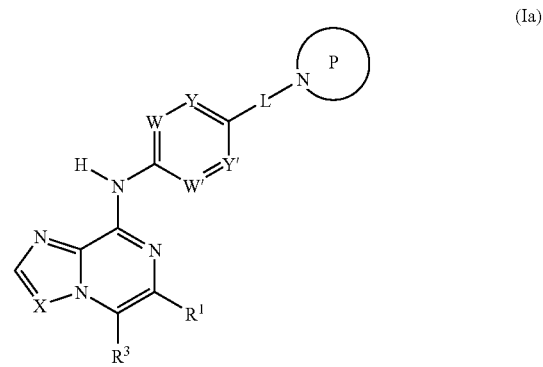

(Ia)

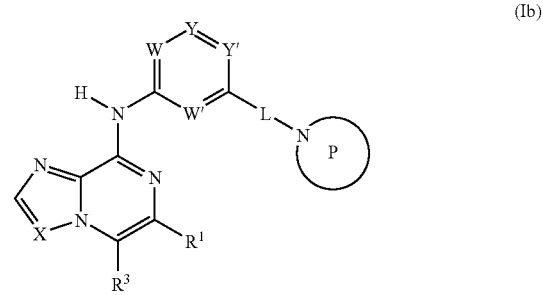

(Ib)

wherein
each of W, W', Y, and Y' is independently $CR^{2a}$ or N;
provided that no more than two of W, W', Y, and Y' can be N at the same time;
X is N or CH;
L is selected from a single bond, —CO—, —SO—, —SO$_2$—, —N($R^{2c}$)CO—, and —N($R^{2c}$)SO$_2$—;
the ring P is substituted or unsubstituted:

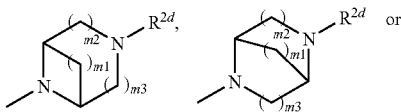

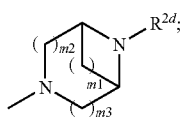

$R^1$ is H, or substituted or unsubstituted $C_1$-$C_6$ alkyl;

each $R^{2a}$ is independently selected from H, substituted or unsubstituted $C_1$-$C_6$ alkyl, $C_1$-$C_6$ alkoxy, cyano, and halo;

each $R^{2c}$ is selected from H and $C_1$-$C_6$ alkyl;

$R^{2d}$ is H, $C_3$-$C_8$ cycloalkyl, or $C_1$-$C_6$ alkyl optionally substituted with halo, amido, or $C_3$-$C_8$ cycloalkyl; each m1, m2 and m3 is independently 1 or 2; and $R^3$ is selected from substituted or unsubstituted $C_1$-$C_6$ alkyl, substituted or unsubstituted cycloalkyl, substituted or unsubstituted heterocycloalkyl, substituted or unsubstituted aryl, and substituted or unsubstituted heteroaryl.

In one embodiment, with respect to a compound of the invention according to Formula Ia or Ib, $R^1$ is H, Me, Et, i-Pr or $CF_3$.

In one embodiment, with respect to a compound of the invention according to Formula Ia or Ib, $R^1$ is H.

In one embodiment, with respect to a compound of the invention according to Formula Ia or Ib, L is a single bond, —CO—, or —N($R^{2c}$)CO—.

In one particular embodiment, with respect to a compound of the invention according to Formula Ia or Ib, L is a single bond.

In one embodiment, with respect to a compound of the invention according to Formula Ia or Ib, $R^1$ is Me, Et, n-Pr or i-Pr.

In one embodiment, with respect to a compound of the invention according to Formula Ia or Ib, each of W, W', Y, and Y' is independently $CR^{2a}$.

In one embodiment, with respect to a compound of the invention according to Formula Ia or Ib, one of W, W', Y, and Y' is N and the rest are independently $CR^{2a}$.

In one embodiment, with respect to a compound of the invention according to Formula Ia or Ib, two of W, W', Y, and Y' is N and the rest are independently $CR^{2a}$.

In one particular embodiment, with respect to a compound of the invention according to Formula Ia or Ib, each of W, W', Y, and Y' is independently CH.

In one embodiment, with respect to a compound of the invention according to Formula Ia or Ib, each of W, W', and Y is independently CH; and Y' is N.

In one embodiment, with respect to s compound of the invention according to Formula Ia or Ib, each of W, and W' is independently CH; and each of Y and Y' is N.

In one embodiment, with respect to a compound of the invention according to Formula Ia, the compound is according to Formula IIa, IIb, IIc, or IId:

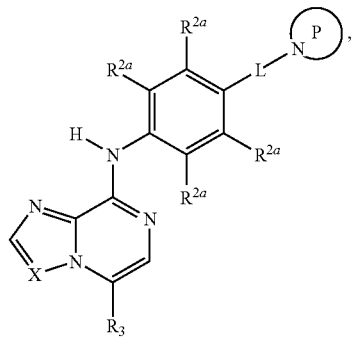

IIa

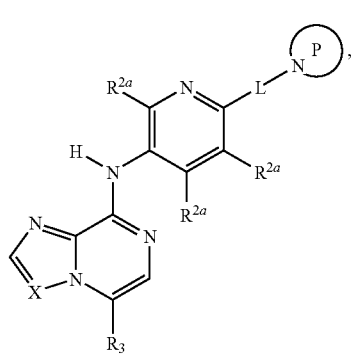

IIb

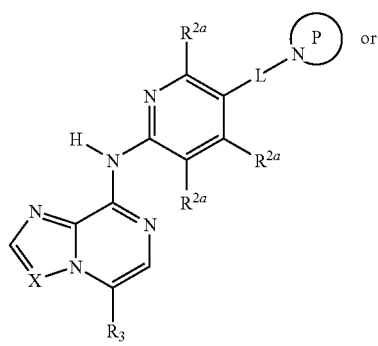

IIc or

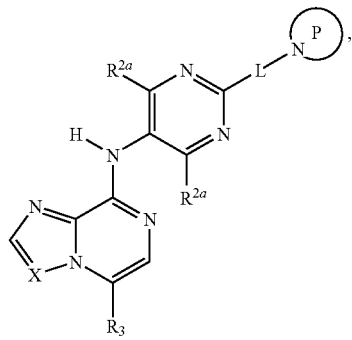

IId wherein X, L and the ring P are as defined for Formula Ia; each $R^{2a}$ is independently selected from H, substituted or unsubstituted $C_1$-$C_6$ alkyl, substituted or unsubstituted $C_1$-$C_6$ alkoxy, cyano, and halo; and $R^3$ is independently selected from substituted or unsubstituted aryl and substituted or unsubstituted heteroaryl.

In a further embodiment, with respect to a compound of the invention according to Formula Ib, the compound is according to Formula IIe, IIf, or IIg:

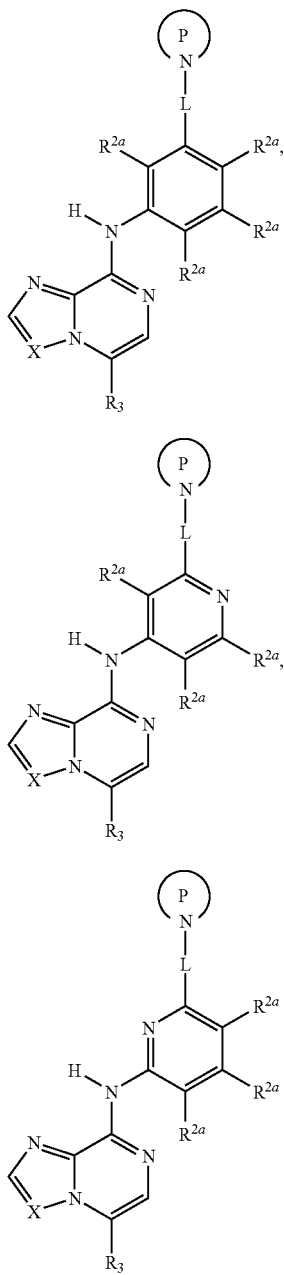

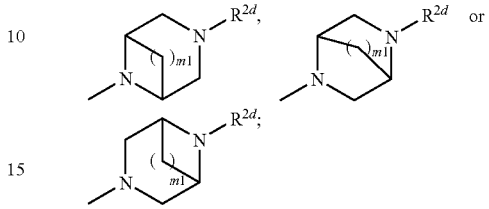

wherein L and the ring P are defined for Formula Ib; each $R^{2a}$ is independently selected from H, substituted or unsubstituted $C_1$-$C_6$ alkyl, substituted or unsubstituted $C_1$-$C_6$ alkoxy, cyano, and halo; and $R^3$ is independently selected from substituted or unsubstituted aryl and substituted or unsubstituted heteroaryl.

In one embodiment, with respect to a compound of the invention according to any one of Formulae Ia-IIg, each $R^{2a}$ is H.

In one embodiment, with respect to a compound of the invention according to any one of Formulae I-IIg, each $R^{2a}$ is selected from Me, Et, Pr, iso-Pr, Cl, F, CN, OMe, and $CF_3$.

In one embodiment, with respect to a compound of the invention according to any one of Formulae Ia-IIg, L is a single bond.

In one embodiment, with respect to a compound of the invention according to any one of Formulae Ia-IIg, L is —CO— or —NHCO—.

In one embodiment, with respect to a compound of the invention according to any one of Formulae Ia-IIg, the ring P is substituted or unsubstituted:

and wherein $R^{2d}$ and m1 are as defined for formula I.

In one embodiment, with respect to a compound of the invention according to any one of Formulae Ia-IIg, $R^{2a}$ is H, unsubstituted $C_1$-$C_6$ alkyl, unsubstituted $C_1$-$C_6$ haloalkyl, unsubstituted $C_1$-$C_6$ alkoxy, cyano, or halo.

In another further embodiment, with respect to a compound of the invention according to any one of Formulae Ia-IIg, one $R^{2a}$ is selected from Me, Et, Pr, iso-Pr, Cl, F, CN, OMe, and $CF_3$, and the rest are H.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is selected from substituted or unsubstituted aryl.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is phenyl optionally substituted with halo, cyano, unsubstituted $C_1$-$C_6$ alkoxy or amido optionally substituted with unsubstituted $C_1$-$C_6$ alkyl.

In a further embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is phenyl optionally substituted with F, Cl, Br, cyano, OMe, OEt, On-Pr, Oi-Pr or amido optionally substituted with Me, Et, n-Pr, or i-Pr.

In another embodiment, with respect to a compound of the invention according to any onf of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is selected from substituted or unsubstituted heteroaryl.

In further embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is selected from phenyl, pyridyl, indolyl, isoindolyl, pyrrolyl, furanyl, thienyl, pyrazolyl, oxazolyl, and thiazolyl, each of which may be unsubstituted or substituted with hydroxyl, cyano, halo, or amido optionally substituted with unsubstituted $C_1$-$C_6$ alkyl.

In another further embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is selected from phenyl, pyridyl, indolyl, isoindolyl, pyrrolyl, furanyl, thienyl, pyrazolyl, oxazolyl, and thiazolyl, each of which may be unsubstituted or substituted with hydroxyl, cyano, F, Cl, Br, or amido optionally substituted with Me, Et, n-Pr, i-Pr.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

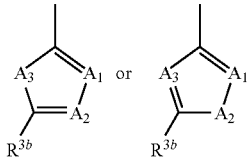

and each of $A^1$, $A^2$ and $A^3$ is independently selected from S, O, N, $NR^{3a}$, and $CR^{3a}$; each of $R^{3a}$ is independently H or substituted or unsubstituted $C_1$-$C_6$ alkyl; and $R^{3b}$ is $CONH_2$, CONHMe, or CN.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

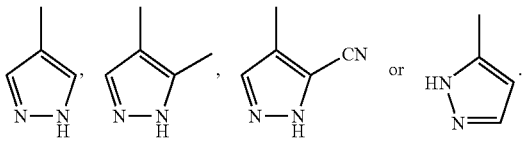

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

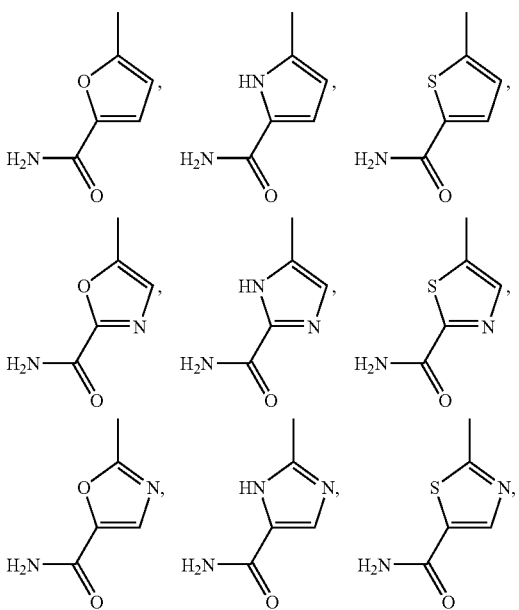

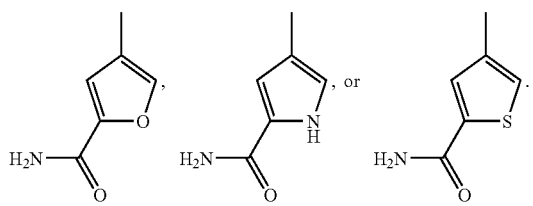

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is selected from

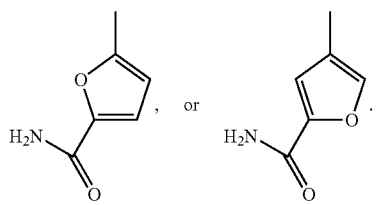

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

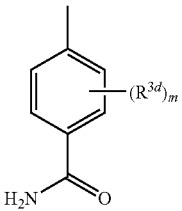

and wherein the subscript m is selected from 0, 1, 2, 3, and 4 and each $R^{3d}$ is independently substituted or unsubstituted $C_1$-$C_6$ alkyl or halo.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

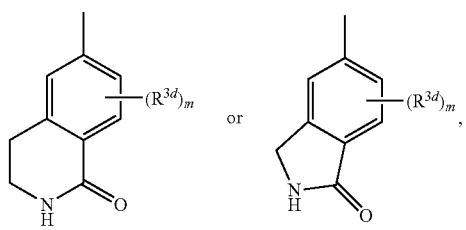

and wherein the subscript m is selected from 0, 1, 2, 3, and 4 and each $R^{3d}$ is independently substituted or unsubstituted $C_1$-$C_6$ alkyl or halo.

In one embodiment, with respect to a compound of the invention according to any one of Formulae Ia-IIg, each of W, W', Y, and Y', X, L, the ring P, $R^1$, $R^{2a}$, $R^{2c}$ and $R^{2d}$ are described in any one of the preceding paragraphs, and $R^3$ is

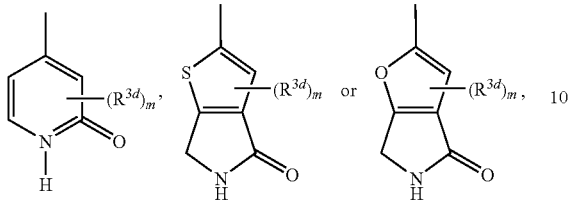

and wherein the subscript m is selected from 0, 1, 2, or 3 and each $R^{3d}$ is independently substituted or unsubstituted $C_1$-$C_6$ alkyl or halo.

In one embodiment, with respect to a compound of the invention according to any one of Formulae Ia-IIg, each of W, W', Y, and Y', X, L, the ring P, $R^1$, $R^{2a}$, $R^{2c}$, $R^{2d}$ and $R^3$ are as described in any one of the preceding paragraphs; m is 1 or 2; and each $R^{3d}$ is Me, Cl or F.

In certain embodiments, with respect to a compound of the invention according to any one of Formulae Ia-IIg, each of W, W', Y, and Y', X, L, the ring P, $R^1$, $R^{2a}$, $R^{2c}$, $R^{2d}$ and $R^3$ are as described in any one of the preceding paragraphs and $R^{3a}$ is $C_1$-$C_6$ alkyl. In another embodiment, $R^{3a}$ is $C_1$-$C_4$ alkyl.

In certain embodiments, with respect to a compound of the invention according to any one of Formulae Ia-IIg, each of W, W', Y, and Y', X, L, the ring P, $R^1$, $R^{2a}$, $R^{2c}$, $R^{2d}$ and $R^3$ are as described in any one of the preceding paragraphs and $R^{3d}$ is $C_1$-$C_6$ alkyl. In another embodiment, $R^{3d}$ is $C_1$-$C_4$ alkyl.

In one embodiment, a $C_1$-$C_6$ alkyl group is optionally substituted by one or more groups (such as 1 to 3 substituents, in particular 1 substituent group) independently selected from halo, cyano, nitro, trifluoromethyl, trifluoromethoxy, azido, —$NR^{10}SO_2R^9$, —$SO_2NR^9R^{10}$, —$C(O)R^9$, —$C(O)OR^9$, —$OC(O)R^9$, —$NR^{10}C(O)R^9$, —$C(O)NR^9R^{10}$, —$NR^9R^{10}$, —$(CR^{10}R^{11})_mOR^{10}$ and wherein m is an integer from 1 to 5.

In one embodiment, each $R^9$ is independently selected from H, $C_1$-$C_8$ alkyl, —$(CH_2)_t(C_6$-$C_{10}$ aryl), —$(CH_2)_t(C_5$-$C_{10}$ heteroaryl), —$(CH_2)_t(C_3$-$C_{10}$ cycloalkyl), and —$(CH_2)_t(C_5$-$C_{10}$ heterocycloalkyl) wherein t is an integer from 0 to 4.

In one embodiment, each $R^9$ is as described above and the $C_1$-$C_6$ alkyl group may optionally be substituted by halo and optionally contains 1 or 2 hetero moieties selected from O, S and —$N(R^{12})$— with the proviso that two O atoms, two S atoms, or an O and S atom are not attached directly to each other.

In one embodiment, each $R^9$ is as described above and any of which aryl, heteroaryl, cycloalkyl or heterocycloalkyl groups may themselves be substituted by $C_1$-$C_4$alkyl, halo, $C_1$-$C_4$alkoxy, $C_{1-4}$haloalkyl, $C_1$-$C_4$hydroxyalkyl or $C_1$-$C_4$ haloalkoxy or hydroxy.

In one embodiment, each $R^9$ is as described above and each of $R^{10}$ and $R^{11}$ independently represents H or $C_1$-$C_6$ alkyl;

In one embodiment, each $R^9$ is as described above and each of $R^{12}$ and $R^{13}$ independently represents H or $C_1$-$C_4$ alkyl;

In one embodiment, each of $R^{10}$ and $R^{11}$ independently represents H or $C_1$-$C_6$ alkyl In one embodiment, each $R^9$ is other than H.

In certain embodiments, with respect to a compound of the invention according to any one of Formulae Ia-IIg, $R^{2a}$ is $C_1$-$C_6$ alkoxy; and the alkoxy group is —$OR^9$; and $R^9$ is as described in any one of the above embodiments; provided that $R^9$ is other than H.

In one embodiment, with respect to a compound of the invention according to Formula Ia, the compound is according to formula IIIa, IIIb, or IIIc:

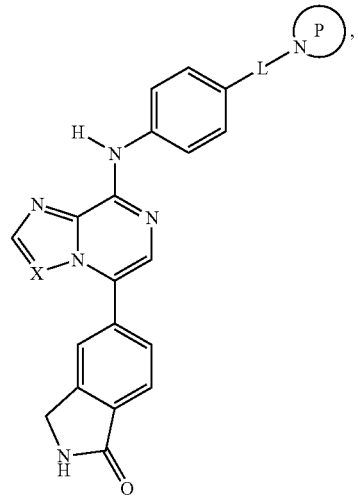

IIIa

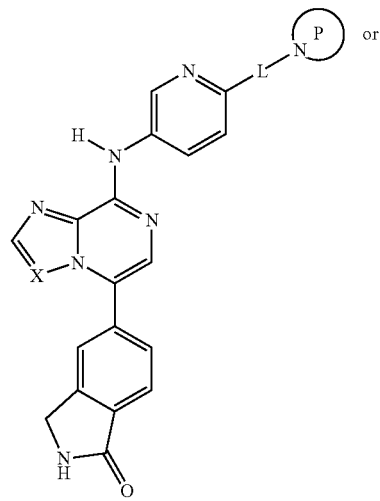

IIIb or

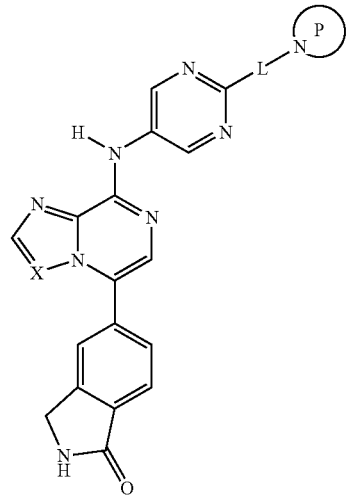

IIIc and X is CH or N; L is a single bond, —CO—, or —NHCO—; the ring P is

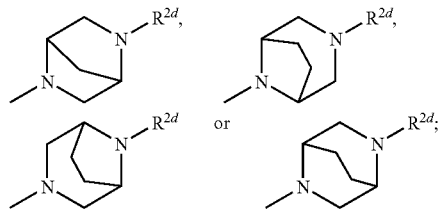

and $R^{2d}$ is H, $C_3$-$C_8$ cycloalkyl, or $C_1$-$C_6$ alkyl optionally substituted with halo, amido, or $C_3$-$C_8$ cycloalkyl.

In a further embodiment, with respect to a compound of the invention according to Formula Ib, the compound is according to Formula IIId, or IIIe:

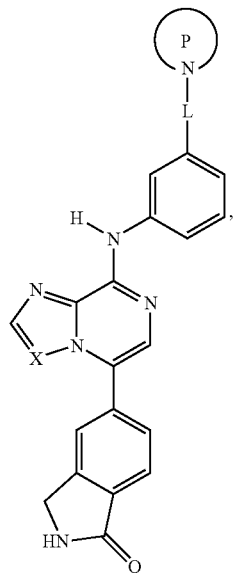

IIId

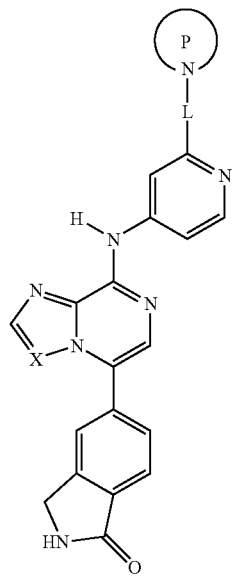

IIIe and X is CH or N; L is a single bond, —CO—, or —NHCO—; the ring P is

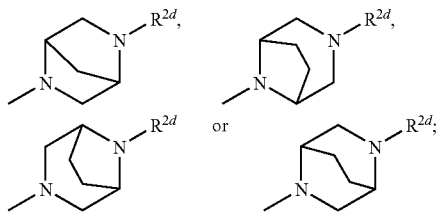

and $R^{2d}$ is H, $C_3$-$C_8$ cycloalkyl, or $C_1$-$C_6$ alkyl optionally substituted with halo, amido, or $C_3$-$C_8$ cycloalkyl.

In one particular embodiment, with respect to a compound of the invention according to any one of Formula IIIa-IIIe, L is a single bond.

In one embodiment, with respect to a compound of the invention according to Formula Ia, the compound is according to Formula IVa, IVb, or IVc:

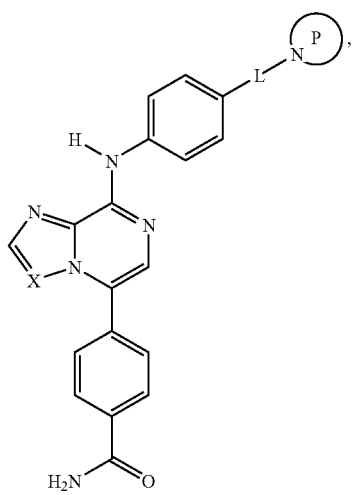

IVa

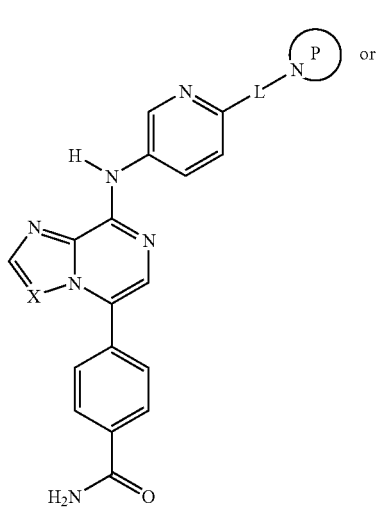

IVb

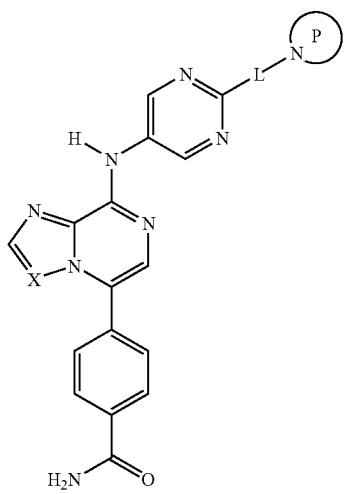

IVc and X is CH or N; L is a single bond, —CO—, or —NHCO—; the ring P is

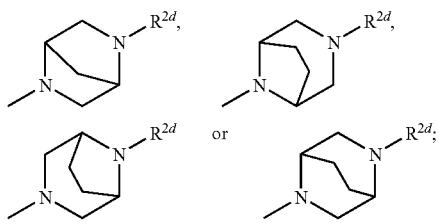

and $R^{2d}$ is H, $C_3$-$C_8$ cycloalkyl, or $C_1$-$C_6$ alkyl optionally substituted with halo, amido, or $C_3$-$C_8$ cycloalkyl.

In one embodiment, with respect to a compound of the invention according to Formula Ib, the compound is according to Formula IVd, or IVe:

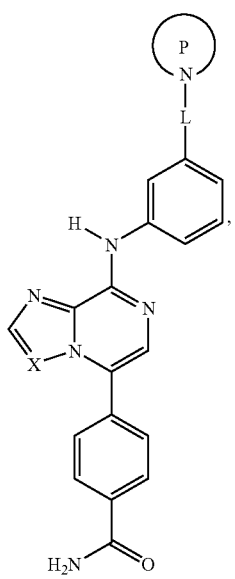

IVd

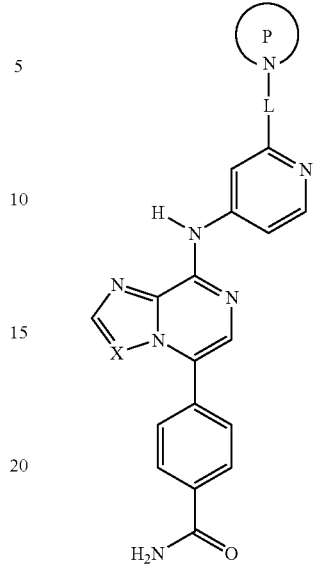

IVe and X is as in claim 1; L is a single bond, —CO—, or —NHCO—; the ring P is

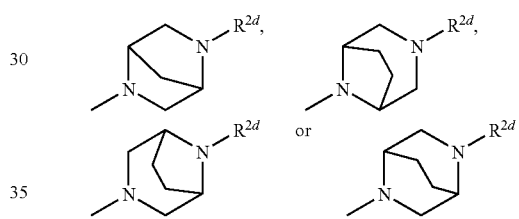

and $R^{2d}$ is H, $C_3$-$C_8$ cycloalkyl, or $C_1$-$C_6$ alkyl optionally substituted with halo, amido, or $C_3$-$C_8$ cycloalkyl.

In one particular embodiment, with respect to a compound of the invention according to Formula IVa-IVe, L is a single bond.

In one embodiment, with respect to a compound of the invention according to Formula Ia, the compound is according to Formula Va, Vb, or Vc:

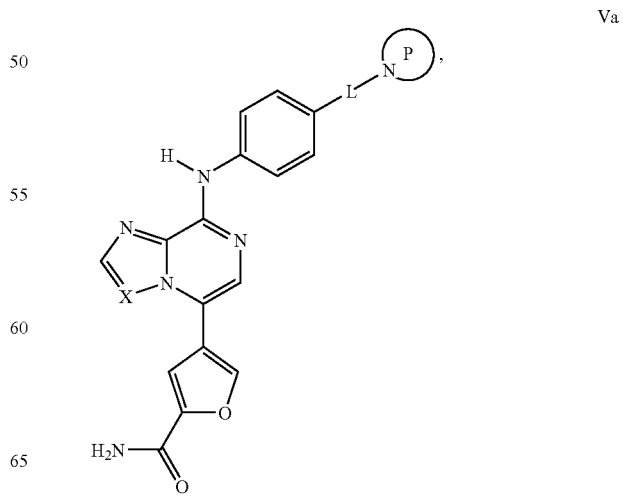

Va

-continued

Vb

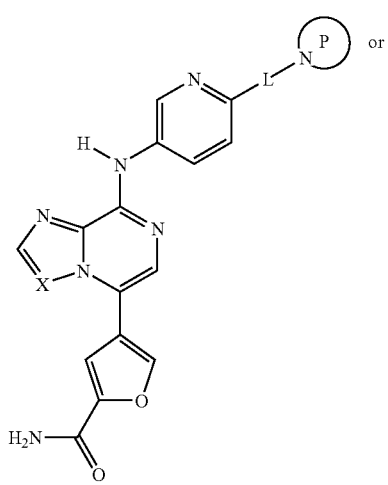

Vc

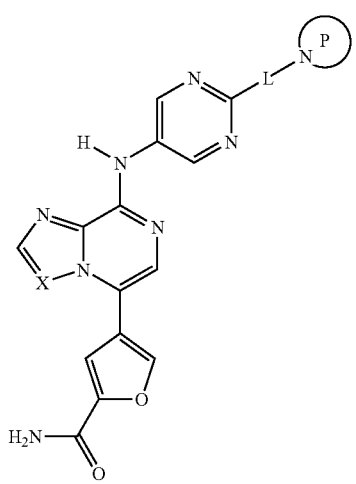

and X is CH or N; L is a single bond, —CO—, or —NHCO—; the ring P is

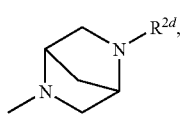 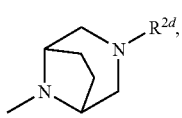

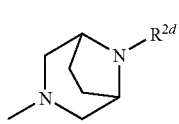 or 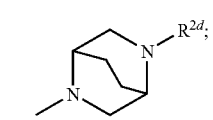

and $R^{2d}$ is $R^{2d}$ is H, $C_3$-$C_8$ cycloalkyl, or $C_1$-$C_6$ alkyl optionally substituted with halo, amido, or $C_3$-$C_8$ cycloalkyl.

In one embodiment, with respect to a compound of the invention according to Formula Ib, the compound is according to Formula Vd, or Ve:

Vd

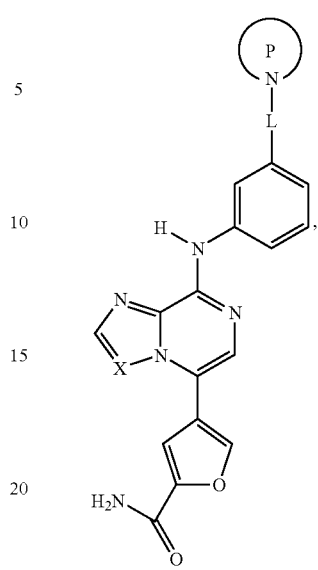

Ve

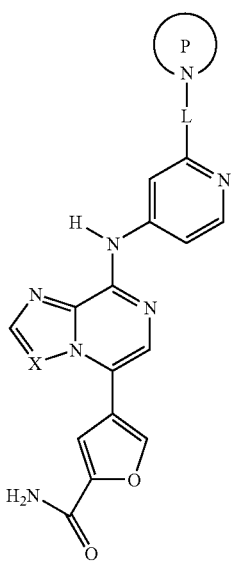

and X is CH or N; L is a single bond, —CO—, or —NHCO—; the ring P is

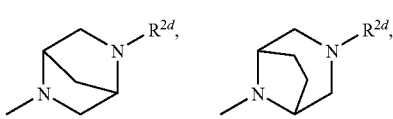 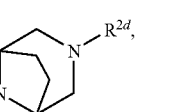

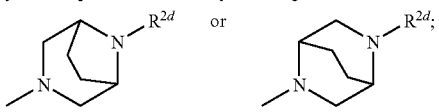 or 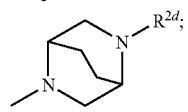

and $R^{2d}$ is $R^{2d}$ is H, $C_3$-$C_8$ cycloalkyl, or $C_1$-$C_6$ alkyl optionally substituted with halo, amido, or $C_3$-$C_8$ cycloalkyl.

In one particular embodiment, with respect to a compound of the invention according to any one of Formula Va-Ve, L is a single bond.

In one embodiment, with respect to a compound of the invention according to Formula Ia, the compound is according to Formula VIa, VIb, or VIc:

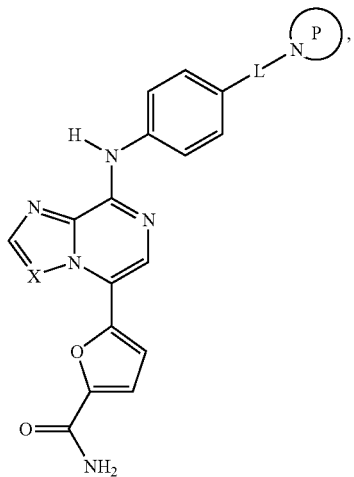
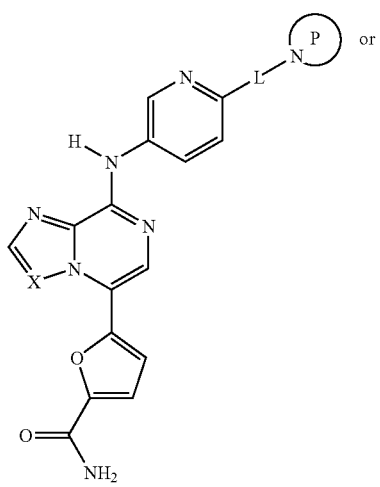
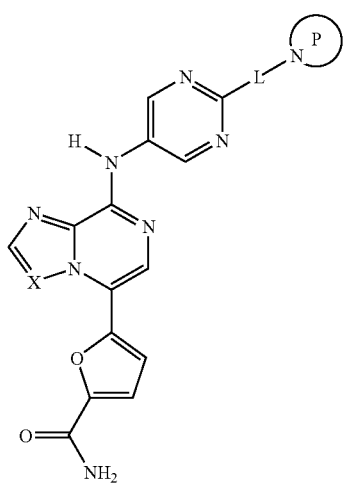
and X is CH or N; L is a single bond, —CO—, or —NHCO—; the ring P is
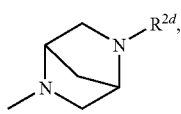 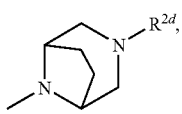
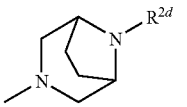 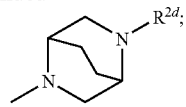
and $R^{2d}$ is $R^{2d}$ is H, $C_3$-$C_8$ cycloalkyl, or $C_1$-$C_6$ alkyl optionally substituted with halo, amido, or $C_3$-$C_8$ cycloalkyl.
In one embodiment, with respect to a compound of the invention according to Formula Ib, the compound is according to Formula VId, or VIe:
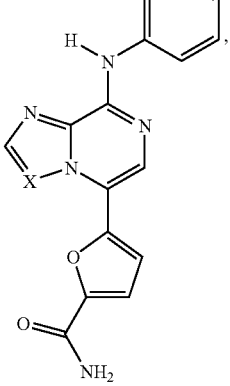
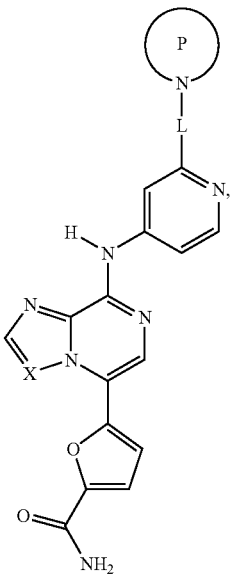
and X is CH or N; L is a single bond, —CO—, or —NHCO—; the ring P is
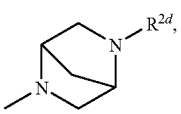 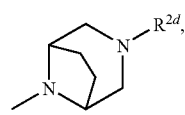

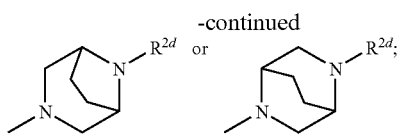

and $R^{2d}$ is $R^{2d}$ is H, $C_3$-$C_8$ cycloalkyl, or $C_1$-$C_6$ alkyl optionally substituted with halo, amido, or $C_3$-$C_8$ cycloalkyl.

In one particular embodiment, with respect to a compound of the invention according to any one of Formula VIa-VIe, L is a single bond.

In one embodiment, with respect to a compound of the invention according to any one of Formula Ia-VIe, L is a single bond.

In one embodiment, with respect to a compound of the invention according to any one of Formula Ia-VIe, L is —CO—.

In one embodiment, with respect to a compound of the invention according to any one of Formula Ia-VIe, L is —NHCO—.

In one embodiment, with respect to a compound of the invention according to any one of Formula Ia-VIe, $R^{2d}$ is H, Me, Et, i-Pr, t-Bu, cyclopropylmethyl or $CH_2CF_3$.

In one embodiment, with respect to a compound of the invention according to any one of Formula I-VIe, $R^{2d}$ is H, Me, i-Pr, t-Bu, $CH_2CONH_2$, cyclopropylmethyl, or $CH_2CF_3$.

In one embodiment, with respect to a compound of the invention according to any one of Formula Ia-VIe, $R^{2d}$ is H.

In one embodiment, with respect to a compound of the invention according to any one of Formula Ia-VIe, $R^{2d}$ is i-Pr.

In one embodiment, with respect to a compound of the invention according to any one of Formula Ia-VIe, $R^{2d}$ is t-Bu.

In one embodiment, with respect to a compound of the invention according to any one of Formula Ia-VIe, $R^{2d}$ is cyclopropylmethyl.

In one embodiment, with respect to a compound of the invention according to any one of Formula Ia-VIe, the ring P is

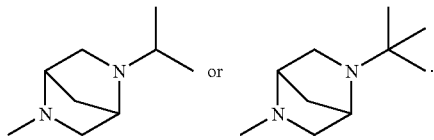

In one embodiment, with respect to a compound of the invention according to any one of Formula Ia-VIe, the ring P is

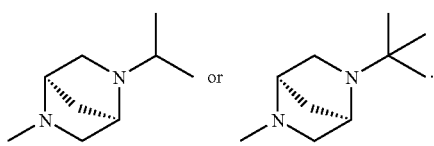

In one embodiment, with respect to a compound of the invention according to any one of Formula Ia-VIe, the ring P is

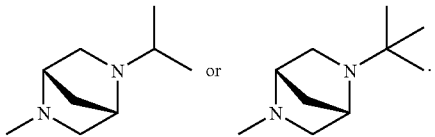

In one embodiment, with respect to a compound of the invention according to any one of Formula Ia-VIe, X is CH.

In one embodiment, with respect to a compound of the invention according to any one of Formula Ia-VIe, X is N.

In one embodiment, with respect to a compound of the invention according to Formula Ia or Ib, the compound is selected from the compounds listed in Table 1.

In one embodiment, with respect to a compound of the invention according to Formula Ia, the compound is selected from:

- 5-(8-(4-((1S,4S)-5-isopropyl-2,5-diazabicyclo[2.2.1]heptan-2-yl)phenylamino)-[1,2,4]triazolo[1,5-a]pyrazin-5-yl)isoindolin-1-one;
- 4-(8-(4-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide;
- 4-(8-(4-((1S,4R)-5-tert-butyl-2,5-diazabicyclo[2.2.1]heptan-2-yl)phenylamino)-[1,2,4]triazolo[1,5-a]pyrazin-5-yl)furan-2-carboxamide;
- 4-(8-(4-((1S,4S)-5-isopropyl-2,5-diazabicyclo[2.2.1]heptan-2-yl)phenylamino)imidazo[1,2-a]pyrazin-5-yl)furan-2-carboxamide;
- 5-{8-(4-((1S,4S)-5-isopropyl-2,5-diazabicyclo[2.2.1]heptan-2-yl)phenyl-amino)-[1,2,4]triazolo[1,5-a]pyrazin-5-yl}-1H-pyrazole-3-carboxylic acid amide;
- 4-{8-(4-((1S,4S)-5-tert-butyl-2,5-diazabicyclo[2.2.1]heptan-2-yl)-phenyl-amino)imidazo[1,2-a]pyrazin-5-yl}-furan-2-carboxylic acid amide;
- 4-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-furan-2-carboxylic acid amide;
- 4-{8-(4-((1S,4S)-5-isopropyl-2,5-diazabicyclo[2.2.1]heptan-2-yl)phenyl-amino)imidazo[1,2-a]pyrazin-5-yl}-1H-pyridin-2-one;
- 4-{8-(4-(5-isopropyl-2,5-diazabicyclo[2.2.2]octan-2-yl)phenylamino)[1,2,4]-triazolo[1,5-a]pyrazin-5-yl}-furan-2-carboxylic acid amide;
- 4-{8-(4-(5-isopropyl-2,5-diazabicyclo[2.2.2]octan-2-yl)phenylamino)-imidazo[1,2-a]pyrazin-5-yl}-furan-2-carboxylic acid amide;
- 4-{8-(4-(3-isopropyl-3,8-diazabicyclo[3.2.1]octan-8-yl)phenylamino)-imidazo[1,2-a]pyrazin-5-yl}-furan-2-carboxylic acid amide;
- 4-{8-(4-(8-isopropyl-3,8-diazabicyclo[3.2.1]octan-3-yl)phenylamino)[1,2,4]-triazolo[1,5-a]pyrazin-5-yl}-furan-2-carboxylic acid amide;
- 4-{8-(4-(3-isopropyl-3,8-diazabicyclo[3.2.1]octan-8-yl)phenylamino)[1,2,4]-triazolo[1,5-a]pyrazin-5-yl}-furan-2-carboxylic acid amide;
- 4-{8-(4-(8-isopropyl-3,8-diazabicyclo[3.2.1]octan-3-yl)phenylamino)-imidazo[1,2-a]pyrazin-5-yl}-furan-2-carboxylic acid amide;
- 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-1H-pyrazole-3-carboxylic acid amide;
- 5-{8-(4-((1S,4S)-5-tert-butyl-2,5-diazabicyclo[2.2.1]heptan-2-yl)phenylamino)-[1,2,4]triazolo-[1,5-a]pyrazin-5-yl}-2,3-dihydro-isoindol-1-one;

5-{8-(4-((1S,4S)-5-tert-butyl-2,5-diazabicyclo[2.2.1]heptan-2-yl)phenyl-amino)-[1,2,4]triazolo[1,5-a]pyrazin-5-yl}-1H-pyrazole-3-carboxylic acid amide; and 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-2,3-dihydro-isoindol-1-one.

In another embodiment, with respect to a compound of the invention according to Formula Ib, the compound is selected from:

4-(8-(3-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide;

4-(8-(3-((1S,4S)-5-isopropyl-2,5-diazabicyclo[2.2.1]heptan-2-yl)phenylamino)imidazo[1,2-a]pyrazin-5-yl)furan-2-carboxamide;

5-(8-(3-((1S,4S)-5-isopropyl-2,5-diazabicyclo[2.2.1]heptan-2-yl)phenylamino)-[1,2,4]triazolo[1,5-a]pyrazin-5-yl)isoindolin-1-one.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound of the invention.

In one aspect a compound of the invention according to any one of the embodiments herein described is a solvate of a pharmaceutically acceptable salt of a compound of the invention.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

In certain aspects, the present invention provides prodrugs and derivatives of the compounds of the invention according to the formulae above. Prodrugs are derivatives of the compounds of the invention, which have metabolically cleavable groups and become by solvolysis or under physiological conditions the compounds of the invention, which are pharmaceutically active, in vivo. A prodrug may be inactive when administered to a subject but is converted in vivo to an active compound of the invention. "Pharmaceutically acceptable prodrugs" as used herein refers to those prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term 'prodrug' means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Design of Prodrugs, H. Bundgard, ed., Elsevier (1985); Methods in Enzymology; K. Widder et al, Ed., Academic Press, 42, 309-396 (1985); A Textbook of Drug Design and Development, Krogsgaard-Larsen and H. Bundgard, ed., Chapter 5; "Design and Applications of Prodrugs" 113-191 (1991); Advanced Drug Delivery Reviews, H. Bundgard, 8, 1-38, (1992); J. Pharm. Sci., 77,285 (1988); Chem. Pharm. Bull., N. Nakeya et al, 32, 692 (1984); Prodrugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference. Such examples include, but are not limited to, choline ester derivatives and the like, N-alkylmorpholine esters and the like.

Other derivatives of the compounds of the invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as pharmaceuticals, a compound of the invention is typically administered in the form of a pharmaceutical composition. Such compositions can be prepared in a manner well known in the pharmaceutical art and comprise at least one active compound.

Generally, a compound of the invention is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention may be dissolved or suspended in a buffered sterile saline injectable aqueous medium to a concentration of approximately 5 mg/ml.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture would be stirred until it congeals.

METHODS OF TREATMENT

A compound of the invention may be used as a therapeutic agent for the treatment of conditions in mammals that are causally related or attributable to aberrant activity of MMP1 and/or MAPKAPK5. Accordingly, the compounds of the invention and pharmaceutical compositions thereof find use as therapeutics for preventing and/or treating inflammatory diseases in mammals including humans. Thus, and as stated earlier, the present invention includes within its scope, and extends to, the recited methods of treatment, as well as to the compounds for use in such methods, and for the preparation of medicaments useful for such methods.

In a method of treatment aspect, this invention provides a method of treating a mammal susceptible to or afflicted with a condition associated with extra-cellular matrix (ECM) degradation, in particular arthritis, and more particularly, rheumatoid arthritis which method comprises administering an effective amount of a compound of the invention or a pharmaceutical composition thereof.

In another method of treatment aspect, the invention provides a method of treating a mammal sucepible to or afflicted with a condition associated with an abnormal cellular expression of MMP1, which comprises administering a therapeutically effective amount of a compound of the invention, or a pharmaceutical composition thereof.

In another method of treatment aspect, the present invention provides a method of treatment or prophylaxis of a condition characterized by abnormal matrix metallo proteinase activity, which comprises administering a therapeutically effective matrix metallo proteinase inhibiting amount of a compound of the invention, or pharmaceutical composition thereof.

In yet another method of treatment aspect, this invention provides methods of treating a mammal susceptible to or afflicted with diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; and renal disorders method comprises administering an effective condition-treating or condition-preventing amount of a compound of the invention or pharmaceutical compositions thereof.

This invention also relates to the use of a compound of the invention in the manufacture of a medicament for treatment or prophylaxis of a condition prevented, ameliorated or eliminated by administration of an inhibitor of Mitogen-Activated Protein Kinase-Activated Protein Kinase 5, or a condition characterised by abnormal collagenase activity, or a condition associated with ECM degradation or a condition selected from diseases involving inflammation, most preferably in for the treatment of rheumatoid arthritis.

As a further aspect of the invention there is provided a compound of the invention for use as a pharmaceutical especially in the treatment or prevention of the aforementioned conditions and diseases. Also provided herein is the use of a compound of the invention in the manufacture of a medicament for the treatment or prevention of one of the aforementioned conditions and diseases.

In a further aspect the present invention provides a compound of the invention for use in the prevention or treatment of conditions in mammals that are causally related or attributable to aberrant activity of MMP1 and/or MAPKAPK5. In particular, the present invention provides a compound of the invention and/or pharmaceutical compositions thereof for use in the treatment or prevention of inflammatory diseases in mammals including humans.

In a further aspect, this invention provides a compound of the invention for use in the prevention or treatment of a condition associated with extra-cellular matrix (ECM) degradation, in particular arthritis, and more particularly, rheumatoid arthritis.

In a further aspect, this invention provides a compound of the invention for use in the prevention or treatment of a condition associated with an abnormal cellular expression of MMP1.

In a further aspect, this invention provides a compound of the invention for use in the prevention or treatment of a condition characterized by abnormal matrix metallo proteinase activity.

In a further aspect, this invention provides a compound of the invention for use in the prevention or treatment of diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; and renal disorders.

A preferred regimen of the present method comprises the administration to a subject in suffering from a disease condition characterized by extracellular matrix degradation, with an effective matrix metallo-protease inhibiting amount of a compound of the invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

The compounds of the invention may show less toxicity, good absorption, good half-life, good solubility, low protein binding affinity, less drug-drug interaction, and good metabolic stability. In a particular aspect, a compound of the invention exhibits unexpected significant improvements in pharmacological properties, in particular improved efficacy and improved tolerability. Where the compounds exhibit any one or more of these improvements, this may have an effect on their use in the conditions described herein. For example, where the compounds exhibit an improved efficacy it would be expected that the compounds could be administered at a lower dose, thus reducing the occurrence of any possible undesired side effects. Similarly, where the compounds exhibit increased tolerability, this might allow the compounds to be dosed at a higher concentration without causing unwanted side effects. Such alterations in efficacy or tolerability might be expected to result in an improved therapeutic window for said compounds of the invention. Similarly, improvements in the other properties listed above will also confer advantages in the potential uses of the compounds.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as inflammatory and autoimmune conditions, the regimen for treatment usually extends over many months or years, and accordingly oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of an inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compounds that demonstrate the same or a similar therapeutic activity, and that are determined to safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of a disease involving inflammation; particular agents include, but are not limited to, immunoregulatory agents e.g. azathioprine, corticosteroids, cyclophosphamide, cyclosporin A, FK506, Mycophenolate Mofetil, OKT-3 and ATG.

In one embodiment, a compound of the invention is co-administered with another therapeutic agent for the treatment and/or prevention of rheumatoid arthritis; particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and ciclosporin), and biological DMARDS (for example but without limitation Infliximab, Etanercept, Adalimumab, Rituximab, and Abatacept).

By co-administration is included any means of delivering two or more therapeutic- agents to the patient as part of the same treatment regime, as will be apparent to the skilled person. Whilst the two or more agents may be administered simultaneously in a single formulation this is not essential. The agents may be administered in different formulations and at different times.

GENERAL SYNTHETIC PROCEDURES

The triazolopyrazine and imidazopyrazine compounds of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative bicycloheteroaryls that have been listed hereinabove. The compounds of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm) $^1$H NMR spectra were recorded on a Bruker DPX 400 NMR spectrometer (400 MHz). Chemical shifts (δ) for $^1$H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), multiplet (m) and broad (br). Coupling constants (J) are given in Hz. Electrospray MS spectra were obtained on a Micromass platform LC/MS spectrometer. Column Used for all LCMS analysis: Waters Acquity UPLC BEH C18 1.7 μm, 2.1 mm ID×50 mm L (Part No.186002350)). Preparative HPLC: Waters XBridge Prep C18 5 μm ODB 19 mm ID×100 mm L (Part No.186002978). All the methods are using MeCN/H$_2$O gradients. H$_2$O contains either 0.1% TFA or 0.1% NH$_3$.

| List of abbreviations used in the experimental section | |
|---|---|
| DCM: | Dichloromethane |
| DiPEA: | N,N-diisopropylethylamine |
| MeCN | Acetonitrile |
| BOC | tert-Butyloxy-carbonyl |
| DMF | N,N-dimethylformamide |
| TFA | Trifluoroacetic acid |
| THF | Tetrahydrofuran |
| NMR | Nuclear Magnetic Resonnance |
| DMSO | Dimethylsulfoxide |
| DPPA | Diphenylphosphorylazide |
| LC-MS | Liquid Chromatography-Mass Spectrometry |
| Ppm | part-per-million |
| EtOAc | ethyl acetate |
| APCI | atmospheric pressure chemical ionization |
| Rt | retention time |
| s | singlet |
| br s | broad singlet |
| m | multiplet |
| d | doublet |
| PdCl$_2$dppf | [1,1'-Bis(diphenylphosphino)ferrocene]dichloropalladium (II) |
| TEA | Triethylamine |
| AIBN | 2,2'-azobisisobutyronitrile |
| IPA | Iso-Propyl Alcohol |
| BINAP | 2,2'-bis(diphenylphosphino)-1,1'-binaphthyl |
| MTBE | Methyl tert-Butyl Ether |
| 2-MeTHF | 2-Methyl Tetrahydrofuran |
| EDTA | Ethylenediaminetetraacetic acid |
| ATP | Adenosine triiphosphate |
| EGTA | Ethylene Glycol Tetraacetic Acid |
| BSA | Bovine Serum Albumine |
| DTT | Dithiothreitol |
| FBS | Fetal bovine serum |
| PBST | Phosphate buffered saline with Tween 3.2 mM Na2HPO4, 0.5 mM KH2PO4, 1.3 mM KCl, 135 mM NaCl, 0.05% Tween 20, pH 7.4 |
| MMP | Matrix Metallo Proteinase |
| shRNA | short hairpin RNA |
| RNA | Ribonucleic acid |
| Ad-Si RNA | Adenoviral encoded siRNA |
| DMEM | Dulbecco's Modified Eagle Medium |
| APMA | 4-aminophenylmercuric acetate |
| hCAR | human cellular adenovirus receptor |
| dNTP | deoxyribonucleoside triphosphate |
| QPCR | quantitative polymerase chain reaction |
| cDNA | copy deoxyribonucleic acid |
| GAPDH | Glyceraldehyde phosphate dehydrogenase |
| PVDF | Polyvinylidene Fluoride |
| RIPA buffer | Radioimmunoprecipitation assay buffer |

-continued

| List of abbreviations used in the experimental section | |
|---|---|
| MAPKAPK5 | Mitogen-activated protein kinase-activated protein kinase 5 |
| PBMC | Peripheral Blood Mononuclear Cell |
| TNFα | Tumor Necrosis Factor alpha |
| LPS | Lipopolysaccharide |
| ip | Intra-peritoneal |
| iv | Intraveinous |

Synthetic Preparation of Compounds of the Invention

Synthesis of Intermediates Synthesis of Intermediates
Intermediate 1a: Preparation of 3,6-Dibromo-pyrazin-2-ylamine
General reaction scheme:

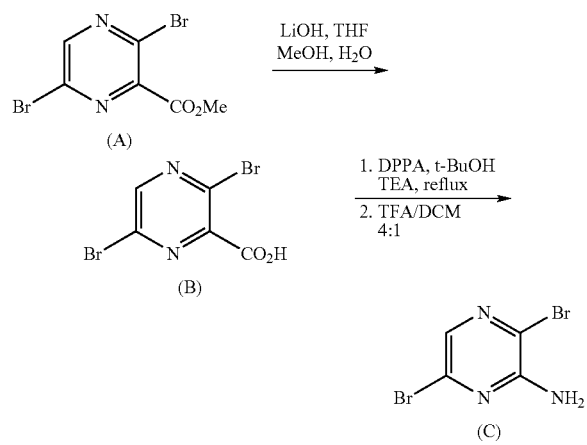

Step 1: Synthesis of compound (B) as described in the general reaction scheme; 3,6-dibromo-pyrazine-2-carboxylic acid.

LiOH (655 mg, 27 mmol) is added to a solution of 3,6-dibromo-pyrazine-2-carboxylic acid methyl ester (A) (*J. Med. Chem.* 1969, 12, 285-87) (2.7 g, 9 mmol) in THF:water:MeOH (18:4.5:4.5 mL). The reaction is stirred at 5° C. for 30 min, concentrated in vacuo, taken up in DCM and washed with 1N HCl. The organic phase is dried over anhydrous MgSO$_4$ and concentrated in vacuo to afford compound (B). $^1$H NMR (250 MHz, CDCl$_3$) δ (ppm) 8.70 (s, 1H).

Step 2: Synthesis of compound (C) as described in the general reaction scheme; 3,6-Dibromo-pyrazin-2-ylamine.

Diphenylphosphorylazide (2.59 mL, 12 mmol) and triethylamine (1.67 mL, 12 mmol) are added to a solution of 3,6-dibromo-pyrazin-2-carboxylic acid (3.52 g, 12 mmol) in t-butanol (90 mL). The reaction is heated at reflux for 18 hours. The reaction is quenched with water, then concentrated in vacuo and taken up in DCM. The organic solution is washed with water and 1N NaOH, dried over MgSO$_4$ and concentrated in vacuo. The resultant solid is filtered through a pad of silica using EtOAc, then concentrated and TFA:DCM (4:1, 12 mL) is added to the solid and stirred for 30 min. The solution is concentrated in vacuo then neutralised with 1N NaOH and extracted with DCM. The organic layer is dried over anhydrous MgSO$_4$ and concentrated in vacuo to give the product. $^1$H NMR (250 MHz, DMSO-d6) δ(ppm) 7.25 (br s, 2H), 7.68 (s, 1H); m/z (APCI) 254 (M+H)$^+$; m.p 135-139° C.
Intermediate 1b: Preparation of 3-Choro-6-bromo-pyrazin-2-yl-amine Alternatively 3-chloro-6-bromopyrazin-2-yl-amine can be used in place of 3,6-dibromo-pyrazin-2-yl amine and is prepared according to the following scheme:

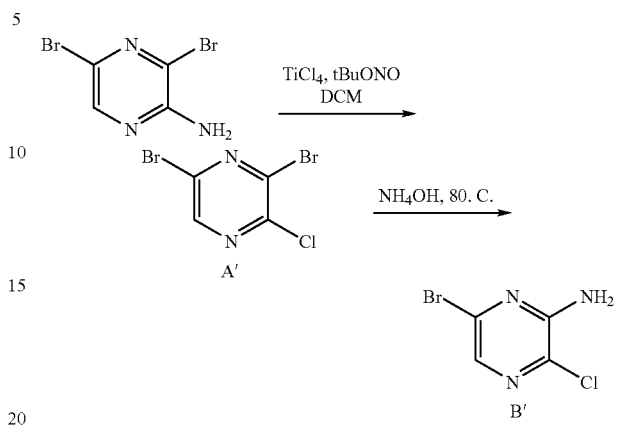

Step 1: Synthesis of compound (A') as described in the general reaction scheme; 2-chloro-3,5-dibromo-pyrazine To a well stirred solution of 2-amino-3,5-dibromopyrazine (3.21 g, 12.692 mmol) in DCM (20 mL) cooled to 0° C. is added TiCl$_4$ (2.41 g, 12.692 mmol, 1.00 equiv.) in one portion, thus giving a dark red slurry. t-Butylnitrite (2.62 g, 25.385 mmol, 2.00 equiv.) is then added dropwise, causing the solution to turn bright yellow. The ice bath is then removed and the reaction is then allowed to proceed at room temperature. More TiCl$_4$ (1.50 g, 1.2 equiv.) is added and the mixture is stirred further for one hour. At that point an orange solution has formed and LC-MS shows full conversion of the starting material to the desired product which ionises very poorly. Water (100 mL) is added to the reaction, forming an emulsion. DCM (50 mL) is added, and the DCM layer is separated, and the aqueous layer is further extracted with DCM (3×50 mL) until the DCM layer is colorless. The DCM layers are gathered, washed with brine and dried over anhydrous Na$_2$SO$_4$, to yield after solvent removal, compound A' (2.81 g, 82%) as an orange oil, which is used as such in the following step.

Step 2: Synthesis of compound (B') as described in the general reaction scheme; 3-chloro-6-bromopyrazin-2-yl amine Compound A' described in the previous step (9.5 g, 37.55 mmol) is suspended in concentrated NH$_4$OH (60 mL) and the resulting mixture is heated in a pressure autoclave to 80° C., typically overnight. The vessel is then allowed to cool down to room temperature slowly, and is then further cooled in an ice bath, causing the precipitation of the desired material. The solid is separated by filtration, washed with cyclohexane, to afford after drying, the title compound B' (5 g) as a 83/17 mixture of regiosiomers. The mxiture is then purified by column chromatography. M+H+, m/z=209

Intermediate 2: 5,8-Dibromo-imidazo[1,2-a]pyrazine

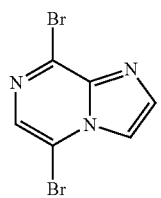

Bromoacetaldehyde diethyl acetal (49 mL, 326 mmol) and 48% hydrobromic acid is heated to reflux for 1.5 h, then poured into propan-2-ol (600 mL) and quenched with NaHCO$_3$. After filtering, 3,6-dibromopyrazin-2-yl amine (41.34 g, 163 mmol) is added to the solution and heated at reflux overnight. The reaction is cooled and solvents removed in vacuo, followed by addition of aq. NaHCO$_3$ and extraction with EtOAc. The organic phase is dried over anhydrous MgSO$_4$, filtered, and concentrated in vacuo to afford a brown solid. $^1$H NMR (250 MHz, CDCl$_3$) δ(ppm) 7.86 (s, 1H), 7.93-7.94 (d, 1H), 7.98-7.99 (d, 1H); m/z (APCI) 278 (M+H)$^+$; m.p 132-135° C.

Intermediate 3: 5,8-Dibromo-[1,2,4]triazolo[1,5-a]pyrazine

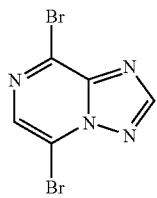

General scheme:

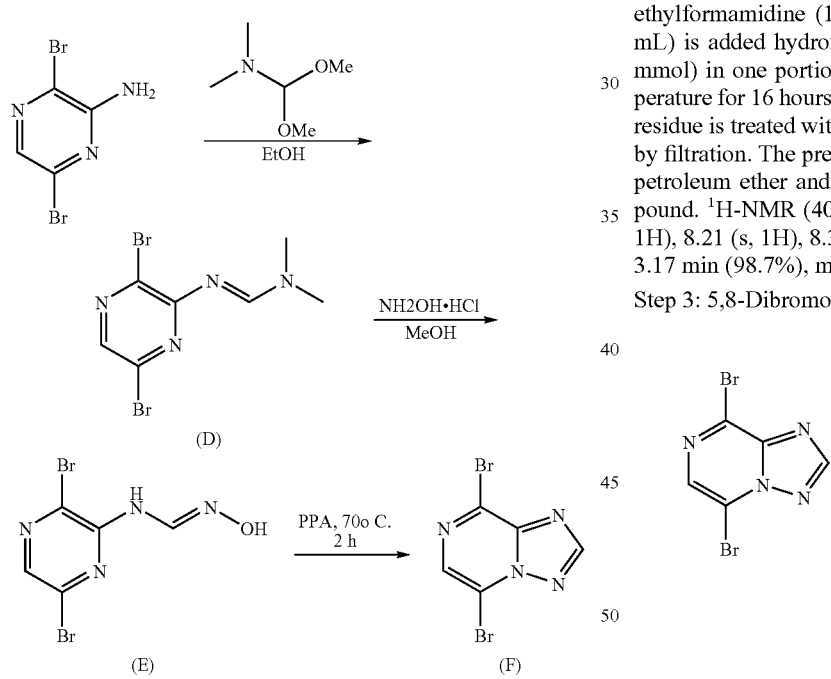

Step 1: N'-(3,6-Dibromo-pyrazin-2-yl)-N,N-dimethylformamidine (D)

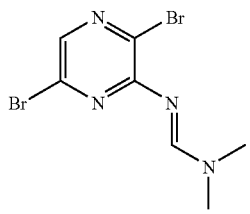

A mixture of 3,6-dibromo-pyrazin-2-ylamine (15.37 g, 60.80 mmol) and N,N-dimethylformamide dimethyl acetal (10.1 mL, 76.00 mmol), suspended in ethanol (150 mL), is refluxed for 2 hours. The reaction mixture is evaporated in vacuo affording the title compound. $^1$H-NMR (400 MHz, CDCl$_3$) δ(ppm) 3.20 (s, 3H), 3.21 (s, 3H), 7.93 (s, 1H), 8.48 (s, 1H). LCMS: Rt 3.81 min (99.1%), m/z (APCI) 307 (M+H)$^+$.

Step 2: N-(3,6-Dibromo-pyrazin-2-yl)-N'-hydroxyformamidine (E)

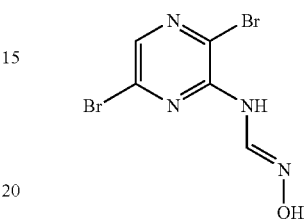

To a solution of N'-(3,6-dibromo-pyrazin-2-yl)-N,N-dimethylformamidine (18.6 g, 60.80 mmol) in methanol (200 mL) is added hydroxylamine hydrochloride (5.91 g, 85.12 mmol) in one portion. The reaction is stirred at room temperature for 16 hours. The solvent is evaporated and the solid residue is treated with cold (ice cooling) water and collected by filtration. The precipitate is washed twice with water and petroleum ether and dried in vacuo yielding the title compound. $^1$H-NMR (400 MHz, DMSO-d6) δ(ppm) 7.82 (br s, 1H), 8.21 (s, 1H), 8.34 (m, 1H), 11.17 (br s, 1H). LCMS: Rt 3.17 min (98.7%), m/z (APCI) 295 (M+H)$^+$.

Step 3: 5,8-Dibromo-[1,2,4]triazolo[1,5-a]pyrazine (F)

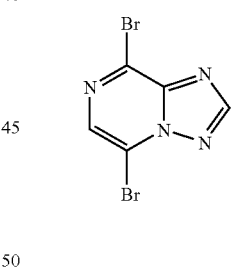

N-(3,6-dibromo-pyrazin-2-yl)-N'-hydroxyformamidine (17.4 mg, 58.80 mmol) is treated with polyphosphoric acid (150 g) for one hour at 50° C. and then for 1.75 hours at 70° C. After cooling to room temperature, water is added to the reaction mixture. The resultant suspension is brought to pH 8 by careful addition of solid NaHCO$_3$ in small portions. The precipitate formed is collected by filtration, washed once with 1N NaOH, three times with water and dried in vacuo. The residue is partitioned between ethyl acetate and 1N NaOH and the organic phase is washed one more time with 1N NaOH and once with brine. The organic phase is dried over anhydrous MgSO$_4$, filtered and evaporated to give the title compound (10.15 g) as a white solid. $^1$H-NMR (400 MHz, DMSO-d6) δ (ppm) 8.43 (s, 1H), 8.92 (s, 1H). LCMS: Rt 2.73 min (94.2%), m/z (APCI) 277 (M+H)$^+$.

Intermediate 4: 5-(4,4,5,5-Tetramethyl-[1,3,2]dioxaborolan-2-yl)-2,3-dihydro-isoindol-1-one

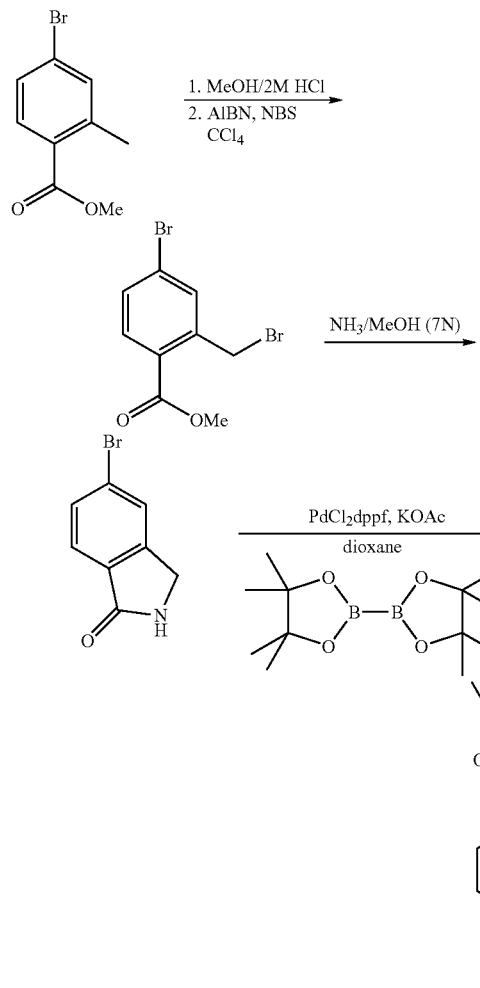

Step 1: 4-Bromo-2-bromomethyl-benzoic acid methyl ester

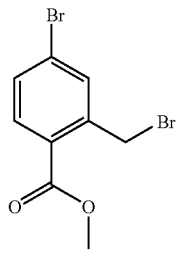

4-Bromo-2-methyl-benzoic acid (4.6 g, 21.39 mmol) is dissolved in 2M HCl in MeOH and refluxed for 3 hours. The solvent is evaporated to give the 4-bromo-2-methyl-benzoic acid methyl ester (4.24 g, 86%). This intermediate (18.51 mmol) is dissolved in carbon tetrachloride (100 mL) and N-bromosuccinimide (5.57 g, 24.06 mmol) is added. AIBN (122 mg, 740 μmol) is then added and the mixture purged with nitrogen for 5 minutes. The reaction mixture is then refluxed for four hours. After cooling to room temperature the reaction mixture is filtered and the filtrate is evaporated. The residue is purified by flash chromatography (silica gel, 2:1 petroleum ether/ethyl acetate) to give the title compound (3.42g, 60%).

Step 2: 5-Bromo-2,3-dihydro-isoindol-1-one

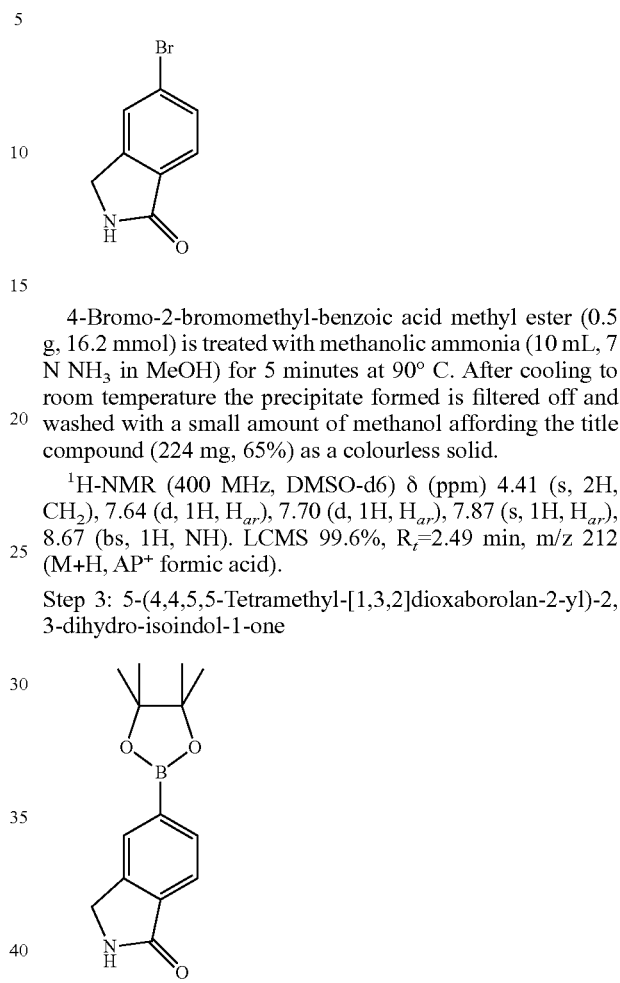

4-Bromo-2-bromomethyl-benzoic acid methyl ester (0.5 g, 16.2 mmol) is treated with methanolic ammonia (10 mL, 7 N $NH_3$ in MeOH) for 5 minutes at 90° C. After cooling to room temperature the precipitate formed is filtered off and washed with a small amount of methanol affording the title compound (224 mg, 65%) as a colourless solid.

$^1$H-NMR (400 MHz, DMSO-d6) δ (ppm) 4.41 (s, 2H, $CH_2$), 7.64 (d, 1H, $H_{ar}$), 7.70 (d, 1H, $H_{ar}$), 7.87 (s, 1H, $H_{ar}$), 8.67 (bs, 1H, NH). LCMS 99.6%, $R_t$=2.49 min, m/z 212 (M+H, $AP^+$ formic acid).

Step 3: 5-(4,4,5,5-Tetramethyl-[1,3,2]dioxaborolan-2-yl)-2,3-dihydro-isoindol-1-one 5-Bromo-2,3-dihydro-isoindol-1-one (230 mg, 1.08 mmol), bis(pinacolato)diboron (300 mg, 1.18 mmol), $PdCl_2$dppf (25 mg, 31 μmol) and KOAc (320 mg, 3.26 mmol) are suspended in dioxane (4 ml), purged with nitrogen for 5 minutes and then heated at 85° C. overnight. The solvent is removed in vacuo and the residue partitioned between ethyl acetate and water. The aqueous layer is extracted three times with ethyl acetate and the combined organic phases are washed once with brine, filtered through anhydrous $MgSO_4$ and evaporated. The solid residue is triturated with hexane and dried in vacuo to furnish the title compound (185 mg, 66%) as a grey solid.

$^1$H-NMR (400 MHz, $CDCl_3$) δ (ppm) 1.37 (s, 12H, 4×$CH_3$), 4.45 (s, 2H, $CH_2$), 6.38 (bs, 1H, NH), 7.87 (d, 1H, $H_{ar}$), 7.93 (m, 2H, $H_{ar}$).

Intermediate 5: 4-(4,4,5,5-Tetramethyl-[1,3,2]dioxaborolan-2-yl)-furan-2-carboxylic acid amide

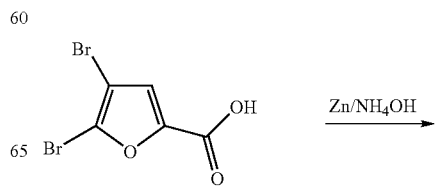

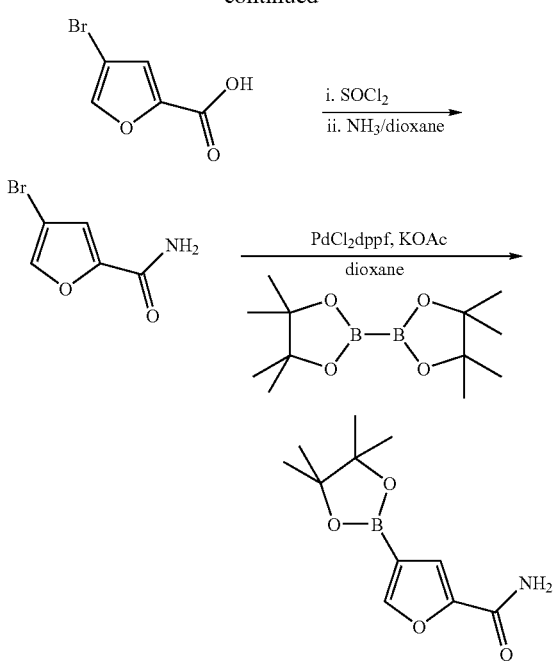

Step 1: 4-Bromo-furan-2-carboxylic acid amide

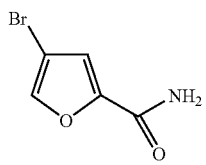

To a cooled (using a cold water bath) solution of 4,5-dibromo-furan-2-carboxylic acid (12.5 g, 46.32 mmol) in NH$_4$OH (100 mL) is added zinc dust (activated, powdered (washed with 2M HCl, water, MeOH, CH$_2$Cl$_2$) 4.54 g, 65.39 mmol) in small portions. The reaction mixture is stirred at room temperature for 10 minutes then filtered over celite and washed with water. The filtrate is cooled to −10° C. (ice/salt bath) and acidified slowly to pH 1 using conc. HCl. The aq layer is immediately extracted with ethyl acetate (4×). The organic phase is washed with brine, dried over anhydrous MgSO$_4$, filtrated and concentrated in vacuo to give an oil (4.96 g) which solidifies on standing to give a white solid, which is used without further purification.

The solid (4.93 g, 25.81 mmol) is dissolved in thionyl chloride (44.2 mL) and refluxed for 1 hour. After removing the solvent in vacuo the residue is dissolved in dichloromethane (75 mL) and a solution of 0.5 M NH$_3$ in dioxane (52 mL) is added. The reaction mixture is stirred at room temperature for 1 hour, then 33% aq. NH$_3$ (5 mL) is added and the reaction stirred for additional 2 hours. The solvent is removed in vacuo and the residue taken-up with a solution of sat. NaHCO$_3$. The basic solution is extracted using ethyl acetate (3×), the combined organic layers are dried over anhydrous MgSO$_4$ and concentrated in vacuo. Purification by silica gel column chromatography eluting with a mixture of (50:49:1) ethyl acetate:petroleum ether:acetic acid, affords the title compound (1.2 g, 22%).

Step 2: 4-(4,4,5,5-Tetramethyl-[1,3,2]dioxaborolan-2-yl)-furan-2-carboxylic acid amide

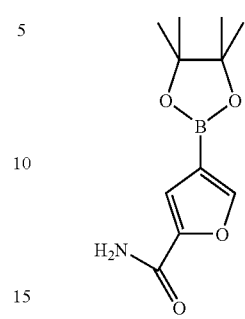

4-Bromo-furan-2-carboxylic acid amide (1.2 g, 6.32 mmol), bis(pinacolato)diboron (1.76 g, 6.94 mmol), PdCl$_2$dppf (0.154 g, 0.189 mmol) and KOAc (1.85 g, 18.94 mmol) are suspended in dioxane (20 mL), purged with nitrogen for 5 minutes and then heated at 85° C. overnight. The solvent is removed in vacuo and the residue partitioned between ethyl acetate and brine. The aqueous layer is extracted four times with ethyl acetate, filtered through anhydrous MgSO$_4$ and evaporated. The solid residue is triturated with hexane and dried in vacuo to afford the title compound as a solid (0.984 g, 66%). N.B. compound is usually 50-60% pure by $^1$H-NMR.

Alternative route to intermediate 5:

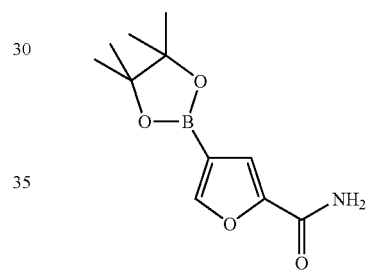

3-(4,4,5,5-Tetramethyl-[1,3,2]dioxaborolan-2-yl)-furan (5.0 g, 25.77 mmol) is dissolved in dry acetonitrile (30 mL). Chlorosulfonylisocyanate (5.47 g, 38.65 mmol, 1.5 equiv.) in solution in dry acetonitrile (20 mL) is added in one portion at room temperature to the furan producing a pink solution that subsides overnight to turn yellow. The resulting solution is cooled with an ice bath and water (5 mL) is added, causing an exotherm. The resulting mixture is partitionned between DCM (100 mL) and water (30 mL). The aqueous layer is extracted 3 more times with DCM (50 mL), then the organic layers are gathered, washed with brine (10 mL), dried over anhydrous Na$_2$SO$_4$ and finally the solvent is removed under vacuum. The oily residue is dissolved in DCM (3 mL), sonicated to give a suspension of a crystalline solid. The solid is separated by filtration, and the cake is washed with a very small amount of DCM, then diethyl ether and dried under suction to afford 3 g of the title compound as a white powder.

Intermediate 6: 2-Ethoxypyridyl-4-boronic acid pinacol ester

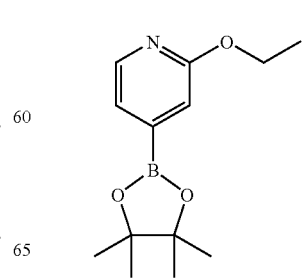

2-Ethoxy-4-bromopyridine (2.5 g, 12.4 mmol), bis-pinacolatodiboron (3.4 g, 13.7 mmol) and potassium acetate (3.64 g, 37.20 mmol) are dissolved in 1,4-dioxane (40 ml) and degassed with nitrogen for 15 minutes. PdCl$_2$dppf (3 mol%, 0.37 mmol, 0.3 g) is then added and the mixture was heated in a sealed vessel at 90° C. for 16 hours. Water is added and the mixture was extracted with EtOAc. The organics are washed with brine and dried over anhydrous MgSO$_4$ then concentrated in vacuo. The crude product is purified by flash chromatography on silica (petrol to 10% EtOAc in petrol) to give 2-ethoxypyridyl-4-boronic acid pinacol ester as a pale oil (2.58 g, 83%).

NMR δ $^1$H (400 MHz, DMSO-d6): 8.16 (1H, m); 7.15 (1H, m); 7.11 (1H, s); 4.33 (2H, q); 1.38 (3H, t); 1.34 (12H, s).

Intermediate 7: 4-((1S,4S)-5-Isopropyl-2,5-diaza-bicyclo[2.2.1]hept-2-yl)-phenylamine Step 1: ((1S,4S)-5-(4-Nitro-phenyl)-2,5-diaza-bicyclo[2.2.1]heptane-2-carboxylic acid tent-butyl ester

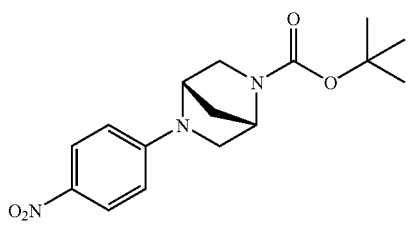

4-Fluoronitrophenyl (4.00 g, 28.348 mmol), DiPEA (5.89 mL, 60.667 mmol, 2.14 equiv.) and (1S,4S)-2-BOC-2,5-diazabicyclo[2.2.1]heptane (6.02 g, 30.333 mmol, 1.07 equiv.) are mixed in acetonitrile (20 mL). The resulting solution is heated to reflux overnight, after which full conversion has occurred. The solvent is removed under vacuum, and the solid yellow residue is stirred in cyclohexane (50 mL) for 0.25 h, then allowed to settle, the supernatant is discarded, and the process is repeated twice. On the third time, the solid is separated by filtration, allowed to dry under suction, to afford the title compound clean as a yellow solid (8.8 g).

Step 2: (1S,4S)-2-(4-Nitro-phenyl)-2,5-diaza-bicyclo[2.2.1]heptane

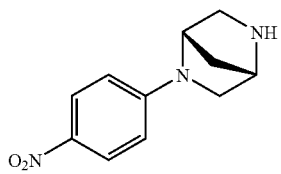

The solid obtained in the previous step (8.2 g) is dissolved in a mixture of DCM (12 mL) and TFA (12 mL). The reaction is allowed to proceed at RT for 2 h, at which point full deprotection has occurred. The volatiles are removed under vacuum and the crude resulting solid is used as such without further treatment.

Step 3: (1S,4S)-2-Isopropyl-5-(4-nitro-phenyl)-2,5-diaza-bicyclo[2.2.1]heptane

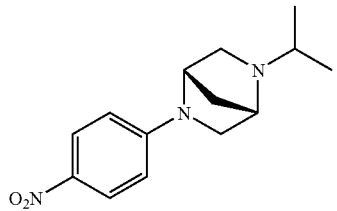

The crude compound obtained in the previous step (6.22 g, 28.356 mmol) is dissolved in acetonitrile (70 mL). K$_2$CO$_3$ (19.59 g, 141.770 mmol, 5.00 equiv.) is added, followed by i-propyl iodide (9.64 g, 56.708 mmol, 2.00 equiv.) and the resulting suspension is heated to reflux with stirring, for 3 h, at which point full conversion has occurred. The reaction mixture is partitioned between DCM (100 mL) and water (50 mL). The organic layer is washed with water (50 mL), brine (25 mL), dried on anhydrous Na$_2$SO$_4$, filtered and evaporated in vacuo to yield the title compound (9.90 g) as a yellow solid.

Step 4: 4-((1S,4S)-5-Isopropyl-2,5-diaza-bicyclo[2.2.1]hept-2-yl)-phenylamine

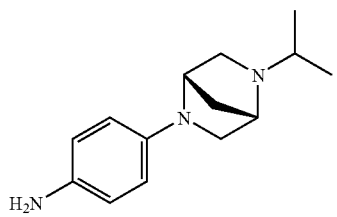

The compound obtained in the previous step (3.30g, 9.35 mmol) is dissolved in EtOH (107 mL). The system is degassed and placed under nitrogen. Pd/C 10% (0.50 g, 5 mol %) is added followed by hydrazine, 35% in water (4.3 mL, 46.75 mmol, 5 equiv.), and the reaction is allowed to proceed at 100° C. until full conversion has occurred (typically 1 h). The reaction is then allowed to cool down, filtered on celite and the filtrate is evaporated in vacuo to afford the title compound (2.07 g) as pink oil.

Intermediate 8: ((1S,4S)-5-tert-Butyl-2,5-diaza-bicyclo[2.2.1]hept-2-yl)-phenylamine Step 1: (2S,4R)-4-Hydroxy-1-(4-nitro-phenyl)-pyrrolidine-2-carboxylic acid methyl ester

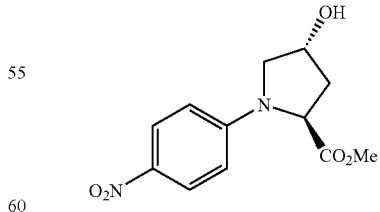

(2S,4R)-L-Prolinol methyl ester (4.7 g, 25.878 mmol) is dissolved in acetonitrile (10 mL) and DiPEA (13.5 mL, 77.635, 3 equiv.). 4-fluoronitrobenzene is then added to the reaction mixture which is heated to 50° C. overnight. After solvent removal, under vacuum, the orange oily residue is partitioned between DCM (50 mL) and water pH 4 (50 mL).

The aqueous layer is further extracted with DCM (4×50 mL), the combined organic layers are washed with brine and dried over anhydrous MgSO₄, to afford the title compound as an orange oil.

Step 2: (3R,5S)-5-Hydroxymethyl-1-(4-nitro-phenyl)-pyrrolidin-3-ol

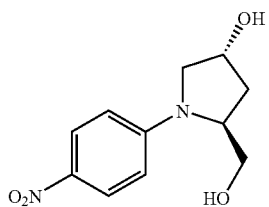

The compound obtained in the previous step (6.89 g, 25.878 mmol) is dissolved in THF (50 mL), and LiBH₄ (51.756 mmol, 1.13 g, 2.00 equiv.) is added portionwise to the resulting solution causing effervescence. The resulting mixture is allowed to react at room temperature until full conversion has occurred. The reaction is then quenched with 1M HCl, to pH 7, and the resulting solution is partitioned between DCM (100 mL) and water (50 mL). The aqueous layer is then extracted with DCM (4×50 mL). The organic layers are gathered, washed with brine and dried over anhydrous Na₂SO₄, to afford the title compound as a yellow oil (3.2 g) used as such in the next step.

Step 3: (3R,5S)-3-Tosyloxy-5-Tosyloxymethyl-1-(4-nitrophenyl)-pyrrolidine

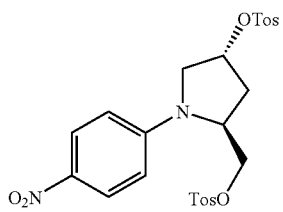

The diol obtained in the previous step (6.2 g, 25.878 mmol) is solubilised in pyridine (31 mL), and cooled to 0° C. Tosyl chloride (14.8 g, 77.734 mmol, 3 equiv.) is then added in one portion and the mixture is stirred at that temperature, and placed in the freezer until needed.

Step 4: (1S,4S)-2-tert-Butyl-5-(4-nitro-phenyl)-2,5-diazabicyclo[2.2.1]heptane

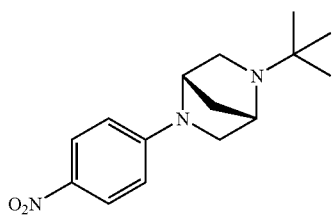

The di-tosylated material (1 g, 1.829 mmol) obtained in the previous step is dissolved in toluene (3 mL) in a pressure tube, and t-butyl amine (0.67 g, 9.147 mmol, 5 equiv.) is added thus giving a burgundy solution. The tube is sealed and heated to 110° C. overnight, at which point full conversion of the starting material has occurred. The crude mixture is allowed to cool down to room temperature, and is diluted in DCM (20 mL), then extracted with 3 M HCl (2×10 mL). The acidic aqueous layers are gathered, washed with DCM (5 mL), then basicified to pH=12-13 by addition of 10% NaOH. The resulting basic layer is extracted with DCM (4×20 mL), the organic layers are gathered, washed with brine and dried over anhydrous Na₂SO₄ to afford after solvent removal and silica chromatography using DCM/MeOH 96/4 as the eluent, the title compound as a yellow oil.

Step 5: 4-((1S,4S)-5-tert-Butyl-2,5-diaza-bicyclo[2.2.1]hept-2-yl)-phenylamine

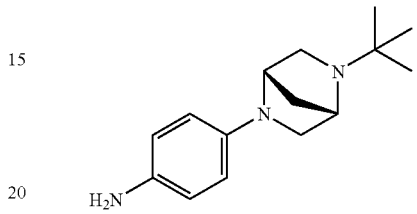

This compound is prepared according to the same procedure as described for Intermediate 7, Step 4.

Intermediate 9: 4-(5-isopropyl-2,5-diazabicyclo[2.2.2]octan-2-yl)aniline

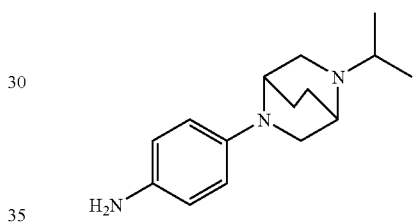

This compound is prepared according to the same procedure as described for Intermediate 7 using 2,5-diazabicyclo[2.2.2]octane dihydrochloride (*J. Heterocycl. Chem,* 1974, 11, 449-451).

Intermediate 10: 4-(8-isopropyl-3,8-diazabicyclo[3.2.1]octan-3-yl)aniline

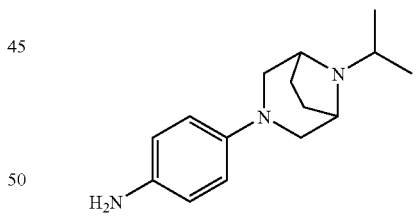

This compound is prepared according to the same procedure as described for Intermediate 7 using 8-(tert-butoxycarbonyl)-3,8-diazabicyclo[3.2.1]octane (*J. Med.Chem.,* 1998, 41, 674-681).

Intermediate 11: 4-(8-isopropyl-3,8-diazabicyclo[3.2.1]octan-3-yl)aniline

Step 1: 3-(tert-butoxycarbonyl)-8-isopropyl-3,8-diazabicyclo[3.2.1]octane

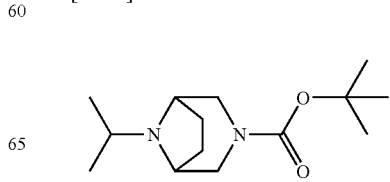

To a solution of 8-(tert-butoxycarbonyl)-3,8-diazabicyclo[3.2.1]octane (*J. Med.Chem.*, 1998, 41, 674-681) (1.54 g, 7.25 mmol) in methanol (25 mL) is added sodium acetate (595.0 mg, 7.25 mmol), acetic acid (415 μL, 7.25 mmol) and acetone (2.66 mL, 36.25 mmol). The reaction mixture is stirred at 40° C. during one hour, and then sodium cyanoborohydride (912.0 mg, 14.50 mmol) is added. The reaction is heated at 40° C. for 18 hours, concentrated in vacuo, taken up in DCM and washed with aq. NaHCO₃. The organic phase is dried over anhydrous MgSO₄ and concentrated in vacuo to afford 3-(tert-butoxycarbonyl)-8-isopropyl-3,8-diazabicyclo[3.2.1]octane (1.51g, 82%).

Step 2: 8-isopropyl-3,8-diazabicyclo[3.2.1]octane

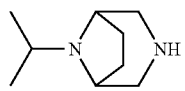

This compound is prepared according to the same procedure as described for Intermediate 7, Step 2.

Step 3: 8-isopropyl-3-(4-nitrophenyl)-3,8-diazabicyclo[3.2.1]octane

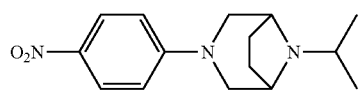

This compound is prepared according to the same procedure as described for Intermediate 7, Step 3.

Step 4: 4-(8-isopropyl-3,8-diazabicyclo[3.2.1]octan-3-yl)aniline

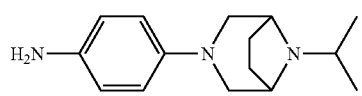

This compound is prepared according to the same procedure as described for Intermediate 7, Step 4.

Intermediate 12: 6-((1S,4S)-5-isopropyl-2,5-diazabicyclo[2.2.1]heptan-2-yl)pyridin-3-amine

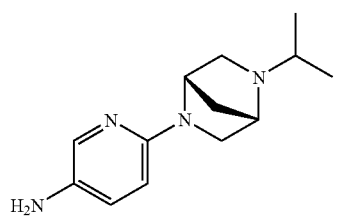

This compound is prepared according to the same procedure as described for Intermediate 7 using 2-chloro-5-nitropyridine.

Intermediate 13: 3-((1S,4S)-5-isopropyl-2,5-diazabicyclo[2.2.1]heptan-2-yl)phenylamine Step 1: (1S,4S)-2-isopropyl-5-(3-nitrophenyl)-2,5-diazabicyclo[2.2.1]heptane

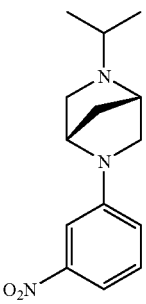

A solution of BINAP (0.47 g, 0.75 mmol) and tris(dibenzylideneacetone)dipalladium (0) (0.34 g, 0.37 mmol) in toluene (120 mL) was heated to 90° C. during 15 minutes under nitrogen. The reaction mixture was cooled to 40° C. before adding 1-bromo-3-nitrobenzene (1.89 g, 9.37 mmol), (1S,4S)-2-isopropyl-2,5-diazabicyclo[2.2.1]heptane dihydrochloride (2.0 g, 9.37 mmol) and sodium tert-butoxide (3.14 g, 32.74 mmol). The reaction was heated to 90° C. during 18 hours under nitrogen. After return to room temperature, the reaction was diluted with ethyl acetate and filtered through celite. The filtrate was concentrated under reduced pressure. The residue was purified by flash chromatography on silica gel eluting with a mixture of DCM/7N NH₃ in methanol (96/4) to afford the title compound (1.92 g, 78%).

Step 2: 3-((1S,4S)-5-isopropyl-2,5-diazabicyclo[2.2.1]heptan-2-yl)phenylamine

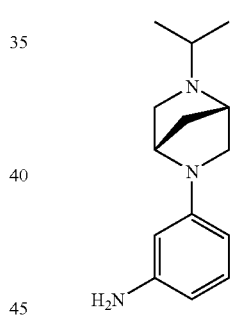

The compound obtained in the previous step (1.92 g, 7.34 mmol) was dissolved in EtOH (50 mL). The system was degassed and placed under nitrogen. Pd(OH)₂ on activated charcoal (10%, 0.2 g) was added and the resulting suspension was stirred at room temperature during 18 hours under hydrogen atmosphere. The reaction was then filtered on celite and the filtrate was evaporated in vacuo to afford the title compound (1.89 g, 98%) as a brown oil.

Intermediate 14: 2-((1S,4S)-5-Isopropyl-2,5-diaza-bicyclo[2.2.1]hept-2-yl)-pyrimidin-5-ylamine

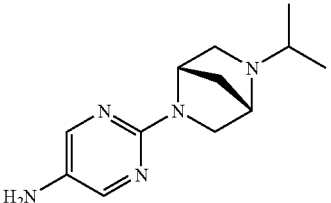

Intermediates of the type above can be produced by the methods described by DiMauro et al (J. Med. Chem.,2008, 51, 1681-1694). Initial reaction of 2-chloro-5-nitropyrimidine with (1S,4S)-2-BOC-2,5-diazabicyclo[2.2.1]heptane, followed by application of the procedures for intermediate 7 would give an intermediate suitable for inclusion in compounds of the invention.

Intermediate 15: (4-Amino-phenyl)-((1S,4S)-5-isopropyl-2,5-diaza-bicyclo[2.2.1]hept-2-yl)-methanone

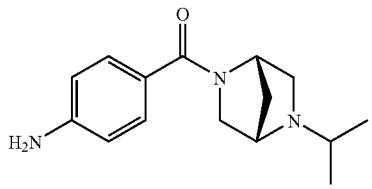

Intermediates of the type above can be produced using methods described in WO 2007/138072. Initial reaction of 4-nitrobenzoic acid with (1S,4S)-2-isopropyl-2,5-diazabicyclo[2.2.1]heptane, followed by reduction of the nitro group would give an intermediate suitable for inclusion in compounds of the invention.

Intermediate 16: (1S,4S)-5-Isopropyl-2,5-diaza-bicyclo[2.2.1]heptane-2-carboxylic acid (4-amino-phenyl)-amide

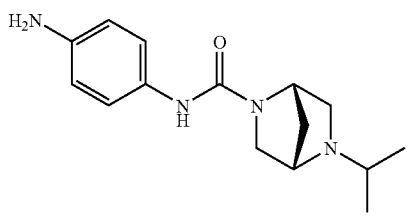

Intermediates of the type above can be produced using methods described in Bioorg. Med Chem Lett, 2008; 4838-4843. Initial reaction of 1-isocyanato-4-nitrobenzene with (1S,4S)-2-isopropyl-2,5-diazabicyclo[2.2.1]heptane, followed by reduction of the nitro group would give an intermediate suitable for inclusion in compounds of the invention.

Intermediate 17: (1R,4R)-2-Isopropyl-2,5-diaza-bicyclo[2.2.1]heptane dihydrobromide

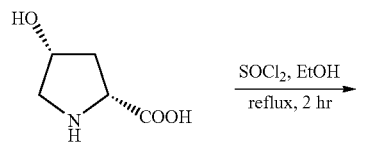

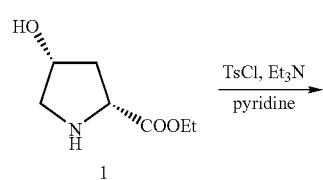

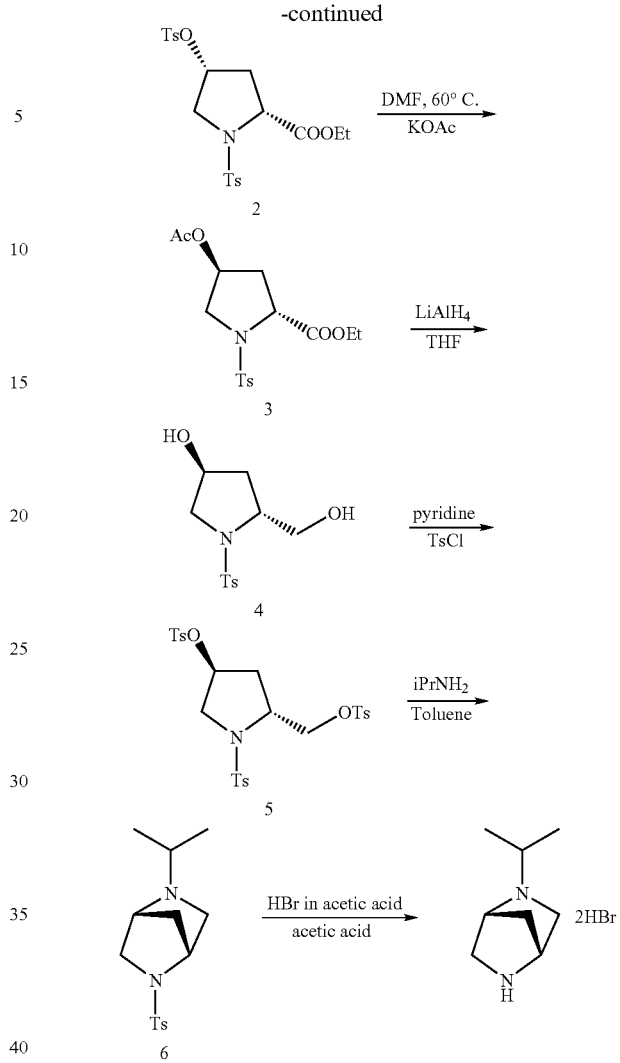

Step 1: (2R,4R)-4-Hydroxy-pyrrolidine-2-carboxylic acid ethyl ester (1)

To a stirred solution of cis-4-hydroxy-pyrrolidine-2-carboxylic acid (1 g, 7.6 mmol) in absolute ethanol (20 mL) is added dropwise thionyl chloride (0.67 mL, 9.15 mmol) at 0° C. under nitrogen atmosphere. The reaction mixture is then refluxed under nitrogen for about 2 h. The mixture is cooled to room temperature, and all solvent is removed under reduced pressure. The white precipitate is filtered and washed with diethyl ether (1×25 mL), to obtain compound (1) as a white solid.

$^1$H-NMR (400 MHz, DMSO-d$_6$): δ 1.23 (t, 3H), 2.12 (d, 1H), 2.27 (t, 1H), 3.19 (q, 2H), 4.20 (m, 2H), 4.35 (s, 1H), 4.47 (d, 1H). Mass (M+1): m/z 160.

Step 2: (2R,4R)-1-(Toluene-4-sulfonyl)-4-(toluene-4-sulfonyloxy)-pyrrolidine-2-carboxylic acid ethyl ester (2)

To a cold solution of 4-hydroxy-pyrrolidine-2-carboxylic acid ethyl ester (1) (1.4 g, 7.1 mmol) and triethyl amine (0.998 mL, 7.1 mmol) in pyridine (14 mL) at −5° C. was added portion-wise 4-toluenesulfonyl chloride (3.42 g, 17.9 mmol). The cold solution was then stirred for 1 h at 0° C. and stored overnight in the refrigerator. Then the mixture was further stirred at room temperature for 5 h and poured into ice water (10 mL). The precipitate separated out was filtered, washed with water (2×5 mL), and dried to give compound (2) as a white solid.

$^1$H-NMR (400 MHz, DMSO-d$_6$): δ 1.13 (t, 3H), 2.05 (d 1H), 2.16 (m, 1H), 2.41 (d, 6H), 4.05 (q, 2H), 4.47 (d, 1H), 5.00 (s, 1H), 7.45 (dd, 4H), 7.72 (d, 4H). Mass (M+1): m/z 468.

Step 3: (2R,4S)-4-Acetoxy-1-(toluene-4-sulfonyl)-pyrrolidine-2-carboxylic acid ethyl ester (3)

To a stirred solution of 1-(toluene-4-sulfonyl)-4-(toluene-4-sulfonyloxy)-pyrrolidine-2-carboxylic acid ethyl ester (2) (1 g, 2.14 mmol) in dry DMF (25 mL) is added potassium acetate (0.314 g, 3.21 mmol) in one portion. The reaction mixture is then heated at 60° C. for 4 h. Water (50 mL) is added to the reaction mixture and extracted with ethyl acetate (2×75 mL), combined organic layer are washed with water (2×50 mL), dried (Na$_2$SO$_4$), filtered, and concentrated under reduced pressure to give the crude compound. Crude compound is purified by column chromatography over silica gel (100-200 mesh) using 15% ethyl acetate-hexane as eluent to give compound (3).

$^1$H-NMR (400 MHz, CDCl$_3$): δ 1.26 (t, 3H), 1.68 (s, 3H), 2.20 (m, 1H), 2.29 (m, 1H), 2.41 (s, 3H), 3.52 (d, 1H), 3.67 (d, 1H), 4.22 (m, 2H), 4.30 (t, 1H), 5.11 (s, 1H), 7.33 (d, 2H), 7.74 (d, 2H). Mass (M+1): m/z 356.

Step 4: (3S,5R)-5-Hydroxymethyl-1-(toluene-4-sulfonyl)-pyrrolidin-3-ol (4)

To an ice-cold solution of 4-acetoxy-1-(toluene-4-sulfonyl)-pyrrolidine-2-carboxylic acid ethyl ester (3) (0.65 g, 1.83 mmol) in THF (10 mL) is added LiAlH$_4$ (0.135 g, 3.66 mmol) portion wise. Then the reaction mixture is stirred at room temperature for 1 h. After completion of the reaction, it is cooled to 0° C. and then pH of reaction mixture is adjusted to 3 by adding 6N HCl (0.65 mL). The mixture is concentrated, and the residue is triturated with water (8 mL), the solid precipitated out is filtered, washed with cold water (2×4 mL), and dried under reduced pressure to give compound (4) as white solid.

$^1$H-NMR (400 MHz, CDCl$_3$): δ 1.14 (s, 1H), 1.82 (m, 1H), 1.91 (m, 1H), 2.42 (s, 3H) 3.39 (d, 1H), 3.55 (d, 1H), 3.60 (m, 1H), 3.77 (m, 1H), 3.85 (d, 1H), 4.30 (s, 1H), 7.31 (d, 2H), 7.76 (d, 2H). Mass (M+1): m/z 272.

Step 5: (2R,4S)-1-(4-Tolylsulfonyl)-2-[[(4-tolylsulfonyl)oxy]-methyl]-4-[(4-tolylsulfonyl)oxy]-pyrrolidine (5)

To an ice-cold solution of 5-hydroxymethyl-1-(toluene-4-sulfonyl)-pyrrolidin-3-ol (4) (0.45 g, 1.66 mmol) in pyridine (3 mL) is added 4-toluylsulfonyl chloride (1.11 g, 5.81 mmol) in one portion. The temperature rises to 50° C., then the reaction mixture is cooled to 10° C., kept at that temperature for an additional 2 h and then left at room temperature overnight. The mixture is poured into 2N HCl (13 mL). On cooling the compound precipitates out and separated by filtration, washed with cold water (2×5 mL), and dried under reduced pressure to give compound (5) as white solid.

$^1$H-NMR (400 MHz, CDCl$_3$): δ 2.02 (m, 2H), 2.42(s, 9H), 3.50 (d, 2H), 3.80 (d, 1H) 4.10 (q,1H), 4.30(d, 1H), 4.76 (t, 1H), 7.27 (dd, 4H), 7.35 (d, 2H), 7.56 (d, 2H), 7.62 (d, 2H), 7.78 (d, 2H). Mass (M+1): m/z 538.

Step 6: (1R,4R)-2-Isopropoyl-5-(toluene-4-sulfonyl)-2,5-diaza-bicyclo[2.2.1]heptane (6)

To a mixture of (2R,4S)-1-(4-tolylsulfonyl)-2-[[(4-tolylsulfonyl)oxy]-methyl]-4-[(4-tolylsulfonyl)oxy]pyrrolidine (5) (0.5 g, 0.93 mmol) and isopropyl amine (0.3 mL, 0.33 mmol) in dry toluene (3 mL) is heated to 110° C. for 10 h. The mixture is then cooled to room temperature; a solid separates out and is separated by filtration and washed with toluene (1×15 mL). The combined organic layer is dried over (Na$_2$SO$_4$), filtered and concentrated under reduced pressure to give crude product which is purified by column chromatography over silica gel (100-200 mesh) using 1% triethylamine-ethyl acetate as eluent to afford compound (6) as white solid.

$^1$H-NMR (400 MHz, CDCl$_3$): δ 0.72 (d, 1H), 0.89 (t, 6H), 1.46 (d, 1H), 2.32 (s, 1H), 2.38 (s,3H), 2.46 (t, 1H), 2.85 (d, 2H), 3.51 (s, 1H), 4.18 (s, 1H), 7.44 (d, 2H), 7.71 (d, 2H). Mass (M+1): m/z 295.

Step 7: (1R,4R)-2-Isopropyl-2,5-diaza-bicylo[2.2.1]heptane dihydrobromide.

To a solution of 33% HBr (0.5 mL) and acetic acid (3 mL) at 70° C. is added (1R,4R)-2-isopropoyl-5-(toluene-4-sulfonyl)-2,5-diaza-bicyclo[2.2.1]heptane (6) (0.24 g, 0.000816 mol). The mixture is then stirred for 12 h at same temperature. The mixture is cooled to 10° C. to yield a white precipitate which is filtered and washed with diisopropyl ether (1×5 mL) and ethyl acetate (1×5 mL), dried under reduced pressure to afford intermediate 17 as a white solid.

$^1$H-NMR (400 MHz, D$_2$O):δ 1.33 (d, 3H), 1.39 (d, 3H), 2.29 (d, 1H), 2.41 (d, 1H), 3.57 (m,3H), 3.73 (s, 2H), 4.61 (s, 1H), 4.75 (s, 1H). Mass (M+1): m/z 141.

Intermediate 18: 2-Carboxamido-4-furanboronic acid

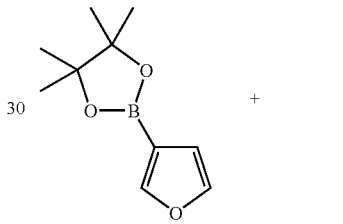

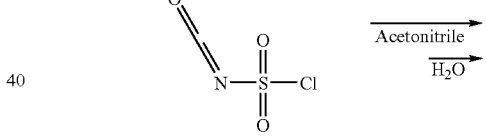

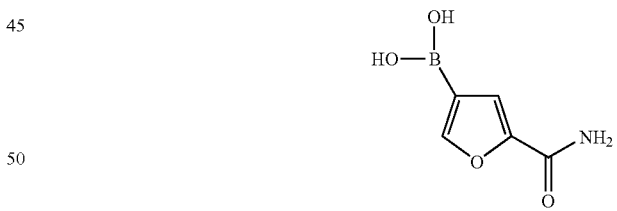

15 g 3-Furanboronic acid pinacol ester (77.3 mmol, 1.0 eq) is dissolved in 120 mL acetonitrile, 10.2 mL chlorsulfonyl isocyanate (116 mmol, 1.5 eq) is added in one portion. Stirring is continued over night. Full conversion is determined by LCMS. Reaction is quenched by slowly adding 30 mL H$_2$O. The solution is concentrated and 100 mL IPA is added. This procedure is repeated and the reaction mixture is diluted by adding 120 mL H$_2$O and 8 mL IPA and stirred for 2 hours. The precipitate formed during the process is filtered off and washed with 30 mL H$_2$O. After drying, the solid is recrystallised from 120 mL IPA and 6 mL H$_2$O. The crystals are washed with 30 mL IPA and isolated in 99+% purity.

Specific Examples of Compounds of the Invention

Compound 1: 5-{8-[4-((1S,4S)-5-Isopropyl-2,5-diaza-bicyclo[2.2.1]hept-2-yl)-phenylamino]-[1,2,4]triazolo[1,5-a]pyrazin-5-yl}-2,3-dihydro-isoindol-1-one

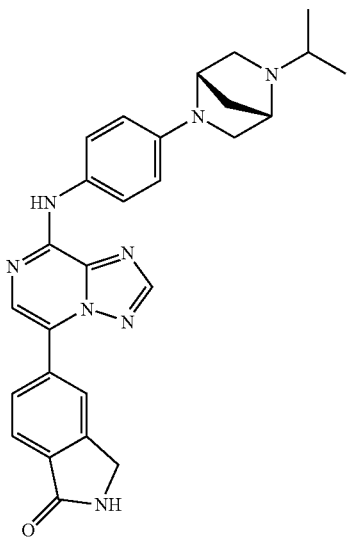

This compound may be prepared according to the same procedure as described for Compound 2 using the corresponding intermediates described above.

$^1$H NMR (400 MHz, DMSO-d6): δ 9.81 (s, 1H); 8.65 (m, 2H); 8.19 (s, 1H); 8.07-8.05 (m, 1H); 7.93)s, 1H); 7.82-7.79 (m, 2H); 7.75-7.73 (m, 2H); 6.60 (m, 2H); 4.47 (s, 2H); 4.25 (s, 1H); 3.69 (s, 1H); 3.18 (m, 1H); 2.99 (m, 1H); 2.39-2.36 (m, 2H); 1.80 (s, 2H); 0.93 (d, 6H); m/z: M+H$^+$ (481.1; 100%).

Compound 2: 4-{8-[4-((1S,4S)-5-Isopropyl-2,5-diaza-bicyclo[2.2.1]hept-2-yl)-phenylamino]-[1,2,4]triazolo[1,5-a]pyrazin-5-yl}-furan-2-carboxamide Step 1: (5-Bromo-[1,2,4]triazolo[1,5-a]pyrazin-8-yl)-[4-((1S,4S)-5-isopropyl-2,5-diaza-bicyclo[2.2.1]hept-2-yl)-phenyl]-amine

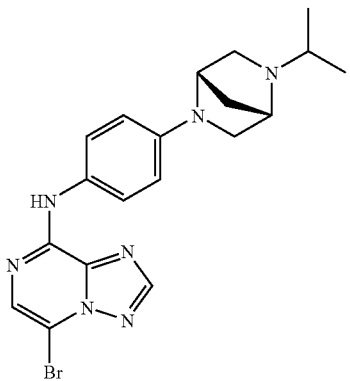

5,8-Dibromo-[1,2,4]triazolo[1,5-a]pyrazine (2.26 g, 8.14 mmol), 4-((1S,4S)-5-Isopropyl-2,5-diaza-bicyclo[2.2.1]hept-2-yl)-phenylamine (2.07 g, 8.95 mmol, 1.10 equiv.) and DiPEA (4.3 mL, 24.42 mmol, 3.00 equiv.) are mixed in isopropanol (28 mL) under nitrogen. The reaction is heated to 85° C. until completion of the reaction (typically 5 h). The solvent is removed under vacuum and the residue is partitioned between 60 mL aqueous sodium phosphates buffer (pH 7) and 200 mL DCM, the organic layer is washed with 60 mL satd. NaCl, dried on anhydrous Na$_2$SO$_4$, filtered and evaporated in vacuo to yield the title compound (3.67 g) as a green-black foamy solid.

Step 2: 4-{8-[4-((1S,4S)-5-Isopropyl-2,5-diaza-bicyclo[2.2.1]hept-2-yl)-phenylamino]-[1,2,4]triazolo[1,5-a]pyrazin-5-yl}-furan-2-carboxamide

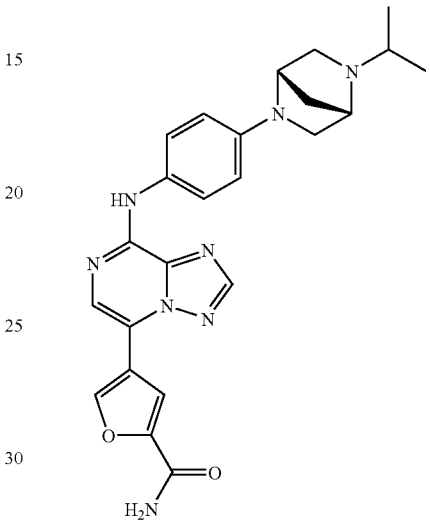

The compound obtained in the previous step (3.25 g, 7.59 mmol) is mixed with 4-(4,4,5,5-Tetramethyl-[1,3,2]dioxaborolan-2-yl)-furan-2-carboxylic acid amide (2.70 g, 11.40 mmol, 1.50 equiv.), PdCl$_2$dppf.DCM (0.310 g, 0.38 mmol, 5 mol %), DiPEA (2.65 mL, 15.20 mmol, 2.00 equiv.) in 1,4-Dioxane (51 mL) and water (13 mL). The system is sealed, purged by vacuum/N2 and heated to 110° C. for 6 h, at which point full conversion has occurred. The reaction mixture is diluted with DCM (60 mL) and MeOH (60 mL) and filtered on celite. The filtrate is evaporated to yield a muddy brown residue. This residue is treated with EtOH (50 mL), MeOH (25 mL) and DCM (20 mL), and evaporated to dryness, then left in vacuo at 40° C. for another 1 h to try and eliminate as much moisture and alcohols as possible. The dry residue is suspended in DCM (100 mL) and sonicated for about 1 h, to disperse all the solid bits. A suspension of fine solid is obtained. It is cooled to 0° C., filtered on Buchner, and the solid was washed with DCM (30 mL) and dried under vacuum.

The residue is treated with 1M KOH (40 mL), sonicated until the solid is well dispersed, and filtered on a sintered glass funnel. Finally, the solid is dissolved in DCM (450 mL) and MeOH (50 mL), washed with a mixture of saturated aqueous NaF (250 mL), water (500 mL) and iPrOH (250 mL). The organic layer was dried on anhydrous Na$_2$SO$_4$, filtered and evaporated in vacuo to yield 4-{8-[4-((1S,4S)-5-Isopropyl-2,5-diaza-bicyclo[2.2.1]hept-2-yl)-phenylamino]-8 1,2,4]triazolo[1,5-a]pyrazin-5-yl}-furan-2-carboxylic acid amide (2.34 g) as a yellow-brown solid.

NMR (400 MHz, DMSO-d6): δ 9.76 (s, 1 H); 8.74 (s, 1 H); 8.69 (d. 1 H); 8.13 (s, 1 H); 7.93 (broad s, 1 H); 7.86 (d, 1 H); 7.72 (d, 2 H); 7.54 (broad s, 1 H); 6.59 (d, 2 H); 4.31 (d, 1 H (iPrOH)); 4.25 (s, 1.1 H); 3.78 (m, 1 H (iPrOH)); 3.69 (s, 1 H);

3.30 (H₂O); 3.16 (d(d), 1 H); 3.00 (d(d), 1 H); 2.50 (DMSO); 2.42-2.37 (m, 2 H); 1.81 (s, 2 H); 1.04 (d, 7 H) (i-PrOH); 0.95 (2 d, 6 H).

Compound 3: 4-{8-[4-((1S,4S)-5-tert-Butyl-2,5-diaza-bicyclo[2.2.1]hept-2-yl)-phenylamino]-[1,2,4]triazolo[1,5-a]pyrazin-5-yl}-furan-2-carboxamide

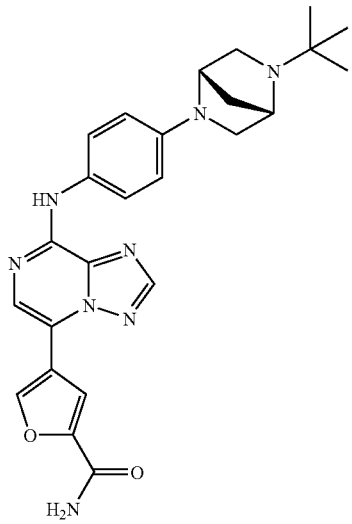

This compound may be prepared according to the same procedure as described for Compound 2 above using the corresponding intermediates described above.

¹H NMR (400 MHz, DMSO-d6): δ 9.27 (s, 1H), 8.72 (s, 1H), 8.68 (d, 1H), 8.11 (s, 1H), 7.91 (broad s, 1H), 7.84 (d, 1H), 7.68 (d, 2H), 7.58 (broad s, 1H), 6.55 (d, 2H), 3.40-3.36 (m, 2H), 2.89-2.80 (m, 4H), 1.72-1.70 (d, 1H), 1.63-1.60 (d, 1H), 0.97 (s, 9H); m/z: M+H⁺ (473.1; 100%).

Compound 4: 4-{8-[4-((1S,4S)-5-Isopropyl-2,5-diaza-bicyclo[2.2.1]hept-2-yl)-phenylamino]-imidazo[1,2-a]pyrazin-5-yl}-furan-2-carboxamide

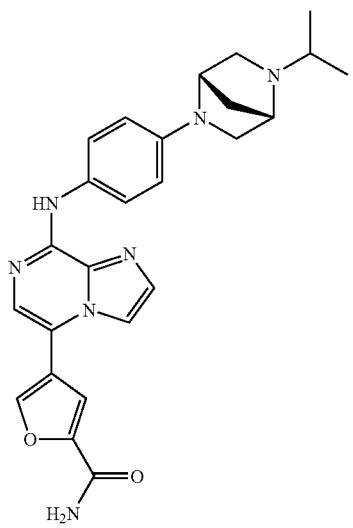

This compound may be prepared according to the same procedure as described for Compound 2 using the corresponding intermediates described above.

¹H NMR (400 MHz, DMSO-d6): δ 9.33 (s, 1H), 8.45 (s, 1H), 8.17 (s, 1H), 7.94 (brs, 1H), 7.75-7.72 (m, 3H), 7.62 (d, 2H), 7.59 (brs, 1H), 6.58 (d, 2H), 4.24 (s, 1H), 3.69 (s, 1H), 3.32 (d, 1H), 3.15 (d, 1H), 2.98 (d, 1H), 2.43-2.38 (m, 2H), 1.81 (s, 2H), 0.98 (d, 3H), 0.92 (d, 3H); m/z: M+H⁺ (458; 100%).

Compound 5: 5-{8-(4-((1S,4S)-5-isopropyl-2,5-diazabicyclo[2.2.1]heptan-2-yl)phenyl-amino)-[1,2,4]triazolo[1,5-a]pyrazin-5-yl}-1H-pyrazole-3-carboxamide Step 1: Ethyl 5-(8-(4-((1S,4S)-5-isopropyl-2,5-diazabicyclo[2.2.1]heptan-2-yl)phenylamino)-[1,2,4]triazolo[1,5-a]pyrazin-5-yl)-1H-pyrazole-3-carboxylate

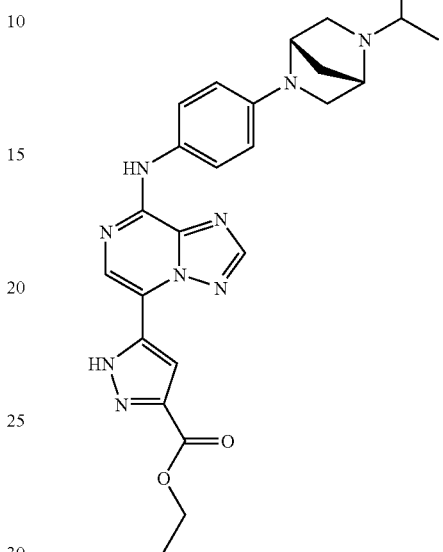

A mixture of ethyl 5-(tributylstannyl)-1H-pyrazole-3-carboxylate (109.0 mg, 0.25 mmol) (*Heterocyles*, 1992, 813-818), (5-bromo-[1,2,4]triazolo[1,5-a]pyrazin-8-yl)-[4-((1S,4S)-5-isopropyl-2,5-diazabicyclo[2.2.1]hept-2-yl)-phenyl]amine (163.0 mg, 0.38 mmol), and Pd(PPh₃)₂Cl₂ (27.0 mg, 0.04 mmol) in THF (3 mL) is refluxed for 18 hours. After return to room temperature, solvent is removed under reduced pressure. Purification of the residue by silica gel column chromatography eluting with a mixture of DCM/7N NH₃ in methanol (97/3) affords the title compound (35.0 mg, 28%).

Step 2: 5-{8-(4-((1S,4S)-5-isopropyl-2,5-diazabicyclo[2.2.1]heptan-2-yl)phenylamino)-[1,2,4]-triazolo[1,5-a]pyrazin-5-yl}-1H-pyrazole-3-carboxamide

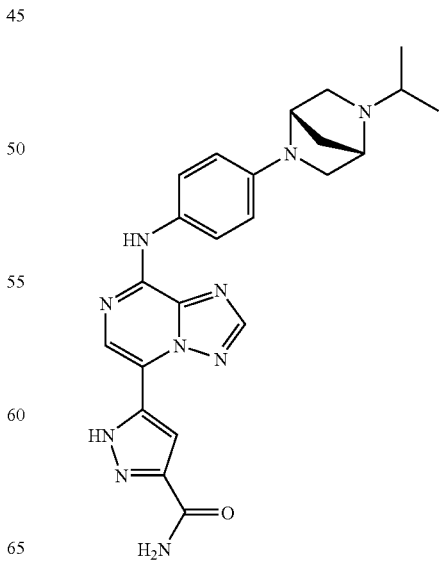

A mixture of the compound obtained in the previous step (30.0 mg, 0.06 mmol), ammonium chloride (200 mg) and ammonium hydroxide (2 mL) in methanol (12 mL) is heated at 85° C. for 18 hours. After return to room temperature, solvents are removed under reduced pressure. Purification by silica gel column chromatography eluting with a mixture of DCM/7N NH$_3$ in methanol (95/5) affords the title compound (20.0 mg, 71%).

NMR $^1$H (400 MHz, DMSO-d6): δ 14.01 (broad s, 1H); 9.83 (s, 1H); 8.73 (s, 1H); 8.23 (s, 1H); 8.14 (broad s, 1H); 7.78-7.75 (m, 3H); 7.32 (broad s, 1H); 6.64-6.62 (m, 2H); 4.65 (s, 1H); 4.35 (s, 1H); 3.21-3.19 (m, 1H); 3.04-3.02 (m, 1H); 2.54 (s, 1H); 2.45-2.41 (m, 2H); 1.84-1.82 (m, 2H); 1.01 (2d, 6H); m/z: 459 (M+H)$^+$.

Compound 6: 4-{8-(4-((1S,4S)-5-tert-butyl-2,5-diazabicyclo[2.2.19 heptan-2-yl)-phenyl-amino)imidazo[1,2-a]pyrazin-5-yl}-furan-2-carboxamide

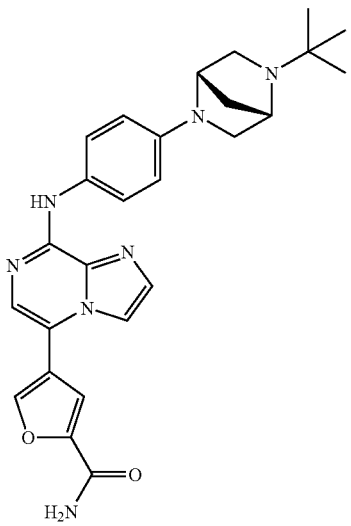

This compound may be prepared according to the same procedure as described for Compound 2 using the corresponding intermediates described above.

$^1$H NMR (400 MHz, DMSO-d6): δ 9.33 (s, 1H); 8.46 (s, 1H); 8.11 (s, 1H); 7.99 (broad s, 1H); 7.72-7.70 (m, 3H); 7.62-7.59 (m, 3H); 6.56-6.54 (m, 2H); 4.28 (s, 1H); 4.67 (s, 1H); 3.91-3.76 (m, 4H); 1.73 (d, 1H); 1.65 (d, 1H); 0.98 (s, 9H); m/z: 472 (M+H)$^+$.

Compound 7: 4-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-furan-2-carboxamide

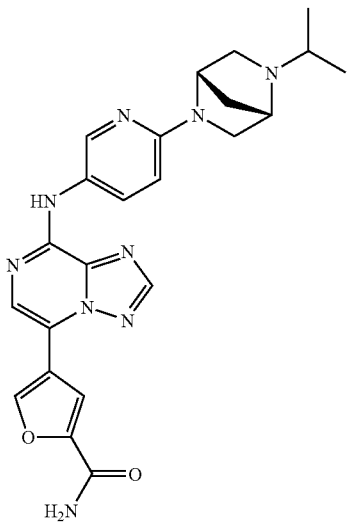

This compound may be prepared according to the same procedure as described for Compound 2 using the corresponding intermediates described above.

$^1$H NMR (400 MHz, DMSO-d6): δ 9.94 (s, 1H); 8.80 (s, 1H); 8.74 (s, 1H); 8.58 (s, 1H); 8.17 (s, 1H); 8.03-7.99 (m, 2H); 7.90 (s, 1H); 7.59 (broad s, 1H); 6.58 (d, 1H); 4.58 (s, 1H); 3.76 (s, 1H); 3.49 (d, 1H); 3.31-3.29 (m, 1H); 3.06 (d, 1H); 2.51-2.48 (m, 1H); 2.39 (d, 1H); 1.86-1.83 (m, 2H); 0.98 (2d, 6H); m/z: 460 (M+H)$^+$.

Compound 8: 4-{8-(4-((1S,4S)-5-isopropyl-2,5-diazabicyclo[2.2.1]heptan-2-yl)phenyl-amino)imidazo[1,2-a]pyrazin-5-yl}-1H-pyridin-2-one Step 1: 5-(2-ethoxypyridin-4-yl)-N-(4-((1S,4S)-5-isopropyl-2,5-diazabicyclo[2.2.1]heptan-2-yl)phenyl)imidazo[1,2-a]pyrazin-8-amine

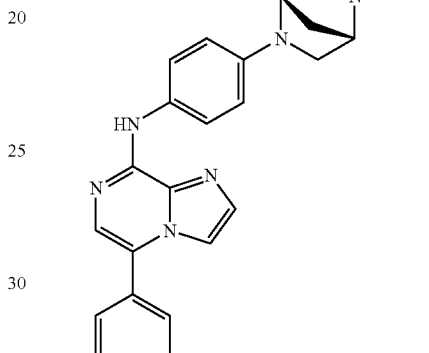

This compound may be prepared according to the same procedure as described for Compound 2 using the corresponding intermediates described above.

Step 2: 4-{8-(4-((1S,4S)-5-isopropyl-2,5-diazabicyclo[2.2.1]heptan-2-yl)pheny-amino)imidazo-[1,2-a]-pyrazin-5-yl}-1H-pyridin-2-one

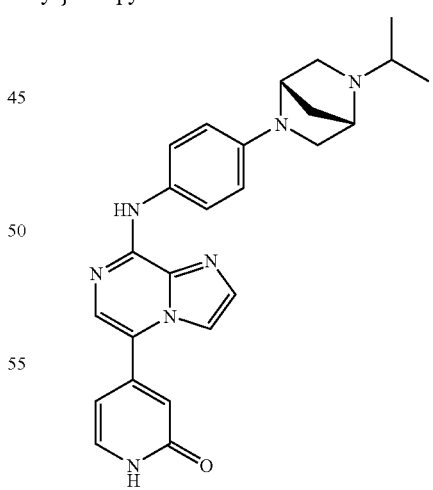

A mixture of the compound obtained in the previous step (135.0 mg, 0.29 mmol) and pyridine hydrochloride (332.0 mg, 2.90 mmol) is heated to 120° C. for 18 hours. After return to room temperature, the crude is dissolved in methanol, dry loaded onto silica. Purification by silica gel column chromatography eluting with a mixture of DCM/7N NH$_3$ in methanol (96/4) affords the title compound (46.0 mg, 36%).

NMR ¹H (400 MHz, CDCl₃): δ 12.51 (broad s, 1H); 8.00 (s, 1H); 7.82 (s, 1H); 7.64-7.59 (m, 4H); 7.50-7.48 (m, 1H); 6.86 (s, 1H); 6.60-6.59 (m, 2H); 6.55-6.53 (m, 1H); 4.20 (s, 1H); 3.81 (s, 1H); 3.49-3.41 (m, 2H); 3.21-3.18 (m, 1H); 2.51-2.49 9m, 2H); 2.05-2.03 (m, 1H); 1.97-1.95 (m, 1H); 1.07 (d, 3H); 1.02 (d, 3H); m/z: 442 (M+H)⁺.

Compound 9: 4-{8-(4-(5-isopropyl-2,5-diazabicyclo[2.2.2]octan-2-yl)phenylamino)[1,2,4]-triazolo[1,5-a]pyrazin-5-yl}-furan-2-carboxamide

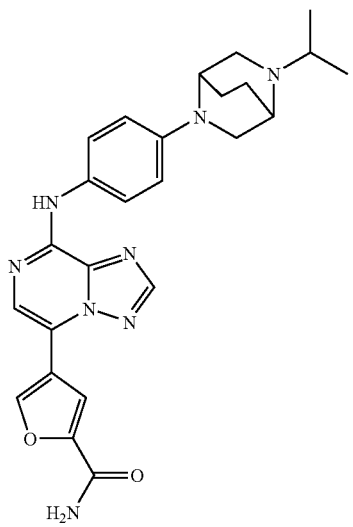

This compound is prepared according to the same procedure as described for Compound 2 using the corresponding intermediates described above.

¹H NMR (400 MHz, DMSO-d6): δ 9.80 (s, 1H); 8.78 (s, 1H); 8.73 (s, 1H); 8.17 (s, 1H); 7.98 (broad s, 1H); 7.89 (s, 1H); 7.76 (d, 2H); 7.59 (broad s, 1H); 6.68 (d, 2H); 3.92-3.91 (m, 1H); 3.58 (d, 1H); 3.22-3.19 (m, 2H); 2.96-2.94 (m, 2H); 2.71-2.68 (m, 1H); 1.94-1.76 (m, 3H); 1.60-1.59 (m, 1H); 1.04 (2d, 6H); m/z: 473 (M+H)⁺.

Compound 10: 4-{8-(4-(5-isopropyl-1-2,5-diazabicyclo[2.2.2]octan-2-yl)phenylamino)-imidazo[1,2-a]pyrazin-5-yl}-furan-2-carboxamide

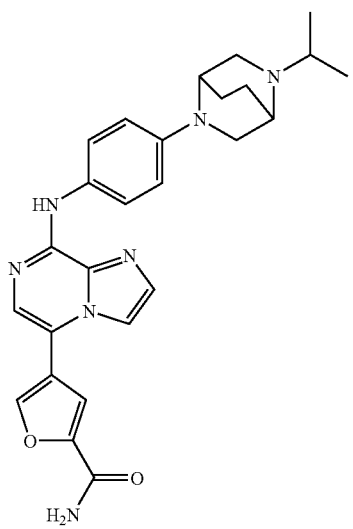

This compound is prepared according to the same procedure as described for Compound 2 using the corresponding intermediates described above.

¹H NMR (400 MHz, DMSO-d6): δ 9.23 (s, 1H); 8.38 (s, 1H); 8.02 (s, 1H); 7.86 (broad s, 1H); 7.68-7.64 (m, 3H); 7.55-7.52 (m, 2H); 7.47 (broad s, 1H); 6.59 (m, 2H); 3.79 (s, 1H); 3.48-3.45 (m, 1H); 3.11-3.08 (m, 2H); 2.84-2.82 (m, 2H); 2.59-2.57 (m, 1H); 1.83-1.74 (m, 3H); 1.67-1.65 (m, 1H); 0.94 (2d, 6H); m/z: 472 (M+H)⁺.

Compound 11: 4-{8-(4-(3-isopropyl-3,8-diazabicyclo[3.2.1]octan-8-yl)phenylamino)-imidazo[1,2-a]pyrazin-5-yl}-furan-2-carboxamide

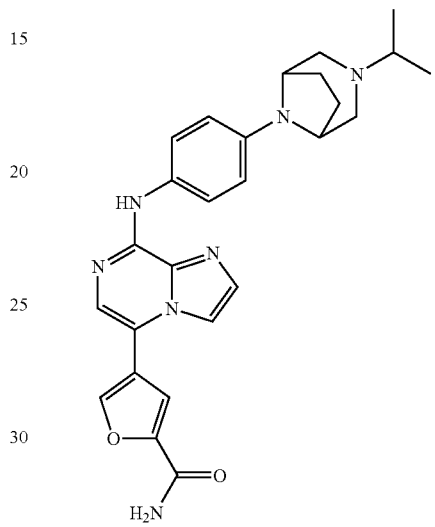

This compound is prepared according to the same procedure as described for Compound 2 using the corresponding intermediates described above.

¹H NMR (400 MHz, DMSO-d6): δ 9.29 (s, 1H); 8.38 (s, 1H); 8.03 (s, 1H); 7.86 (broad s, 1H); 7.72 (d, 2H); 7.69 (s, 1H); 7.55 (s, 1H); 7.54 (s, 1H); 7.47 (broad s, 1H); 6.73 (d, 2H); 4.13-4.11 (m, 2H); 2.47-2.36 (m, 5H); 1.78-1.73 (m, 4H); 0.84 (2d, 6H); m/z: 472 (M+H)⁺.

Compound 12: 4-{8-(4-(8-isopropyl-3,8-diazabicyclo[3.2.1]octan-3-yl)phenylamino)[1,2,4]-triazolo[1,5-a]pyrazin-5-yl}-furan-2-carboxamide

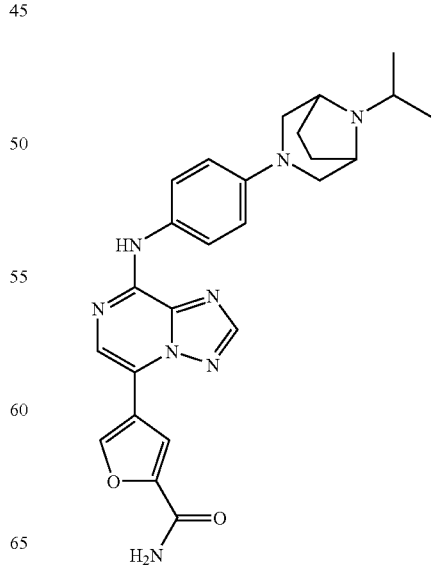

This compound is prepared according to the same procedure as described for Compound 2 using the corresponding intermediates described above.

¹H NMR (400 MHz, DMSO-d6): δ 9.79 (s, 1H); 8.69 (s, 1H); 8.64 (s, 1H); 8.09 (s, 1H); 7.93-7.91 (broad s, 1H); 7.71 (s, 1H); 7.69 (d, 2H); 7.53-7.51 (broad s, 1H); 6.74 (d, 2H); 4.07-4.04 (m, 1H); 3.51-5.48 (m, 2H); 3.10-3.09 (m, 2H); 2.77-2.75 (m, 2H); 1.76-1.74 (m, 2H); 1.59-1.57 (m, 2H); 0.96 (2d, 6H); m/z: 473 (M+H)⁺.

Compound 13: 4-{8-(4-(3-isopropyl-3,8-diazabicyclo[3.2.1]octan-8-yl)phenylamino)[1,2,4]triazolo[1,5-a]pyrazin-5-yl}-furan-2-carboxamide

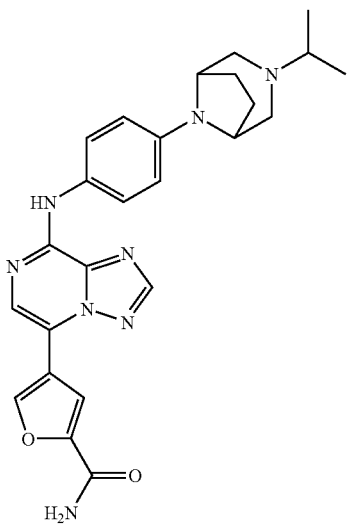

This compound is prepared according to the same procedure as described for Compound 2 using the corresponding intermediates described above.

¹H NMR (400 MHz, DMSO-d6): δ 9.84 (s, 1H); 8.76 (d, 2H); 8.19 (s, 1H); 7.99 (broad s, 1H); 7.90 (s, 1H); 7.79 (d, 2H); 7.59 (broad s, 1H); 6.86 (d, 2H); 4.22-4.25 (m, 2H); 2.56-2.47 (m, 5H); 1.89-1.84 (m, 4H); 0.95 (2d, 6H); m/z: 473 (M+H)⁺.

Compound 14: 4-{8-(4-(8-isopropyl-3,8-diazabicyclo[3.2.1]octan-3-yl)phenylamino)-imidazo[1,2-a]pyrazin-5-yl}-furan-2-carboxamide

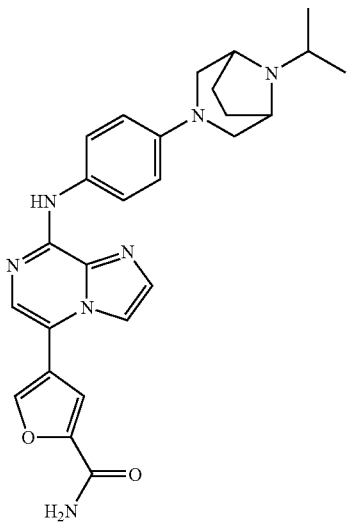

This compound is prepared according to the same procedure as described for Compound 2 using the corresponding intermediates described above.

¹H NMR (400 MHz, DMSO-d6): δ 9.42 (s, 1H); 8.47 (s, 1H); 8.11 (s, 1H); 7.96 (broad s, 1H); 7.81-7.79 (m, 2H); 7.73 (s, 1H); 7.63-7.61 (m, 2H); 7.57 (broad s, 1H); 6.80-6.78 (m, 2H); 3.55-3.53 (m, 2H); 3.34-3.31 (m, 2H); 2.83-2.80 (m, 2H); 2.53-2.51 (m, 1H); 1.82-1.81 (m, 2H); 1.66-1.64 (m, 2H); 1.04 (2d, 6H); m/z: 472 (M+H)⁺.

Compound 15: 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-1H-pyrazole-3-carboxylic acid amide

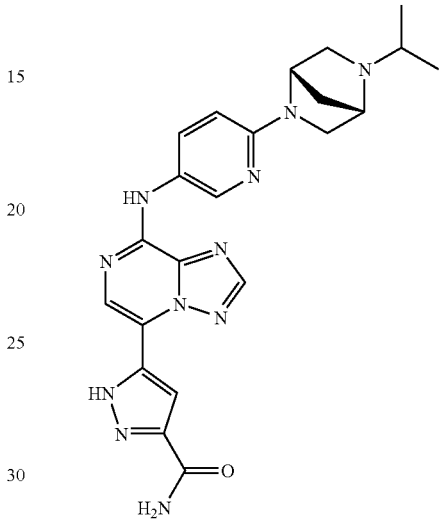

This compound is prepared according to the same procedure as described for Compound 2 using the corresponding intermediates described above.

¹H NMR (400 MHz, DMSO-d6): δ 14.04 (broad s, 1H); 10.06 (s, 1H); 8.79 (s, 1H); 8.68 (s, 1H); 8.22 (s, 1H); 8.04-8.02 (m, 2H); 7.74 (broad s, 1H); 7.69 (broad s, 1H); 6.59-6.57 (m, 1H); 4.58 (s, 1H); 3.76 (s, 1H); 3.49-3.42 (m, 1H); 3.35-3.31 (m, 1H); 3.08-3.06 (m, 1H); 2.49-2.42 (m, 2H); 1.84-1.83 (m, 2H); 0.98 (d, 3H); 0.79 (d, 3H); m/z: 460 (M+H)⁺.

Compound 16: 5-{8-(4-((1S,4S)-5-tert-butyl-2,5-diazabicyclo[2.2.1]heptan-2-yl)phenylamino)-[1,2,4]triazolo-[1,5-a]pyrazin-5-yl}-2,3-dihydro-isoindol-1-one

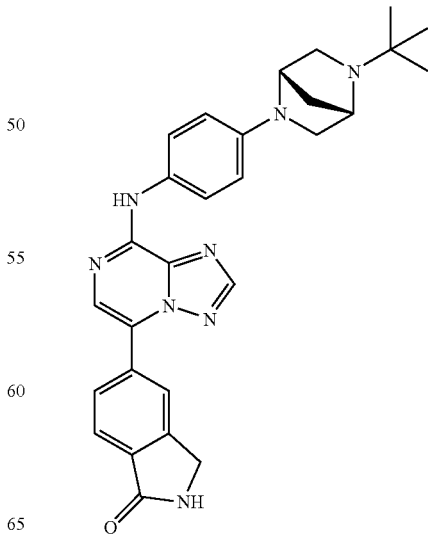

This compound is prepared according to the same procedure as described for Compound 2 using the corresponding intermediates described above.

$^1$H NMR (400 MHz, CDCl$_3$): δ 8.38 (s, 1H); 8.09 (s, 1H); 8.02-7.95 (m, 2H); 7.84 (s, 1H); 7.73 (s, 1H); 7.52 (d, 2H); 6.62 (d, 2H); 6.25 (broad s, 1H); 4.56 (s, 2H); 4.27 (s, 1H); 3.71 (s, 1H); 3.50-3.48 (m, 1H); 3.15-3.10 (m, 2H); 2.88-2.86 (m, 1H); 1.83-1.81 (m, 2H); 1.05 (s, 9H); m/z: 495 (M+H)$^+$.

Compound 17: 5-{8-(4-((1S,4S)-5-tert-butyl-2,5-diazabicyclo[2.2.1]heptan-2-yl)phenyl-amino)-[1,2,4]triazolo[1,5-a]pyrazin-5-yl}-1H-pyrazole-3-carboxylic acid amide

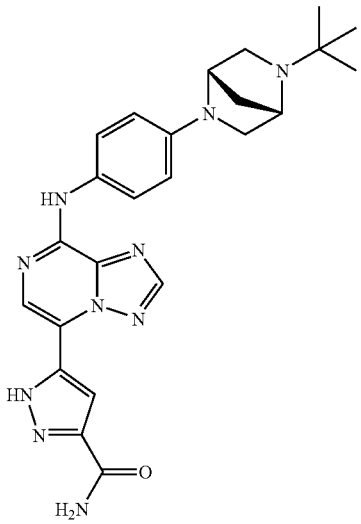

This compound is prepared according to the same procedure as described for Compound 2 using the corresponding intermediates described above.

$^1$H NMR (400 MHz, DMSO-d6): δ 13.82 (broad s, 1H); 9.70 (s, 1H); 8.66 (s, 1H); 8.11 (s, 1H); 7.65 (broad s, 1H); 7.65-7.62 (m, 3H); 7.37 (broad s, 1H); 6.51-6.49 (m, 2H); 4.24 (s, 1H); 3.62 (s, 1H); 3.36-3.35 (m, 1H); 2.83-2.77 (m, 3H); 1.64-1.57 (m, 2H); 0.92 (s, 9H); m/z: 473 (M+H)$^+$.

Compound 18: 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-2,3-dihydro-isoindol-1-one

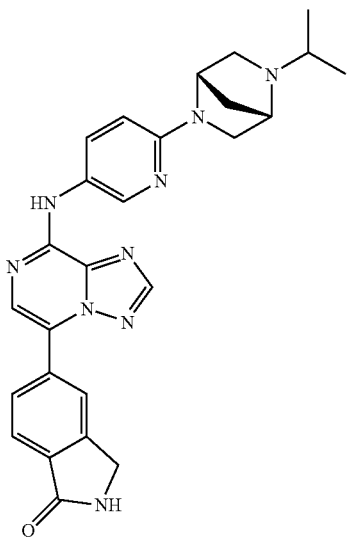

This compound is prepared according to the same procedure as described for Compound 2 using the corresponding intermediates described above.

$^1$H NMR (400 MHz, DMSO-d6): δ 9.89 (s, 1H); 8.61 (s, 1H); 8.59 (broad s, 1H); 8.49-8.47 (m, 1H); 8.11 (s, 1H); 7.99-7.95 (m, 2H); 7.85 (s, 1H); 7.74-7.72 (m, 1H); 6.49-6.47 (m, 1H); 4.48 (s, 1H); 4.41 (s, 2H); 3.65 (s, 1H); 3.41-3.39 (m, 1H); 3.20-3.18 (m, 1H); 2.97-2.95 (m, 1H); 2.40-2.38 (m, 1H); 2.28-2.26 (m, 1H); 1.74-1.72 (m, 2H); 0.93 (d, 3H); 0.86 (d, 3H); m/z: 482 (M+H)$^+$.

Compound 19: 5-(2-ethoxypyridin-4-yl)-N-(4-((1S,4S)-5-isopropyl-2,5-diazabicyclo[2.2.1]heptan-2-yl)phenyl)-[1,2,4]triazolo[1,5-a]pyrazin-8-amine

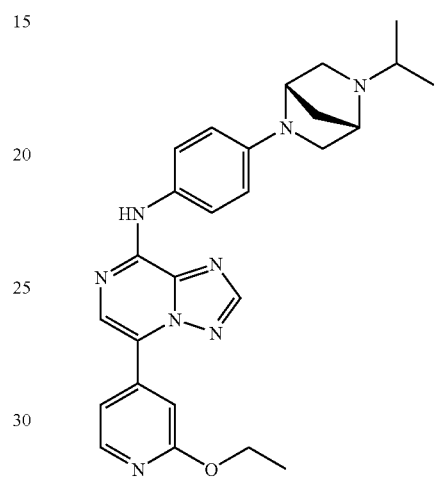

This compound is prepared according to the same procedure as described for Compound 2 using the corresponding intermediates described above.

$^1$H NMR (400 MHz, DMSO-d6): δ 8.37 (s, 1H); 8.28 (d, 1H), 7.92 (s, 1H); 7.79 (s, 1H); 7.61 (d, 2H), 7.42-7.38 (m, 2H), 6.63 (d, 2H); 4.46-4.42 (q, 2H); 4.22 (s, 1H); 3.85 (s, 1H); 3.43-3.40 (m, 2H); 3.24-3.22 (m, 1H); 2.55-2.53 (m, 2H); 2.03-1.99 (m, 2H); 1.42 (t, 3H); 1.08 (d, 3H); 1.04 (d, 3H); m/z: 471 (M+H)$^+$.

Compound 20: 4-(8-(4-((1S,4S)-5-isopropyl-2,5-diazabicyclo[2.2.1]heptan-2-yl)phenylamino)-[1,2,4]triazolo[1,5-a]pyrazin-5-yl)pyridin-2(1H)-one

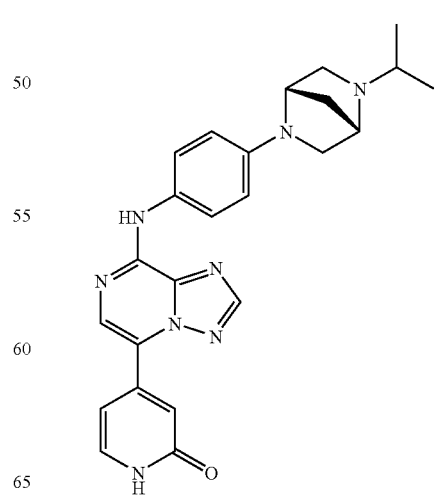

This compound is prepared according to the same procedure as described for Compound 2 using the corresponding intermediates described above.

NMR $^1$H (400 MHz, CDCl$_3$): δ 12.99 (broad s, 1H); 8.37 (s, 1H); 7.95-7.93 (m, 2H); 7.63 (d, 2H); 7.49 (d, 1H); 7.30 (s, 1H); 6.92 (d, 1H); 6.63 (d, 2H); 4.21 (s, 1H); 3.82 (s, 1H); 3.42-3.37 (m, 2H); 3.22-3.19 (m, 1H); 2.56-2.50 (m, 2H); 2.06-2.04 (m, 1H); 1.87-1.76 (m, 1H); 1.07 (d, 3H); 1.03 (d, 3H); m/z: 443 (M+H)$^+$.

Compound 21: Ethyl 5-(8-(4-((1S,4S)-5-isopropyl-2,5-diazabicyclo[2.2.1]heptan-2-yl)phenylamino)-[1,2,4]triazolo[1,5-a]pyrazin-5-yl)-1H-pyrazole-3-carboxylate

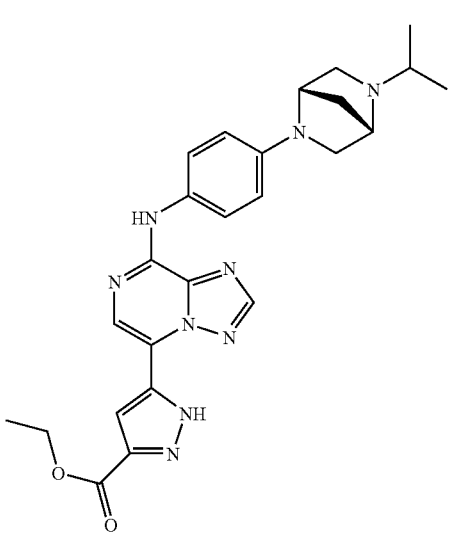

The prepration of this compound is described in step 1 towards compound 5 using the corresponding intermediates described above.

NMR $^1$H (400 MHz, CDCl$_3$): δ 8.53 (s, 1H); 8.20 (s, 1H); 7.79 (s, 1H); 7.64 (d, 2H); 7.39 (s, 1H); 6.62 (d, 2H); 4.47 (q, 2H); 4.21 (s, 1H); 3.81 (s, 1H); 3.41-3.36 (m, 2H); 3.20-3.18 (m, 1H); 2.54-2.49 (m, 2H); 2.04-2.02 (m, 1H); 1.96-1.94 (m, 1H); 1.42 (t, 3H); 1.07 (d, 3H); 1.03 (d, 3H); m/z: 488 (M+H)$^+$

Compound 22: 4-{8-(4-((1S,4S)-5-isopropyl-2,5-diazabicyclo[2.2.1]heptan-2-yl)phenyl-amino)imidazo[1,2-a]pyrazin-5-yl}-1H-pyridin-2-one

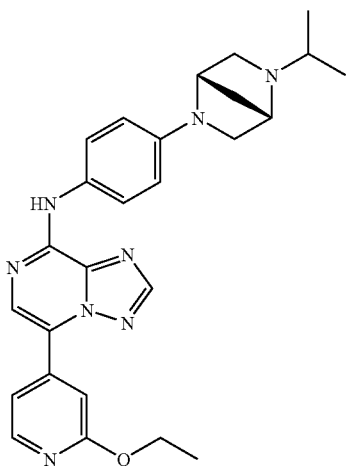

The prepration of this compound is described in step 1 towards compound 8 using the corresponding intermediates described above.

$^1$H NMR (400 MHz, DMSO-d6): δ 9.50 (s, 1H); 8.33 (d, 1H); 8.07 (s, 1H); 7.78-7.70 (m, 2H); 7.57 (s, 1H); 7.33 (d, 2H); 7.10 (s, 1H); 6.62 (d, 2H); 4.42 (q, 2H); 4.27 (s, 1H), 3.68 (s, 1H), 3.34 (s, 1H), 3.18-3.16 (m, 1H), 3.01-2.98 (m, 1H), 2.42-2.96 (m, 2H), 1.84 (s, 2H), 1.41 (t, 3H); 1.04 (d, 3H), 0.96 (d, 3H); m/z: 470 (M+H)$^+$.

Compound 23: 3-(8-(4-((1S,4S)-5-isopropyl-2,5-diazabicyclo[2.2.1]heptan-2-yl)phenylamino)-[1,2,4]triazolo[1,5-a]pyrazin-5-yl)-1,2,4-oxadiazole-5-carboxamide Step 1: 8-(4-((1S,4S)-5-isopropyl-2,5-diazabicyclo[2.2.1]heptan-2-yl)phenylamino)-[1,2,4]triazolo-[1,5-a]pyrazine-5-carbonitrile

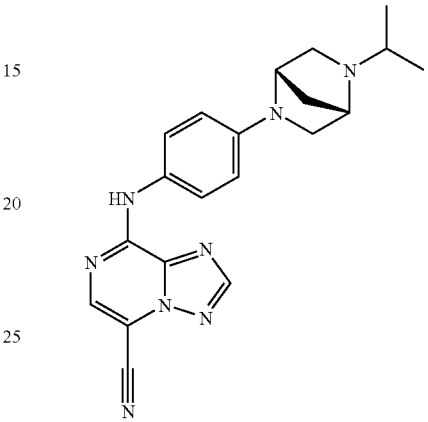

A sealed tube is charged with (5-bromo-[1,2,4]triazolo[1,5-a]pyrazin-8-yl)-[4-((1S,4S)-5-isopropyl-2,5-diazabicyclo[2.2.1]hept-2-yl)phenylamine (compound 2, step1) (0.30 g, 0.70 mmol), potassium ferrocyanide (0.13 g, 0.35 mmol), sodium carbonate (0.037 g, 0.35 mmol), potassium iodide (0.058 g, 0.35 mmol), copper(II) tetrafluoroborate hydrate (0.36 g, 1.05 mmol), DMA (5 mL) and N,N-dimethylethylenediamine (340 μL, 3.15 mmol). The reaction mixture is heated at 85° C. during 18 hours. After return to room temperature, the reaction is partitioned between ethyl acetate and water. Aqueous phase is extracted twice with ethyl acetate. Combined organic phases are washed with water, dried over MgSO$_4$, filtered and evaporated. Purification of the residue by silica gel column chromatography eluting with a mixture of DCM/7N NH$_3$ in methanol (99/1) affords the title compound.

Step 2: 3-(8-(4-((1S,4S)-5-isopropyl-2,5-diazabicyclo[2.2.1]heptan-2-yl)phenylamino)-[1,2,4]triazolo[1,5-a]pyrazin-5-yl)-1,2,4-oxadiazole-5-carboxamide

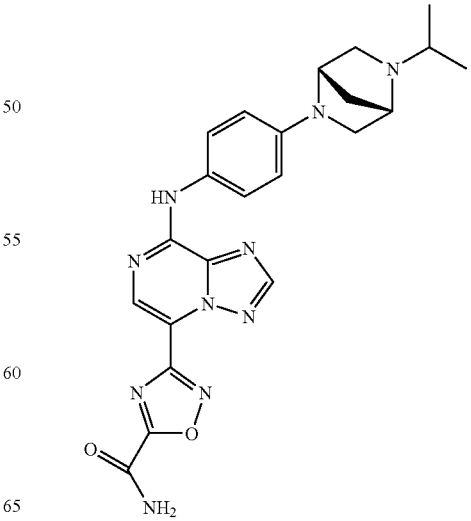

A mixture of the compound obtained in the previous step (26.0 mg, 0.07 mmol), DIPEA (12 µL, 0.07 mmol) and hydroxylamine hydrochloride (5 mg, 0.07 mmol) in ethanol (300 µL) is heated at 85° C. during 18 hours. After return to room temperature, solvent is evaporated to dryness and the residue is dissolved in pyridine (400 µL). The solution is cooled down to 0° C. and ethyl oxalyl chloride (24 µL, 0.21 mmol) is added then the reaction is heated to 70° C. for 2 hours. After return to room temperature, iced water is added and left to stir for 30 min. DCM (5 mL) is added and the aqueous phase is extracted twice. Combined organic phases are dried over MgSO$_4$, filtered and evaporated. Purification of the residue by silica gel column chromatography eluting with a mixture of DCM/7N NH$_3$ in methanol (99/1 to 98/2) affords the title compound.

NMR $^1$H (400 MHz, CDCl$_3$): δ 8.57 (s, 1H); 8.51 (s, 1H); 8.11 (s, 1H); 7.64 (d, 2H); 7.10 (s, 1H); 6.63 (d, 2H); 6.08 (s, 1H); 4.22 (s, 1H); 3.83 (s, 1H); 3.42-3.39 (m, 2H); 3.22-3.19 (m, 1H); 2.54-2.51 (m, 2H); 2.04-2.02 (m, 1H); 1.95-1.90 (m, 1H); 1.08 (d, 3H); 1.03 (d, 3H); m/z: 461 (M+H)$^+$.

Compound 24: 4-(8-(3-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide

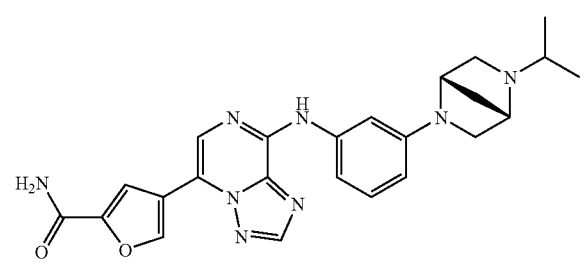

This compound was prepared according to the same procedure as described for Compound 2 using the corresponding intermediates described above.

NMR δ $^1$H (400 MHz, DMSO-d$^6$): 9.71 (s, 1H), 8.72 (s, 1H), 8.65 (s, 1H), 8.17 (s, 1H), 7.92 (brs, 1H), 7.73 (s, 1H), 7.51 (brs, 1H), 7.32 (d, 1H), 7.29 (s, 1H), 7.08 (m, 1H), 6.27 (d, 1H), 4.18 (s, 1H), 3.62 (s, 1H), 3.24 (d, 1H), 3.16 (d, 1H), 2.98 (d, 1H), 2.44-2.39 (m, 2H), 1.76 (s, 2H), 0.92 (d, 3H), 0.89 (d, 3H);

Compound 25: 4-(8-(3-((1S,4S)-5-isopropyl-2,5-diazabicyclo[2.2.1]heptan-2-yl)phenylamino)imidazo[1,2-a]pyrazin-5-yl)furan-2-carboxamide

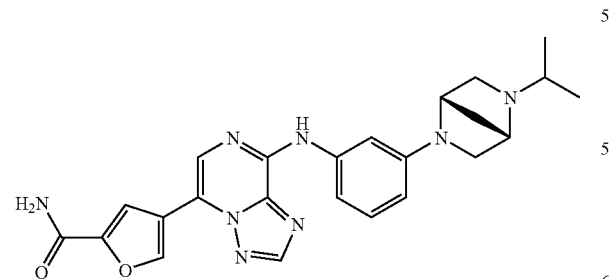

This compound was prepared according to the same procedure as described for Compound 2 using the corresponding intermediates described above.

NMR δ $^1$H (400 MHz, DMSO-d$^6$): 9.23 (s, 1H), 8.42 (s, 1H), 8.07 (s, 1H), 7.87 (brs, 1H), 7.69 (s, 1H), 7.61 (s, 1H), 7.58 (s, 1H), 7.48 (brs, 1H), 7.38 (m, 1H), 7.21 (s, 1H), 7.02 (t, 1H), 6.21 (d, 1H), 4.15 (s, 1H), 3.64 (s, 1H), 3.32 (d, 1H), 3.14 (d, 1H), 2.95 (d, 1H), 2.36-2.32 (m, 2H), 1.75 (s, 2H), 0.92 (d, 3H), 0.85 (d, 3H);

Compound 26: 5-(8-(3-((1S,4S)-5-isopropyl-2,5-diazabicyclo[2.2.1]heptan-2-yl)phenylamino)-[1,2,4]triazolo[1,5-a]pyrazin-5-yl)isoindolin-1-one

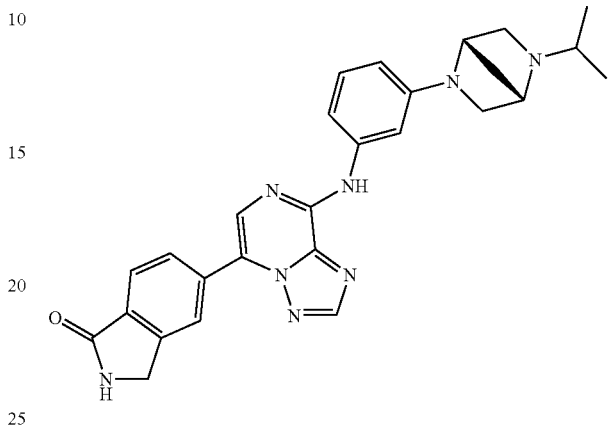

This compound was prepared according to the same procedure as described for Compound 2 above using the corresponding intermediates described above.

NMR δ $^1$H (400 MHz, DMSO-d$^6$): 9.87 (s, 1H), 8.71 (m, 2H); 8.24 (m, 1H), 8.12 (m, 1H), 8.01 (m, 1H), 7.81 (m, 1H), 7.43 (m, 1H), 7.24 (m, 1H), 7.12 (m, 1H), 6.37 (m, 1H); 4.50 (s, 2H); 4.25 (s, 1H); 3.74 (s, 1H); 3.44 (m, 1H), 3.21 (m, 1H); 3.03 (m, 1H); 2.43-2.46 (m, 2H); 1.85 (s, 2H); 0.96 (d, 6H);

Compound 27: 4-[8-({4-[(1R,4R)-5-isopropyl-2,5-diazabicyclo[2.2.1]hept-2-yl]phenyl}amino)[1,2,4]triazolo[1,5-a]pyrazin-5-yl]-2-furamide

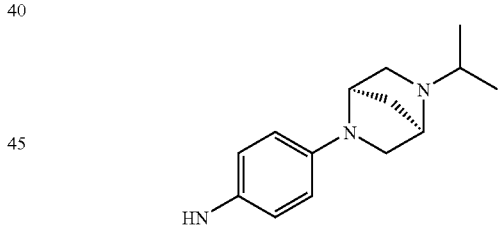

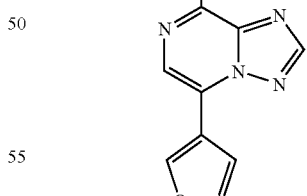

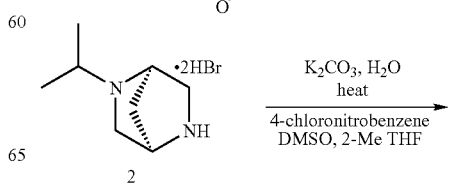

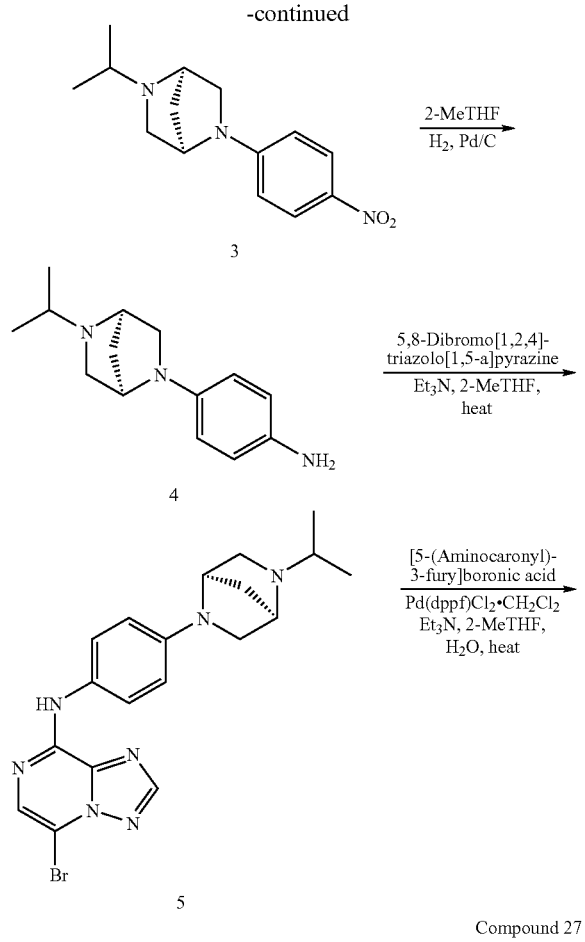

Compound 27

Step 1: (1R,4R)-2-Isopropyl-5-(4-nitrophenyl)-2,5-diazabicyclo[2.2.1]heptane (3)

To a mixture of (1R,4R)-5-Isopropyl-2,5-diazabicyclo[2.2.1]heptane dihydrobromide (2); 3.0 g; 9.9 mmol), 4-chloronitrobenzene (1.7 g; 11 mmol), dimethylsulfoxide (6.2 mL), and tap water (2.5 mL) is added solid $K_2CO_3$ (1.7 g; mmol; gas evolution). The resulting suspension is heated to 50° C., after which 2-MeTHF (0.5 mL) and more solid $K_2CO_3$ (1.9 g; mmol) are added. Reaction temperature is increased to 125° C. and the reactor contents are held at this temperature overnight. The reaction mixture is cooled down to ambient temperature, after which tap water (25 mL) is added. Extraction of the aqueous mixture with ethyl acetate (3×30 mL) and concentration of the combined organic extracts in vacuo give a solid residue, which is redissolved in hot MTBE (300 mL). The hot solution is filtered to remove residual solids and concentrated in vacuo to furnish crude (2). Purification is accomplished by partitioning the crude material between ethyl acetate (70 mL) and dilute hydrochloric acid (pH 1; 250 mL), separating the layers, washing of the aqueous phase with ethyl acetate (2×50 and 2×100 mL), extraction of the combined organic layers with dilute hydrochloric acid (pH 1; 100 mL), basification of the combined aqueous layers with 10 N aqueous NaOH to pH 10, extraction of the alkaline aqueous layer with MTBE (2×200 mL) and ethyl acetate (2×200 mL), drying over $Na_2SO_4$, and concentration in vacuo to give a white solid. This solid is reslurried in heptane/MTBE 1:1 v/v (20 mL), the resulting suspension filtered and the filter cake washed with heptane/MTBE 1:1 v/v (20 mL) and air dried to give (3) as a white solid. LC-purity: 99.3 area-%.

Step 2: 4-[(1R,4R)-5-Isopropyl-2,5-diazabicyclo[2.2.1]hept-2-yl]aniline (4)

A solution of 3 (1.6 g; 6 1 mmol) in 2-MeTHF (25 mL) is stirred under a 1 bar hydrogen atmosphere in the presence of Pd/C catalyst (10% Degussa type E101 NE/W; 0.1 g) at 30° C. for a period of 3 h. The catalyst is filtered off over a bed of Dicalite 478 and the filter cake washed with 2-MeTHF (2×10 mL). The filtrate is concentrated in vacuo to a volume of 25 mL and the resulting solution is used as such in the next step.

Step 3: 5-Bromo-N-{4-[(1R,4R)-5-isopropyl-2,5-diazabicyclo[2.2.1]hept-2-yl]phenyl}[1,2,4]triazolo[1,5-a]pyrazin-8-amine (5)

To the solution obtained from step 2 is added 5,8-dibromo[1,2,4]triazolo[1,5-a]-pyrazine (1.6 g; 5.8 mmol) and triethylamine (3.4 mL). The resulting mixture was heated at reflux for 70 h, after which the reactor contents were cooled down and filtered to remove solids. The filter cake was washed with 2-MeTHF (2×5 mL) and the filtrate used as such in the next step.

Step 4: Compound 27 4-[8-({4-[(1R,4R)-5-Isopropyl-2,5-diazabicyclo[2.2.1]hept-2-yl]phenyl}amino)[1,2,4]triazolo[1,5-a]-pyrazin-5-yl]-2-furamide (6)

To the solution obtained from step 3 is added 2-MeTHF (5 mL), tap water (6.5 mL), [5-(aminocarbonyl)-3-furyl]boronic acid (1.3 g; 8.6 mmol), and $Pd(dppf)_2Cl_2$ (0.26 g; 0.3 mmol). The resulting mixture is degassed 5 times by means of a vacuum/nitrogen purge cycle and heated at 80° C. for 6 h. The reactor contents are then cooled down to ambient temperature, 1,2-diamino-propane (2 mL) is added, the resulting suspension filtered (slow!), and the filter cake washed with 2-MeTHF (6×5 mL) to obtain crude compound 27 as a green solid. The crude material is reslurried in methanol (15 mL), filtered, and the filter cake washed with methanol (5 mL). The filter cake is then mixed with water/acetic acid (pH 1; approx. 50 mL), the resulting suspension filtered until a clear filtrate is obtained, and the filter cake washed with water until the washing liquid turned colorless. The combined filtrate and washing liquids are concentrated in vacuo at 50° C. to remove water, the residue stripped with 2-propanol (twice) and toluene (three times) and subsequently taken up in methanol (70 mL) and toluene (5 mL). To the resulting suspension is added 1,2-diaminopropane (2 mL) and dppe (0.08 g; 0.2 mmol), after which stirring is continued overnight. The purified product is isolated by filtration, washing of the filter cake with methanol until the washing liquid turns pale yellow, followed by washing with ethyl acetate, and dried at 40° C. in vacuo to compound 27 as a yellow solid.

LC-purity 98.6 area-%.
LC-MS: m/z=459 (100) [M+H]+.

Purification Conditions and Characterization

Routinely, post-synthesis all compounds may be purified using reverse phase HPLC using a Gilson preparative HPLC system (322 pump, 155 UV/VIS detector, 215 liquid handler). The Gilson 215 acts as both auto-sampler and fraction collector. Compounds can also be purified by flash chromatography on silica gel.

Compounds are characterised by mass spectrometry using single quadrupole instrumentation with an electrospray source.

BIOLOGICAL EXAMPLES

Example 1

MAPKAP-K5 Assay

MAPKAP-K5 reactions are performed in FlashPlate format using 0.1 or 0.2 µCi 33P-ATP; 0.6 µM ATP; 1 mU MAP- KAP-K5; 3 µM MAPKAP-K5 peptide substrate, incubated at room temperature for 30 minutes.

Flashplate assay:

The MAPKAP-K5 kinase reaction is performed in a 384 well polypropylene plate (Matrix Technologies) and then transferred to a streptavidin-coated 384 well flashplate (Perkin-Elmer). To wells containing 2 µL test compound or standard inhibitor, 13 µL Enzyme mix or diluent are added using a Hydra (Robbins Scientific). Reactions are started by addition of 10 µL of [2.5×] substrate cocktail using a Multidrop (Thermo-Labsystems), to give final concentrations in the assay of:

1 mU MAPKAP-K5
3 µM MAPKAP-K5 peptide substrate
0.6 µM ATP
0.004 µCi [33P]-γ-ATP/µL
1× reaction buffer Plates are incubated at room temperature for 30 minutes. Reactions are terminated by the addition of 25 µL EDTA (50 mM) to each well using a Micro-fill (Biotek). Reactions are transferred to a streptavidin-coated flashplate using a Zymark robotic system. Plates are incubated for 60 minutes at room temperature. All wells are washed 3 times with 100 µl phosphate buffered saline using a Tecan plate washer. Radioactivity is determined by scintillation counting of the flashplate (empty wells) on a Packard TopCount.

Enzyme Mix:
Enzyme
50 mM Tris Hcl (pH 7.5)
0.1 mM EGTA
2 mM DTT
1 mg/mL BSA

Reaction Buffer:
50 mM Tris Hcl (pH 7.5)
0.1 mM EGTA
10 mM Magnesium acetate
2 mM DTT

Example 2

Development of an Assay for the Identification of Regulators of the Expression of MMP1 by Activated Primary Synovial Fibroblasts To identify compounds that decrease the ECM-degrading activity of cells, the ECM-degrading activity of cells may be induced to allow proper detection of this activity, and to achieve a clearer read-out. In the context of RA, the cells of choice are mammalian synovial fibroblasts and the triggers that may be used to induce the ECM-degrading activity are cytokines relevant in the field of arthritis: for instance TNF-α, IL1β, IL6, OSM, IL17, and MIF1-α. This list is not comprehensive due to the plethora of cytokines potentially involved in the RA pathogenesis (Smolen and Steiner, 2003). To set up an in vitro assay that is as close as possible to the complexity of the pathology, the trigger applied should be a mixture of factors generated by contacting cytokine-producing cells relevant in the field of arthritis, such as monocytes, macrophages, T-cells, and B-cells, with a trigger. The cytokine-producing cells will respond to the contact by producing a complex and unbiased mixture of factors. If the cytokine-producing cell used is also found in a pannus, and the cytokine applied to produce this trigger is found in the synovial fluid of rheumatoid arthritis patients, the mixture of factors ultimately produced will contain part of the factors that are present in the joints of arthritis patients.

Principle of the 'MMP assay'

Matrix Metallo Proteases (MMPs) possess various physiological roles, as e.g. the maturation of other proteases, growth factors, and the degradation of extra-cellular matrix components. MMP1 is one of the members of the MMP family that is able to degrade native collagen, the main component of bone and cartilage. An increased expression of MMP1 by synovial fibroblasts (SFs) is diagnostic for the progression of the arthritic disease and is predictive for erosive processes in the joint (Cunnane et al., 2001). The expression of MMP1 by SFs can be increased by the activation of SFs with triggers relevant for rheumatoid arthritis, as cytokines like TNF-α or IL1β (Andreakos et al., 2003). Taken together, measurement of the levels of MMP1 produced by activated SFs is a readout that is highly relevant in the context of RA as this event reflects the level of activation of SFs towards an erosive phenotype as it is seen in the pannus. If a reduced expression of a candidate drug target in activated SFs leads to the reduction of MMP1 expression by these cells, the drug target is then proven to be involved in the regulation of MMP1 expression and thus considered relevant for the development of therapeutic strategies for the treatment of RA.

In the following examples, the development of an assay, further referred to as 'MMP assay', monitors the MMP1 production by synovial fibroblasts (SFs) in response to diverse activating triggers (Example 2.1). The use of this assay is then described for the validation of gene products that are considered drug targets for the development of RA therapies (Example 2.2). The validation of drug targets is performed using recombinant adenoviruses, further referred to as knock-down viruses or Ad-siRNAs, that mediate the expression in cells of shRNA's which reduce the expression levels of targeted genes by a RNAi (RNA interference)-based mechanism (see WO 03/020931). The identification of compounds modulating the activity of the validated drug targets is then described in Table 3. The use of the 'MMP assay' for the testing of compounds that modulate the activity of the drug targets identified is described further below.

Assay Examples

Control viruses used:

The control viruses used in these studies are listed below. dE1/dE2A adenoviruses are generated from these adapter plasmids by co-transfection of the helper plasmid pWEAd5AfIII-rITR.dE2A in PER.E2A packaging cells, as described in WO99/64582.

Negative control viruses:
Ad5-eGFP_KD: Target sequence: GCTGACCCTGAAGT-TCATC (SEQ ID NO: 1). Cloned using Sap1-sites into vector and virus generated as described in WO03/020931.
Ad5-Luc_v13_KD: Target sequence GGTTACCCTAAGGGT-GTGGC (SEQ ID NO: 2). Cloned using Sap1-sites into vector and virus generated as described in WO03/020931.
Ad5-M6PR_v1_KD: Target sequence CTCTGAGTGCAGT-GAAATC (SEQ ID NO: 3). Cloned using Sap1-sites into vector and virus generated as described in WO03/020931.

Positive control viruses:
Ad5-MMP1_v10_KD: Target sequence ACAAGAGCAA-GATGTGGAC (SEQ ID NO: 4). Cloned using Sap1-sites into vector and virus generated as described in WO03/020931.

Viruses used for target validation:
Ad5-MAPKAPK5_v13_KD: Target sequence CGGCACTT-TACAGAGAAGC (SEQ ID NO: 5). Cloned using Sap1-sites into vector and virus generated as described in WO03/020931.

Ad5-MAPKAPK5_v12_KD: Target sequence ATGATGT-GTGCCACACACC (SEQ ID NO: 6). Cloned using Sap1-sites into vector and virus generated as described in WO03/020931.

Example 2.1

Development of the MMP Assay

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 µg/mL anti-MMP1 antibody MAB1346 (Chemicon). The antibody is diluted in buffer 40 (1.21 g Tris base (Sigma), 0.58 g NaCl (Calbiochem) and 5 ml 10% $NaN_3$ (Sigma) in 1 L milliQ water and adjusted to pH 8.5). After overnight incubation at 4° C., plates are washed with PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well Casein buffer (2% Casein (VWR International) in PBS). Next day, casein buffer is removed from ELISA plates and replaced by 50 µL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 ml 0,5 M EDTA pH 8 (Invitrogen), 5 ml 10% $NaN_3$ in 1 L milliQ and adjusted to pH 7.0). 0.25 mM DTT (Sigma) is added to the thawed samples plates. After removal of the EC buffer, 20 µL of sample is transferred to the ELISA plates. After overnight incubation at 4° C. plates are washed twice with PBS and once with PBST (PBS with 0.05% Tween-20 (Sigma)) and incubated with 35 µL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0,5M EDTA pH 8 in 2 L milliQ and adjusted to pH 7.0) at a concentration of 5 µg/mL. After 2 h of incubation at RT, plates are washed as described above and incubated with 50 µL/well streptavidin-HRP conjugate (Biosource). Streptavidin-HRP conjugate is diluted in buffer C at a concentration of 0.25 µg/mL. After 45 min, plates are washed as described above and incubated for 5 min with 50 µL/well BM Chem ELISA Substrate (Roche). Readout is performed on the Luminoscan Ascent Luminometer (Labsystems) with an integration time of 200 msec or with an Envision reader (Perkin Elmer).

Figure 2:
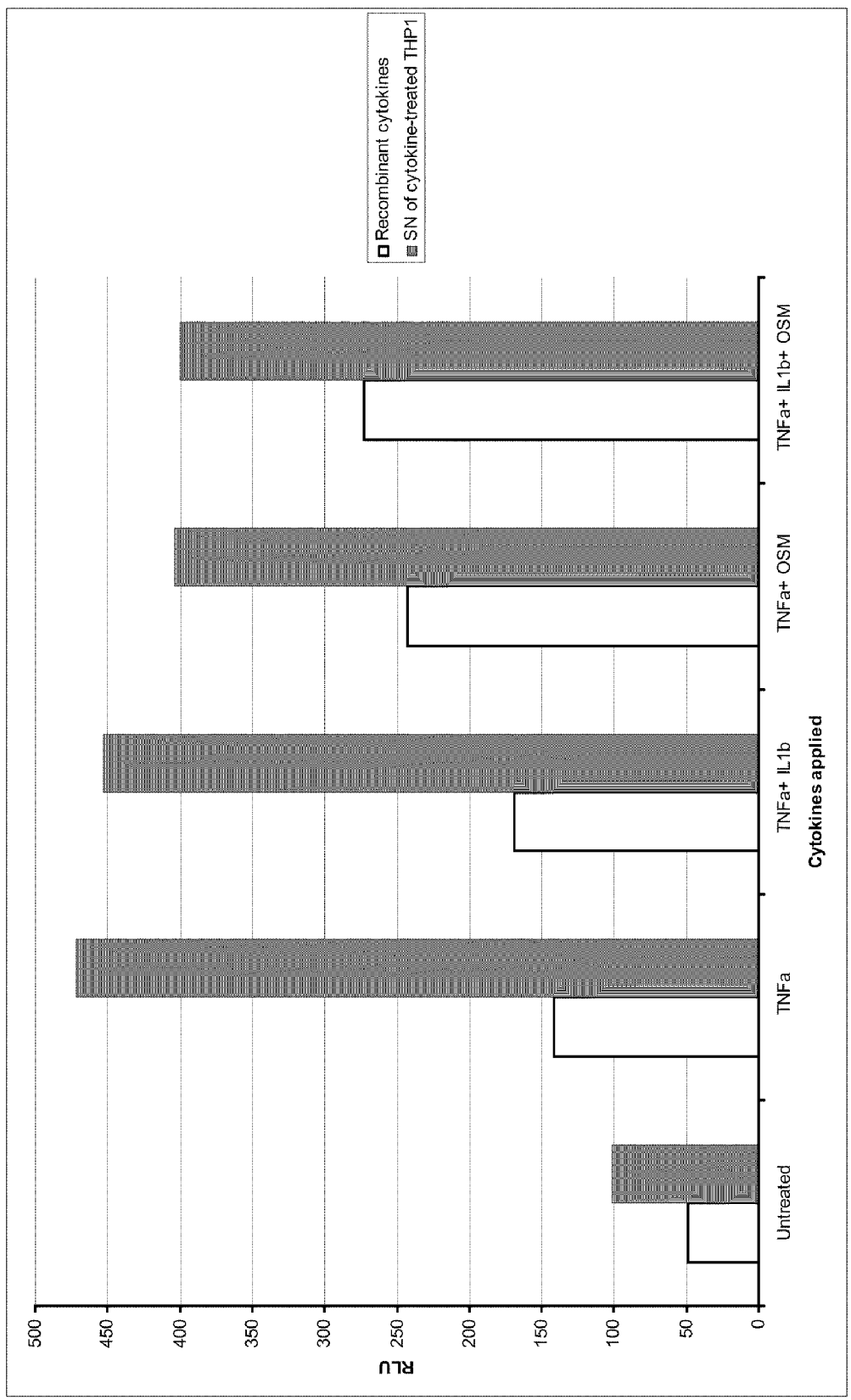
FIG. 2. This chart shows the increased expression of MMP1 in synovial fibroblasts triggered with cytokines involved in rheumatoid arthritis pathology.

The increase of MMP1 expression by SFs upon treatment with cytokines relevant in the field of RA (TNF-α, IL1β and OSM) or a combination thereof is shown in FIG. 2 as white bars. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/mL. 72 h after cytokine addition, the supernatant is collected and processed in the MMP1 ELISA as described in the protocol given above. In parallel with this experiment, SFs are triggered, using the same protocol, with the supernatant of THP1 cells (2-fold diluted in M199+1% FBS) treated with the same cytokines or combinations of cytokines for 48 h in M199 medium+1% FBS. MMP1 levels for these samples are shown in FIG. 2 as grey bars. The induction of the MMP1 expression by SFs triggered with the supernatants of TNF-α-treated THP1 cells is stronger (>4.5 fold induction) as compared to the SFs triggered with recombinant TNF-α alone (3-fold induction) and almost equals the 5-fold induction obtained by a mixture of 3 purified cytokines (TNF-α, IL1βb, OSM). This result indicates that the supernatant of TNF-α-induced THP1 cells contains, besides TNF-α, additional pro-inflammatory factors that activate SFs towards MMP1 expression. As the role of TNF-α in the RA pathogenesis is validated (TNF-α-blockers such as Infliximab and Etanercept show some efficacy in the treatment of RA patients) and the THP-1 cells are representative for monocytes/macrophages present in the joint of RA patients, the TNF-α-based trigger mixture prepared by contacting THP-1 cells with TNF-α will contain factors present in the joints of RA patients and subsequently is relevant to RA. This TNF-α-based complex trigger, further referred to as the 'complex trigger', will further be used as basis for the 'MMP assay'.

Figure 3:
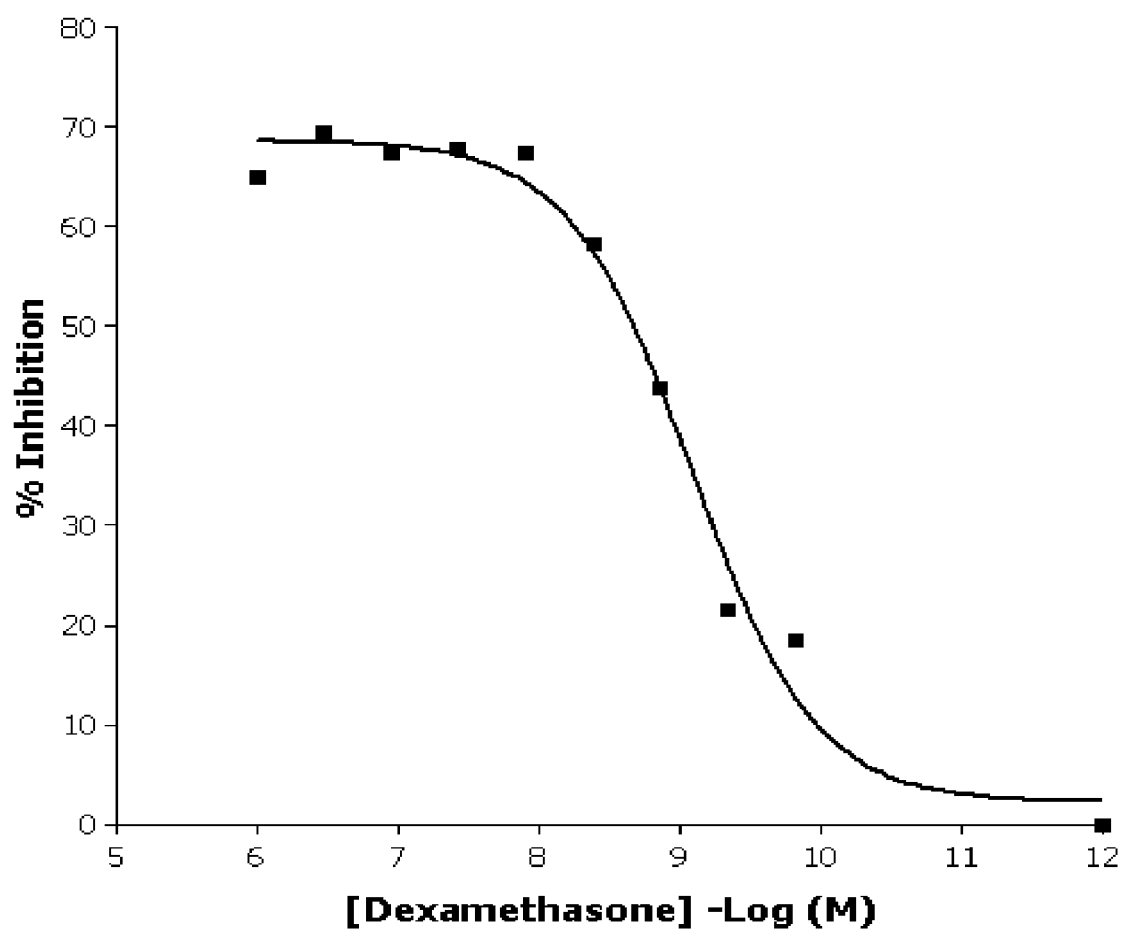
FIG. 3. This graph shows the dose-dependent inhibition of the "TNF-α-based trigger"-induced expression of MMP1 by SFs by a known anti-inflammatory compound.

Inhibition of the activation of SF by the 'complex trigger' is shown using dexamethasone, a potent anti-inflammatory agent that also strongly reduces collagen-induced arthritis in rodents (Yang et al., 2004) (FIG. 3). Dexamethasone is shown to dose-dependently reduce amounts of MMP1 produced by complex trigger activated SFs. SFs are seeded at a density of 3000 cells/well in 96 well plates. 24 hrs after seeding, increasing concentrations of dexamethasone are added to the cells. After overnight incubation, medium of every well is refreshed to supernatant of THP-1 cells treated with TNF-α (50% diluted in M199+0.5% FBS), and the same concentration of dexamethasone as added the day before. 48 hrs after treatment, the supernatant is collected and subjected to the MMP1 ELISA described above. The addition of dexamethasone clearly reduced the MMP1 expression by SFs, with an $IC_{50}$ value of about 1 nM (see FIG. 3). These data show that the MMP1 expression by activated SFs can be reduced by the addition of a physiologically relevant inhibitor and represent a proof of principle for the 'MMP assay'.

Example 2.2

MAPKAPK5 Modulates SF 'Complex Trigger'-Induced MMP1 Expression (A) Ad-siRNA Virus Functions to Knock Down MAPKAPK5 Expression.

Recombinant adenoviruses mediating the expression of siRNA's targeting MAPKAPK5 and eGFP are generated according to the procedure described in WO03/020931. The target sequence used in the recombinant adenovirus is: CGGCACTTTACAGAGAAGC (SEQ ID NO: 5) as well as ATGATGTGTGCCACACACC (SEQ ID NO: 6). The target sequence within the eGFP mRNA used in the recombinant adenovirus is: GCTGACCCTGAAGTTCATC (SEQ ID NO: 1). These sequences are cloned into the adapter plasmid using Sap1 sites. dE1/dE2A adenoviruses are generated from these adapter plasmids by co-transfection of the helper plasmid pWEAd5AflII-rITR.dE2A in PER.E2A packaging cells, as described in WO99/64582.

Figure 4:
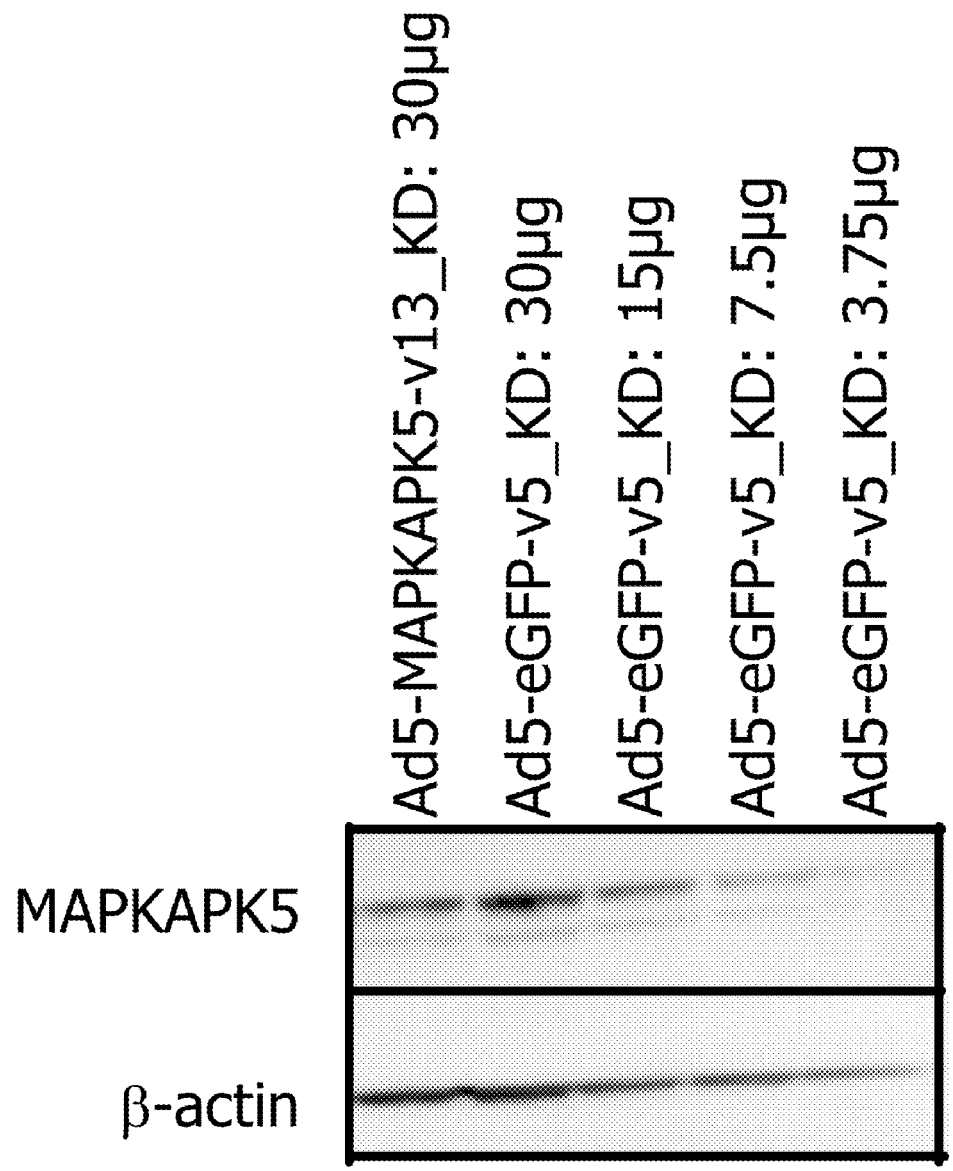
FIG. 4. This gel shows the reduction, at the protein level, of the expression of MAPKAPK5 in SFs by infection of the cells with Ad-siRNA virus targeting MAPKAPK5.

The functionality of an adenovirus targeting MAPKAPK5 is tested as follows. These adenoviruses are used to infect primary human SFs cultured in petri dishes as follows. On day 1, 500.000 SFs are seeded per petri dish. One day later, the cells are infected with Ad5-MAPKAPK5-v13_KD (1.6E9 VP/mL) or Ad5-eGFP-v5_KD (1.3E10 VP/mL) at an MOI of 4000 (based on the titers (number of virus particles per mL) defined for the viruses by Q-rt-PCR). On day 7, cells are detached from the petri dish according to standard procedure using a trypsin EDTA solution. The trypsin is then neutralized by addition of DMEM growth medium supplemented with 10% FBS. The cells are then collected by a centrifugation step (1000 rpm, 5 min). The pellet is lysed in 100 µL of fresh RIPA buffer (50 mM Tris pH7.5, 150 mM NaCl, 1% deoxycholate, 1% Triton X100, 0.1% SDS). The samples are then sonicated for 10 sec. The protein concentration of the samples is then determined using the BCA kit (Pierce, Cat No 23227) as described by the provider, using BSA as a standard. To 30 μg of cell lysate diluted to 19.5 μl in RIPA buffer, 3.5 μL of reducing agent (NuPage reducing agent No 10, Invitrogen NP0004) and 7.5 μL of sample buffer (NuPage LDS sample buffer, Invitrogen NP0007) are added. The 30 μL sample is then boiled for 5 min and loaded on a 10% polyacrylamide gel (Invitrogen NP0301). To allow the estimation of the level of protein knock-down, 15 μg, 7.5 μg and 3.75 μg of the lysate of the Ad5-eGFP-v5_KD infected cells are also loaded onto the gel. The gel is then run for 2 hours at 100 V in 1×MOPS/SDS NuPage running buffer (Invitrogen NP001). 10 μl of Seablue Plus Prestained standard (Invitrogen LC5925) is used to estimate protein size on the gel. The proteins on the gel are then transferred onto a PVDF membrane (Invitrogen LC2002) by a wet blotting procedure using a transfer buffer prepared by mixing 100 ml Nupage Transfer buffer 20* (NP0006-1), 400 mL methanol and 150 0mL Milli Q water. Before the transfer, the membrane is first soaked in methanol and in transfer buffer. The transfer is performed at 100 V for 90 minutes. The membrane is then blocked by 30 min soaking in blocking buffer (2% blocking blocking powder (Amersham, RPN 2109) prepared in PBST (PBS supplemented with 0,1% Tween 20 (Sigma, P1379)). After blocking, the immunodetection is performed using a mouse monoclonal antibody against MAPKAPK5 (BD Biosciences, Cat No 612080) diluted 250 fold in blocking buffer. After overnight incubation with this primary antibody, the membrane is washed 3 times with PBST and incubated 1 hr with the secondary antibody ((Polyclonal goat anti-mouse Ig, HRP conjugated (DAKO P0447) diluted 50000 fold in blocking buffer. The blot is then washed 3 times in PBST and the detection is performed with ECL advance (RPN2109, Amersham) on a Kodakimager according to the manufacturers instructions. The Western Blotting revealed a lower expression level of MAPKAPK5 in the Ad5-MAPKAPK5-v13_KD infected cells compared to the cells infected with the Ad5-eGFP-v5_KD negative control virus. Comparison with the diluted Ad5-eGFP-v5_KD infected samples allowed to estimate the reduction in expression to be 2-fold. Equal loading of the 30 μg samples is demonstrated by immunodetection of β-actin after removal of the MAPKAPK5 antibody by a 'stripping procedure' (5 minutes boiling of the membrane in PBST). Immunodetection of β-actin is performed according to the method described for MAPKAPK5 detection, but using a goat polyclonal antibody against β-actin (Santa Cruz, Cat No SC-1615) at a 1000 fold dilution as primary antibody and a rabbit anti goat antibody at a 50000 fold dilution as a secondary antibody. Results of this experiment are given in FIG. 4. Taken together, this experiment demonstrated the functionality of the Ad-siRNA virus produced to reduce the MAPKAPK5 expression levels in primary human SFs.

(B) MAPKAPK5 Knock-Down Ad-siRNA Reduces SF-Induced MMP1 Expression

Figure 5:
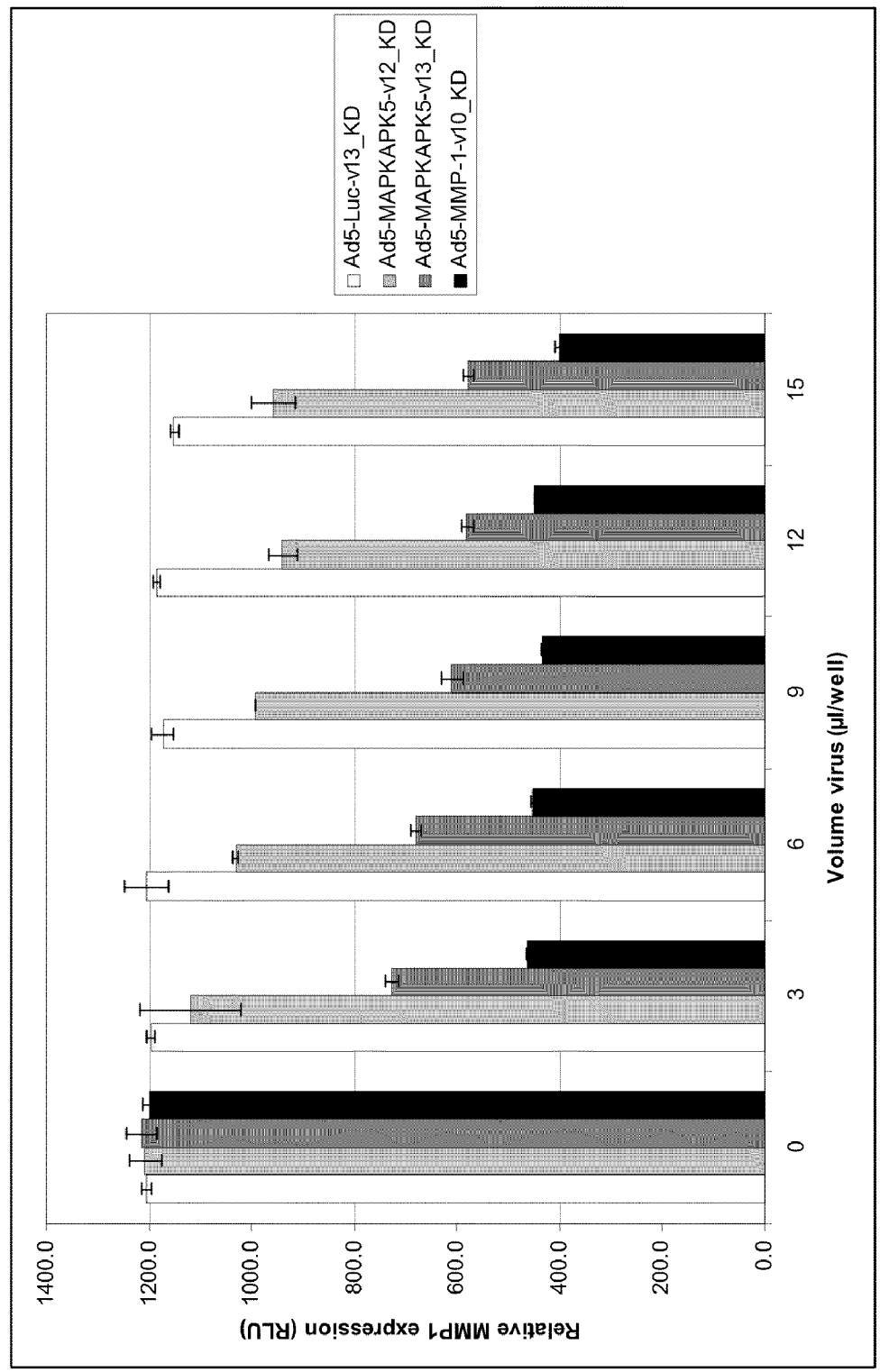
FIG. 5. This chart shows the reduction of 'complex trigger' induced levels of MMP1 expression by SFs by an Ad-siRNA virus targeting MAPKAPK5.

The efficacy of Ad5-MAPKAPK5-v13_KD virus in the 'MMP assay' is tested as follows. Day 1, SFs (passage 9 to 10) are seeded in 96 well plates at a density of 3000 cells per well in complete synovial growth medium (Cell Applications). One day later, the cells are infected with increasing amounts (3, 6; 9, 12 or 15 μl) of following viruses: Ad5-eGFP-v5_KD, Ad5-MAPKAPK5-v12_KD, Ad5-MAPKAPK5-v13_KD, Ad5-MMP1-v10_KD. The virus load is corrected by addition of the neutral virus Ad5-Luc-v13_KD to bring the final virus volume on the cells to 15 μL in every well. This correction guarantees that the effects observed do not result from the virus load applied to the cells. The cells are then incubated for 5 days before the activation step. This step involves the replacement, in every well, of the growth medium by 75 μL of M199 medium supplemented with 25 μL of 'complex trigger'. 48 hrs after the activation step, the supernatant is collected and subjected to the MMP1 ELISA as described in Example 1. The results of the experiment are shown in FIG. 5. The quality of the experiment is demonstrated by the efficacy of the Ad-siRNA virus targeting MMP1 itself. This positive control virus strongly reduces the MMP1 expression by SFs, whereas the negative control virus, designed to target the expression of luciferase, does not influence the levels of MMP1 expression. Two viruses used to validate the MAPKAPK5 target (Ad5-MAPKAPK5-v12_KD and Ad5-MAPKAPK5-v13) do also lead to a clear reduction of the complex trigger induced MMP1 expression by primary human SFs. It can be concluded, from this experiment, that MAPKAPK5 represents a valuable drug target that is shown to modulate MMP1 expression in SFs. Similarly, the inhibition of MAPKAPK5 enzymatic activity by a small molecule compound is expected to reduce the 'complex cytokine' induced MMP1 expression in the 'MMP assay'. The inhibition of MAPKAPK5 enzymatic activity by a small molecule compound is also predicted to reduce the degradation of the joint associated with RA.

(C) In Vitro 'MMP Assay' Testing of Compounds Inhibiting MAPKAPK5

Compounds inhibiting the MAPKAPK5 activity in a biochemical assay (i.e. cell free, using purified enzyme), are tested in the 'MMP assay' according to following protocol.

The compound master stocks (all at 10 mM concentration in 100% DMSO) are diluted 10-fold in water (Distilled water, GIBCO, DNAse and RNAse free) to obtain a 1 mM intermediate work stock in 10% DMSO. This intermediate work stock is further diluted either 3-fold (or 10-fold) in 10% DMSO to obtain an intermediate work stock of 333 μM (or 100 μM) concentration, respectively, in 10% DMSO. The 1 mM as well as 333 μM (or 100 μM) intermediate work stocks are then further diluted 10-fold in 1.1% DMSO to obtain the 10× workstocks at 100 μM and 33.3 μM (or 10 μM) concentration in 2% DMSO. This 10× work stock is then diluted 10-fold in M199 medium supplemented with 1% FBS to obtain the final '1× compound preparation' containing the compounds at 10 μM and 3.33 μM (or 1 μM) as well as 0.2% DMSO. These are the final conditions at which the compounds are tested on the cells. In parallel, the 10× work stock is diluted 10-fold in 'complex trigger' (i.e. the supernatant of TNF-α treated THP1 cells produced as described in Example 1) that is diluted 2-fold in M199 supplemented with 1% FBS to produce the '1× compound in 50% complex trigger preparation'.

At day 1, RASFs are seeded in 96 well plates (Flat bottom, tissue culture treated, Greiner) at a density of 3000 cells/ well in complete synovial growth medium (Cell Applications). Day 5, the compounds are added to the cultured cells as follows. Medium is completely removed from the cells and replaced by 75 μL of the '1× compound preparations' containing the compounds at either 10 μLM or 3.33 μM (or 1 μM) in M199 medium supplemented with 1% FBS and 0.2% DMSO. After an incubation period of 2 hours, which allows the compounds to equilibrate and enter the cells, 25 μL of the '1× compound in 50% complex trigger preparations' are added to the wells on top of the '1× compound preparation', in the wells containing the corresponding compounds at corresponding concentration. In this way, an 8-fold diluted complex trigger is ultimately applied to the cells. An incubation of 48 hrs is then performed and 20 μl of the cell supernatant is then processed in the MMP1 ELISA as described above, delivering raw data (RLU: relative luminescence units). Following controls are included in the experiments. A maximal signal control, in which the cells are activated by the complex trigger but only the 0.2% DMSO vehicle (and thus, no compound) is added. This control indicates the maximal level of MMP1 that can be achieved in the test. A minimal signal control is also included in these experiments. Here, cells are not triggered. The medium of the cells is then changed to 100 μl M199 medium supplemented with 1% FBS at day 5. This control returns the basal MMP1 levels produced by the RASFs. The percent inhibition of the MMP1 expression achieved by the compounds is then calculated based on the RLU data returned by the ELISA with following formula:

[[(maximal MMP1 levels−minimal MMP1 levels)−
(MMP1 level compound X at concentration
Y−minimal MMP1 levels)]/(maximal MMP1
levels−minimal MMP1 levels)]×100.

Toxicity of the compounds is assessed as follows. Day 1, SFs are seeded in white, tissue culture treated 96 well plates at a density of 3000 cells per well in 100 µL complete synovial growth medium. The compound handling, compound addition to the cells as well as activation of the cells is further performed as described above in this example for the determination of the MMP1 levels. After the 48 hrs incubation period, the medium is removed from the wells, replaced by 50 µL fresh M199 medium supplemented with 1% FBS. 50 µL of substrate (Promega Celltiter Glow cell viability kit) is then added to the wells. After an incubation period of 10 min, luminescence signal is measured. A reduction of the luminescence signal by more than 50% as compared to the maximal control wells is considered to reflect significant toxicity. No toxicity is observed for the compounds tested in the 'MMP assay'.

It should be understood that factors such as the differential cell penetration capacity of the various compounds can contribute to discrepancies between the activity of the compounds in the in vitro biochemical and cellular MMP assays.

Example 3

Assay to Assess Effect of Compounds on Cytokine Release by Human PBMCs

Human peripheral blood mononuclear cells (PBMCs) are isolated from "buffy coats" prepared from the blood of healthy volunteers, isolated essentially according to method of Byum (1984). In brief, buffy coat is diluted 1:1 with 1× PBS (Gibco) and 30 mL is carefully put on top of 20 mL Lymphoprep™ (Lucron Bioproducts) in 50 mL Falcon tubes. After centrifugation (35 min, 400 g, 18° C.) the mononuclear cells are collected from the white interphase and washed 3 times with 1× PBS by resuspending and centrifugation (10 min, 200 g). Isolated PBMCs are finally resuspended in RPMI 1640 (Cat.No. 21875, Gibco) that is supplemented with 10% heat-inactivated FBS (Hyclone).

For the assay PBMCs are seeded at 2.5E6 cells/mL in 160 µL in 96-well plates (Nunc). Serial dilution of the test compounds are made first in DMSO (Sigma) and then diluted 50-fold in M199 medium (Gibco) containing 1% heat-inactivated FBS. Compounds are further 1/10 diluted in the assay plates to obtain final DMSO concentration of 0.2%. Cells are preincubated with the compounds for 1 hr at 37° C., 5% $CO_2$. Then, cells are stimulated with LPS (*Escherichia coli* serotype 026:B6, Cat.No. L2654, Sigma) that is added in a volume of 20 µL to a final concentration of 1 µg/ml and cells are further cultured for 24 hr. The plates are centrifuged and the supernatant is collected and stored at −80° C. until analysis of appropriate dilutions in ELISAs.

The following 384-well chemiluminescent ELISA protocol was developed to measure TNFα levels in the supernatant: White Lumitrac 600 384-well plates (Greiner) are coated with (40 µL/well) anti-TNFα capture antibody (Cat.No. 551220, BD Pharmingen) that is diluted to 1 µg/mL in 1× PBS (Gibco). After overnight incubation at 4° C., plates are washed with 1× PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well buffer B (1× PBS containing 1% BSA (Sigma), 5% sucrose (Sigma) and 0.05% $NaN_3$ (Sigma)). After 4 hr incubation at RT, blocking buffer is removed and plates are washed once with PBST (1× PBS with 0.05% Tween-20 (Sigma)). Then, 40 µL of sample is transferred to the ELISA plates and plates are incubated at 4° C. Next day, plates are washed 3 times (twice with PBST and once with PBS) and 35 µL/well biotinylated anti-TNFα antibody (Cat.No. 554511, BD Pharmingen) diluted first to a concentration of 250 ng/ml in buffer D (1× PBS with 1% BSA) is added. After 2 h of incubation at RT, plates are washed as described above and 35 µL/well of a 1/2000 dilution of streptavidin-HRP conjugate (Cat.No. SNN2004, Biosource) in buffer D is added. After 45 min, plates are washed as described above and incubated for 5 min with 50 µL/well BM Chemiluminescence ELISA Substrate POD (Roche). Readout is performed on the Luminoscan Ascent Luminometer (Labsystems) with an integration time of 100 msec delivering raw data (RLU: relative luminescence units). The following controls are included in the experiments, a maximal signal control, in which the cells are activated by LPS but only the 0.2% DMSO vehicle (and thus no compound) is added. This control indicates the maximal level of TNFα that can be achieved in the test. A minimal signal control is also included in these experiments. Here, cells are not triggered. This control returns the basal TNFα levels produced by the PBMCs. The percent inhibition (PIN) of the TNFα release, achieved by the compounds is then calculated based on the RLU data returned by the ELISA with following formula: 100−[((TNFα level compound X at concentration Y−minimal TNFα levels)/(maximal TNFα levels−minimal TNFα levels))×100]. Where compounds are tested at 8 concentrations (⅓ serial dilution), $EC_{50}$-values can be calculated by curve fitting of the means of the PIN data achieved for a compound at each test concentration.

To assay the effect of compounds on the release of IL1 and IL6 by LPS stimulated PBMC cultures, appropriate dilutions of the supernatant can be measured using the same ELISA protocol as described above. Matched pair antibodies for IL1 and IL6 ELISA (all from R&D Systems) may be used as follows: anti-IL1 capture antibody (Cat.No. MAB601) used at 0.5 µg/mL , biotinylated anti-IL1 detection antibody (Cat.No. BAF201) used at 50 ng/mL; anti-IL6 capture antibody (Cat.No. MAB206) used at 1 µg/mL; biotinylated anti-IL6 detection antibody (Cat.No. BAF206) used at 50 ng/mL.

Example 4

MMP13 Assay

The protocol of the MMP13 ELISA is described in section 4.1, then testing of compounds on release of IL-1/OSM-driven MMP13 expression in SW1353 chondrosarcoma cell line is described in section 4.2.

4.1 MMP13 ELISA protocol

A 384 well format ELISA for measurement of MMP13 was developed. Various primary antibodies were tested, as well as various ELISA protocols. The following protocol is developed and validated to measure MMP13 levels in supernatant of cell cultures in 384 well plates.

Black maxisorb 384 well plates (Nunc 460518) are coated with 35 µl of a buffered solution containing 1.5 µg/mL anti-MMP13 antibody MAB511 (R&D systems). The antibody is diluted in carbonate-bicarbonate coating buffer (1.59 g $Na_2CO_3$ (Sigma S-7795) and 2.93 g NaHCO3 (Sigma S-5761) in 1 L MilliQ water, adjusted to pH 9.6). After overnight incubation at 4° C., wells are washed twice with 100 µL PBST (80 g NaCl, 2 g KCl (Sigma), 11.5 g $Na_2HPO_4.7H_2O$ and 2 g $KH_2PO_4$ in 10 L milliQ water; pH 7.4+0.05% Tween-20 (Sigma)) and blocked with 100 µL/well blocking buffer (5% non fat dry milk in PBS). After overnight incubation at 4° C., wells are washed twice with 100 µL PBST. The PBST is removed and 35 µL of sample is transferred to the ELISA plates. After 4 hr incubation at RT, plates are washed twice with PBST and incubated for 1 hr at 37° C. with 35 µL/well 1.5 mM APMA solution (a 10 mM APMA stock solution is prepared one day before (35.18 mg APMA (Sigma A-9563) in 10 mL 0.1M NaOH (Merck 1.06469.1000) and stored at 4° C. Before use, the 10 mM APMA stock solution is diluted to 1.5 mM in 1×APMA buffer (10× APMA buffer: 500 mM Tris (Roche 708976), 50 mM CaCl$_2$ (Sigma C-5080), 500 µL ZnCl$_2$ (Sigma Z-0173), 1.5 M NaCl (Calbiochem 567441), 0.5% Brij35 (Sigma 430 AG-6) and adjust to pH 7.0). After activation of MMP13 by APMA, plates are washed again two times with 100 µL PBST/well and 35 µL of substrate solution is added to each well. Substrate solution is prepared as follows: OmniMMP Fluorescent substrate (Biomol P-126) stock solution (2 mM in DMSO, stored at −20° C.) is diluted in 1× OmniMMP buffer (10× OmniMMP buffer: 500 mM Hepes (Sigma H4034), 100 mM CaCl$_2$ (Sigma C5080), 0.5% Brij35 (Sigma 430 AG-6; adjusted to pH 7.0) to a final concentration of 0.01 mM. After an overnight incubation at 37° C., the active MMP13 in the sample has cleaved the substrate and released fluorescence. Readout is performed on the EnVision (Perkin Elmer) using 320 nm excitation/405 nm emission filters.

4.2 Assessing effect of compounds on cytokine driven MMP13 expression in SW1353 cells Human chondrosarcoma cell line SW1353 was acquired from ATCC and grown in DMEM supplemented with 10% heat-inactivated FBS and 1× penicillin/streptomycin (Invitrogen) in a humidified 5% CO$_2$ incubator at 37° C. Aliquots of the cells were frozen and cryopreserved in liquid nitrogen. Starting from a cryopreserved aliquot, cells are further grown by sub-culturing at a 1/5-1/8 ratio twice a week by trypsinisation.

Starting from the compound master stocks (all at 10 mM concentration in 100% DMSO) a 3-fold serial dilution is made in 96-well plates in 100% DMSO. Then, plates are futher diluted 50-fold in M199 medium supplemented with 1% heat-inactivated FBS to obtain an intermediate work stock.

At day 1, SW1353 cells are seeded in 96-well plates (flat bottom, tissue culture treated, Greiner) at a density of 15000 cells/well in 120 µL growth medium. The next day, 15 µL compound out of the intermediate work stock is added. After an incubation period of 60 minutes, which allows the compounds to equilibrate and enter the cells, cells are stimulated with a mixture of IL-1β and OSM, added in a volume of 15 µL to obtain final concentrations of 1 ng/ml IL-1β and 25 ng/ml OSM. For that, stocks of IL-1 (10 µg/ml) and OSM (25 µg/ml) (both PeproTech) were diluted to 10 ng/ml and 250 ng/ml respectively, in M199 medium supplemented with 1% FBS. After incubation for 48 hr, the cell supernatant was harvested and an appropriate dilution was processed in the MMP13 ELISA as described above, delivering raw data (RFU: relative fluorescence units). The following controls are included in the experiments: a maximal signal control, in which the cells are activated by the IL1-β/OSM cytokine mixture but only the 0.2% DMSO vehicle (and thus no compound) is added. This controls indicated the maximal MMP13 levels that can be achieved in the test. A minimal signal control, in which cells only receive the 0.2% DMSO vehicle and no trigger, is also included. This control returns the basal MMP13 levels produced by the SW1353 cells. The percent inhibition of the MMP13 expression achieved by the compounds is then calculated based on the RFU data returned by the ELISA with the following formula: [[(maximal MMP13 levels−minimal MMP13 levels)−(MMP13 level compound X at concentration Y−minimal MMP13 levels)]/(maximal MMP13 levels−minimal MMP13 levels)]×100. Based on a plot of percent inhibition vs Log (molar concentration) and curve fitting, IC$_{50}$ values of a particular compound can be calculated.

The following compounds have been or can be prepared according to the synthetic methods described above. For the purpose of Table 1 below, activity of each compound, which can be determined using the MAPKAPK5 assay method described in Example 1, is expressed as follows:

TABLE 1

| Ex # | Structure | Name | MW | M + H+, m/z | MAPKAPK5 IC$_{50}$ nM |
|---|---|---|---|---|---|
| 1 | 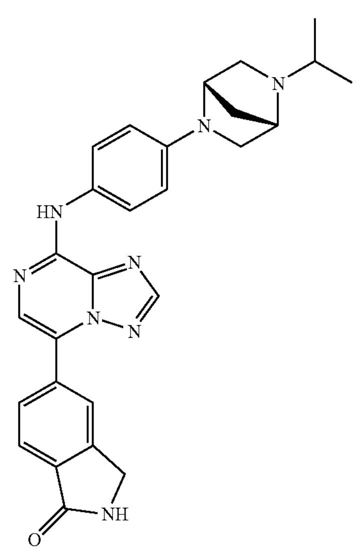 | 5-(8-(4-((1S,4S)-5-isopropyl-2,5-diazabicyclo[2.2.1]heptan-2-yl)phenylamino)-[1,2,4]triazolo[1,5-a]pyrazin-5-yl)isoindolin-1-one | 481 | 482 | ++++ |

TABLE 1-continued

| Ex # | Structure | Name | MW | M + H+, m/z | MAPKAPK5 IC$_{50}$ nM |
|---|---|---|---|---|---|
| 2 | 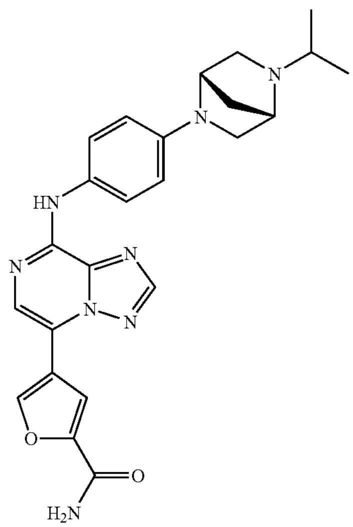 | 4-(8-(4-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide | 458 | 459 | ++++ |
| 3 | 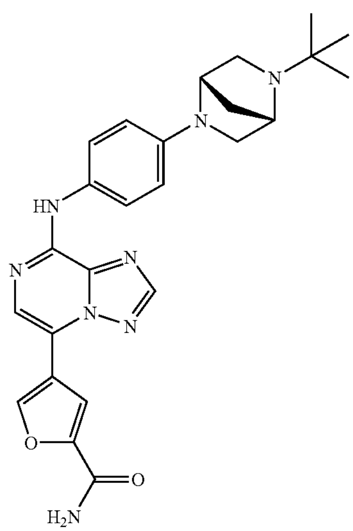 | 4-(8-(4-((1S,4S)-5-tert-butyl-2,5-diazabicyclo[2.2.1]heptan-2-yl)phenylamino)-[1,2,4]triazolo[1,5-a]pyrazin-5-yl)furan-2-carboxamide | 472 | 473 | ++++ |
| 4 | 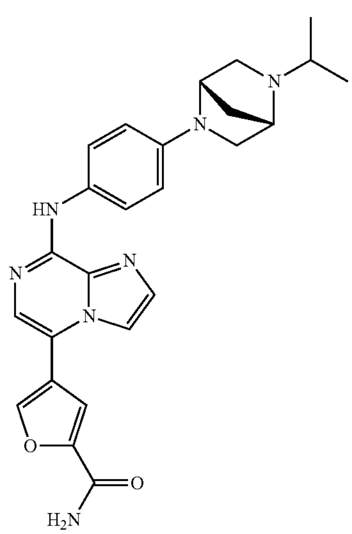 | 4-(8-(4-((1S,4S)-5-isopropyl-2,5-diazabicyclo[2.2.1]heptan-2-yl)phenylamino)imidazo[1,2-a]pyrazin-5-yl)furan-2-carboxamide | 457 | 458 | +++ |

TABLE 1-continued

| Ex # | Structure | Name | MW | M + H+, m/z | MAPKAPK5 IC$_{50}$ nM |
|---|---|---|---|---|---|
| 5 | 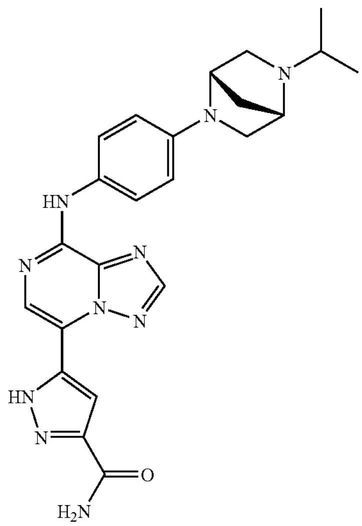 | 5-{8-(4-((1S,4S)-5-isopropyl-2,5-diazabicyclo[2.2.1]heptan-2-yl)phenyl-amino)-[1,2,4]triazolo[1,5-a]pyrazin-5-yl}-1H-pyrazole-3-carboxamide | 459 | 459 | +++ |
| 6 | 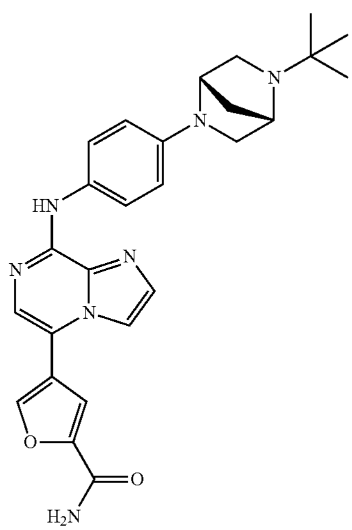 | 4-{8-(4-((1S,4S)-5-tert-butyl-2,5-diazabicyclo[2.2.1]heptan-2-yl)-phenyl-amino)imidazo[1,2-a]pyrazin-5-yl}-furan-2-carboxamide | 472 | 472 | +++ |
| 7 | 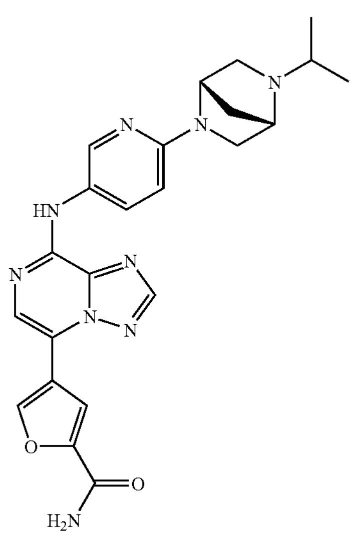 | 4-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-furan-2-carboxamide | 460 | 460 | ++++ |

TABLE 1-continued

| Ex # | Structure | Name | MW | M + H+, m/z | MAPKAPK5 IC$_{50}$ nM |
|------|-----------|------|-----|------|------|
| 8 | 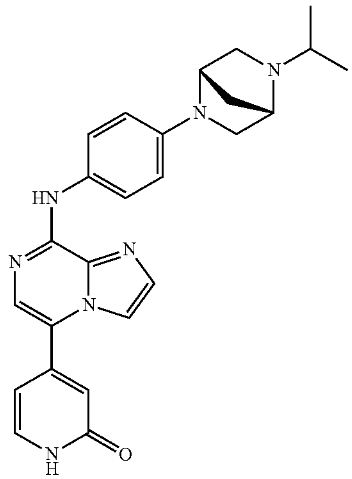 | 4-{8-(4-((1S,4S)-5-isopropyl-2,5-diazabicyclo[2.2.1]heptan-2-yl)phenyl-amino)imidazo[1,2-a]pyrazin-5-yl}-1H-pyridin-2-one | 442 | 442 | +++ |
| 9 | 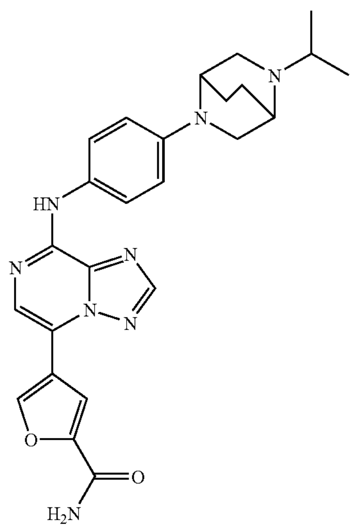 | 4-{8-(4-(5-isopropyl-2,5-diazabicyclo[2.2.2]octan-2-yl)phenylamino)[1,2,4]triazolo[1,5-a]pyrazin-5-yl}-furan-2-carboxamide | 473 | 473 | ++++ |
| 10 | 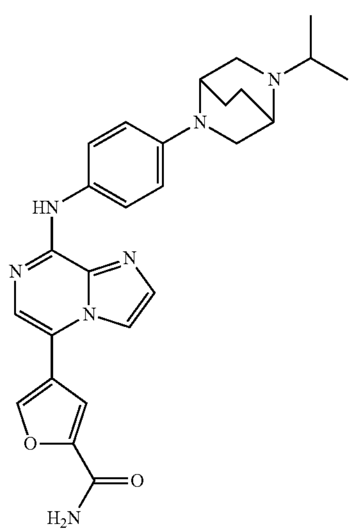 | 4-{8-(4-(5-isopropyl-2,5-diazabicyclo[2.2.2]octan-2-yl)phenylamino)-imidazo[1,2-a]pyrazin-5-yl}-furan-2-carboxamide | 472 | 472 | +++ |

TABLE 1-continued

| Ex # | Structure | Name | MW | M + H+, m/z | MAPKAPK5 IC$_{50}$ nM |
|---|---|---|---|---|---|
| 11 | 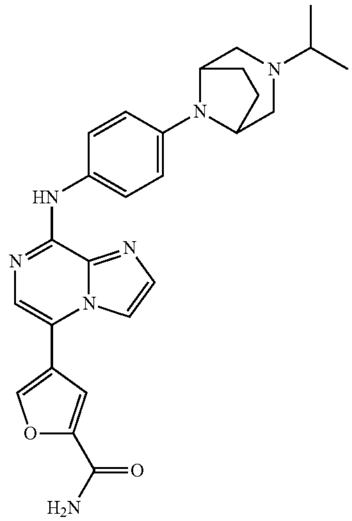 | 4-{8-(4-(3-isopropyl-3,8-diazabicyclo[3.2.1]octan-8-yl)phenylamino)-imidazo[1,2-a]pyrazin-5-yl}-furan-2-carboxamide | 472 | 472 | +++ |
| 12 | 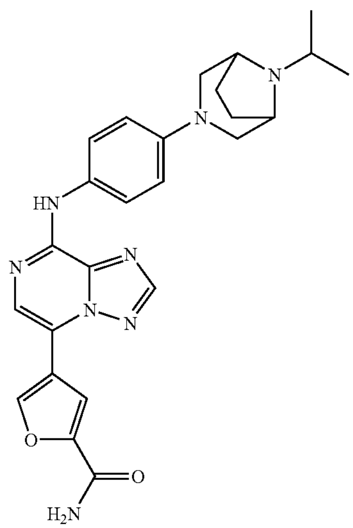 | 4-{8-(4-(8-isopropyl-3,8-diazabicyclo[3.2.1]octan-3-yl)phenylamino)[1,2,4]-triazolo[1,5-a]pyrazin-5-yl}-furan-2-carboxamide | 473 | 473 | ++++ |
| 13 | 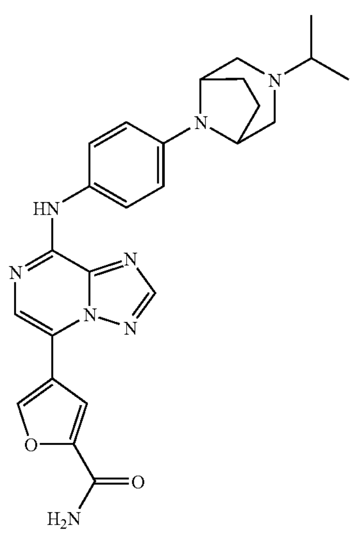 | 4-{8-(4-(3-isopropyl-3,8-diazabicyclo[3.2.1]octan-8-yl)phenylamino)[1,2,4]-triazolo[1,5-a]pyrazin-5-yl}-furan-2-carboxamide | 473 | 473 | ++++ |

TABLE 1-continued

| Ex # | Structure | Name | MW | M + H+, m/z | MAPKAPK5 IC$_{50}$ nM |
|---|---|---|---|---|---|
| 14 | 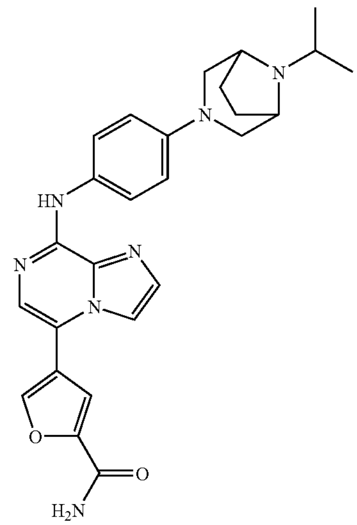 | 4-{8-(4-(8-isopropyl-3,8-diazabicyclo[3.2.1]octan-3-yl)phenylamino)-imidazo[1,2-a]pyrazin-5-yl}-furan-2-carboxamide | 472 | 472 | +++ |
| 15 | 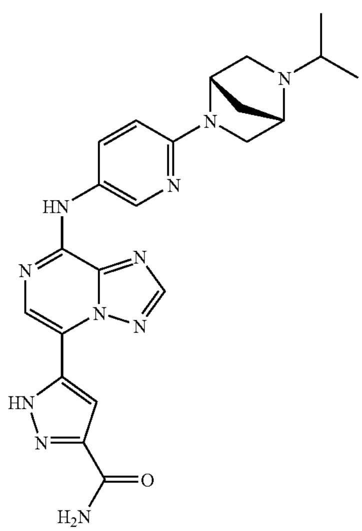 | 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-1H-pyrazole-3-carboxamide | 460 | 460 | +++ |
| 16 | 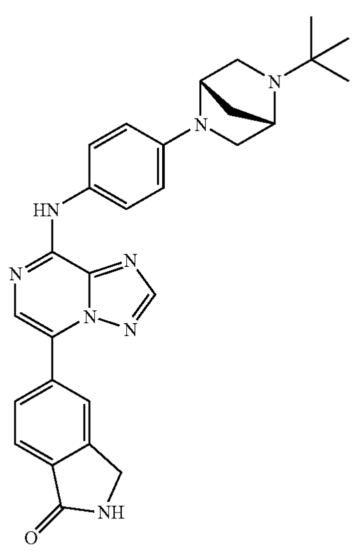 | 5-{8-(4-((1S,4S)-5-tert-butyl-2,5-diazabicyclo[2.2.1]heptan-2-yl)phenylamino)-[1,2,4]triazolo-[1,5-a]pyrazin-5-yl}-2,3-dihydro-isoindol-1-one | 495 | 495 | +++ |

TABLE 1-continued

| Ex # | Structure | Name | MW | M + H+, m/z | MAPKAPK5 IC$_{50}$ nM |
|---|---|---|---|---|---|
| 17 | 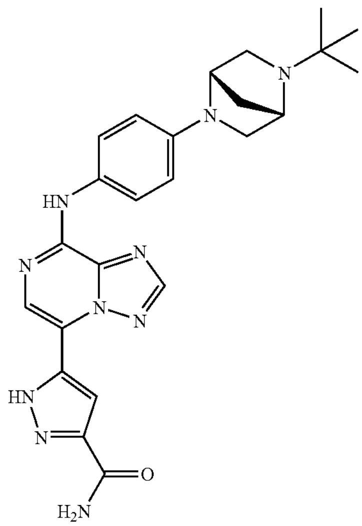 | 5-{8-(4-((1S,4S)-5-tert-butyl-2,5-diazabicyclo[2.2.1]heptan-2-yl)phenyl-amino)-[1,2,4]triazolo[1,5-a]pyrazin-5-yl}-1H-pyrazol-3-carboxamide | 473 | 473 | +++ |
| 18 | 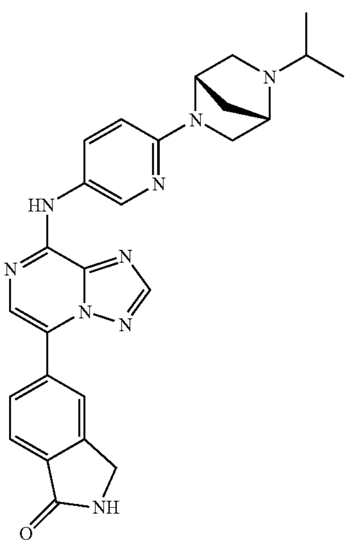 | 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-2,3-dihydro-isoindol-1-one | 482 | 482 | +++ |
| 19 | 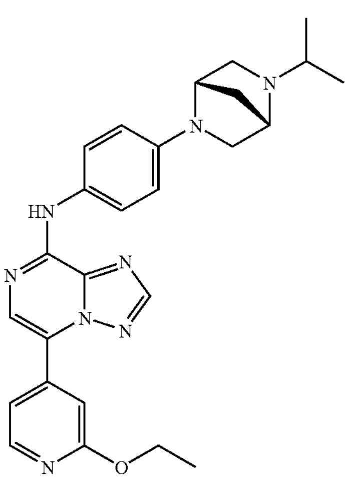 | 5-(2-ethoxypyridin-4-yl)-N-(4-((1S,4S)-5-isopropyl-2,5-diazabicyclo[2.2.1]heptan-2-yl)phenyl)-[1,2,4]triazolo[1,5-a]pyrazin-8-amine | 471 | 471 | + |

TABLE 1-continued

| Ex # | Structure | Name | MW | M + H+, m/z | MAPKAPK5 IC$_{50}$ nM |
|---|---|---|---|---|---|
| 20 | 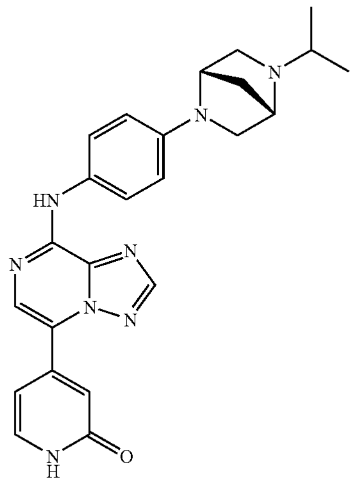 | 4-(8-(4-((1S,4S)-5-isopropyl-2,5-diazabicyclo[2.21]heptan-2-yl)phenylamino)-[1,2,4]triazolo[1,5-a]pyrazin-5-yl)pyridin-2(1H)-one | 443 | 443 | + |
| 21 | 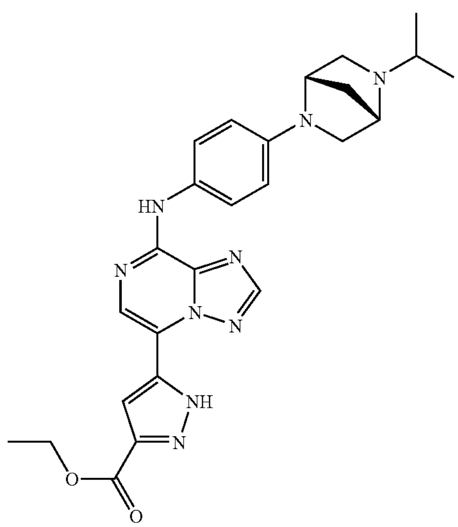 | Ethyl 5-(8-(4-((1S,4S)-5-isopropyl-2,5-diazabicyclo[2.2.1]heptan-2-yl)phenylamino)-[1,2,4]triazolo[1,5-a]pyrazin-5-yl)-1H-pyrazolo-3-carboxylate | 488 | 488 | + |
| 22 | 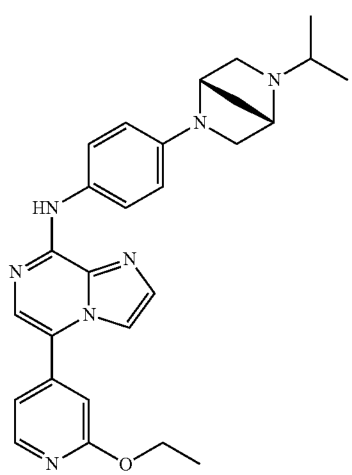 | 5-(2-ethoxypyridin-4-yl)-N-(4-((1S,4S)-5-isopropyl-2,5-diazabicyclo[2.2.1]heptan-2-yl)phenyl)imidazo[1,2-a]pyrazin-8-amine | 470 | 470 | + |

TABLE 1-continued

| Ex # | Structure | Name | MW | M + H+, m/z | MAPKAPK5 IC$_{50}$ nM |
|---|---|---|---|---|---|
| 23 | 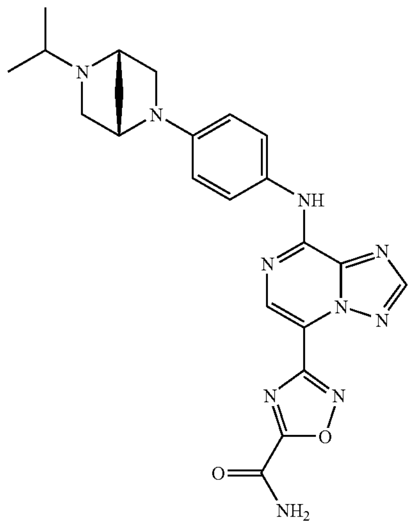 | 3-(8-(4-((1S,4S)-5-isopropyl-2,5-diazabicyclo[2.2.1]heptan-2-yl)phenylamino)-[1,2,4]triazolo[1,5-a]pyrazin-5-yl)-1,2,4-oxadiazole-5-carboxamide | 461 | 461 | + |
| 24 | 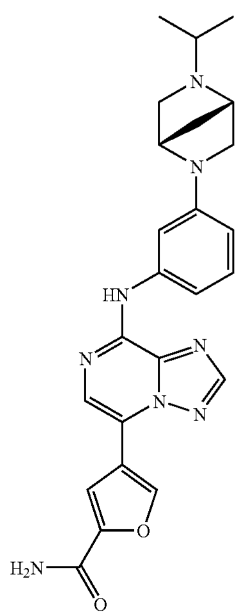 | 4-(8-(3-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide | 458 | 459 | ++++ |

TABLE 1-continued

| Ex # | Structure | Name | MW | M + H+, m/z | MAPKAPK5 IC$_{50}$ nM |
|---|---|---|---|---|---|
| 25 | 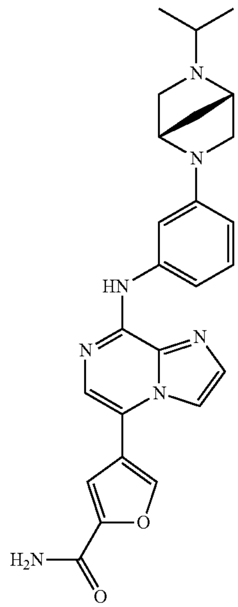 | 4-(8-(3-((1S,4S)-5-isopropyl-2,5-diazabicyclo[2.2.1]heptan-2-yl)phenylamino)imidazo[1,2-a]pyrazin-5-yl)furan-2-carboxamide | 457 | 458 | +++ |
| 26 | 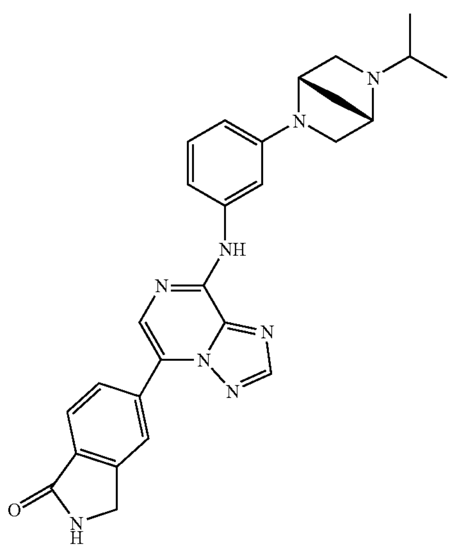 | 5-(8-(3-((1S,4S)-5-isopropyl-2,5-diazabicyclo[2.2.1]heptan-2-yl)phenylamino)-[1,2,4]triazolo[1,5-a]pyrazin-5-yl)isoindolin-1-one | 480 | 481 | +++ |

TABLE 1-continued

| Ex # | Structure | Name | MW | M + H+, m/z | MAPKAPK5 IC$_{50}$ nM |
|---|---|---|---|---|---|
| 27 | 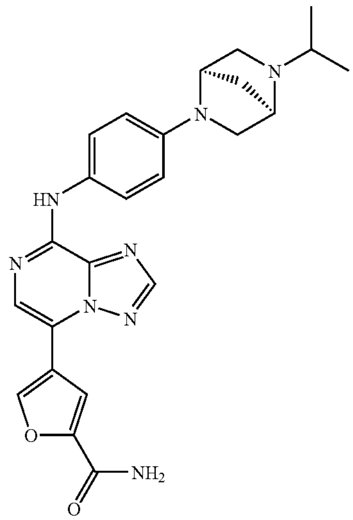 | 4-{8-[4-((1R,4R)-5-Isopropyl-2,5-diaza-bicyclo[2.2.1]hept-2-yl)-phenylamino]-[1,2,4]triazolo[1,5-a]pyrazin-5-yl}-furan-2-carboxylic acid amide | 458 | 459 | ++++ |

++++ compound exhibited MAPKAPK5 IC$_{50}$ 0.01-100 nM
+++ compound exhibited MAPKAPK5 IC$_{50}$ 101-500 nM
++ compound exhibited MAPKAPK5 IC$_{50}$ 501-1000 nM
+ compound exhibited MAPKAPK5 IC$_{50}$ > 1000 nM MMP1 data

| Ex # | MMP1 IC$_{50}$ nM |
|---|---|
| 1 | § |
| 2 | §§ |
| 3 | § |
| 4 | § |
| 5 | §§ |
| 6 | § |
| 7 | N/A |
| 8 | §§ |
| 9 | §§ |
| 10 | § |
| 11 | § |
| 12 | § |
| 13 | N/A |
| 14 | § |
| 15 | § |
| 16 | § |
| 17 | § |
| 18 | § |
| 19 | § |
| 20 | § |
| 21 | § |
| 22 | § |
| 23 | § |
| 24 | § |
| 25 | § |
| 26 | § |

§§ compound exhibited MMP1 IC$_{50}$ 1-1000 nM
§ compound exhibited MMP1 IC$_{50}$ >1000 nM MMP13 data

TABLE 3

| Ex # | MMP13 IC$_{50}$ nM |
|---|---|
| 1 | * |
| 2 | *** |
| 3 | *** |
| 4 | * |
| 5 | * |
| 6 | * |
| 7 | *** |
| 8 | *** |
| 9 | * |
| 10 | N/A |
| 11 | * |
| 12 | * |
| 13 | * |
| 14 | N/A |
| 15 | * |
| 16 | * |
| 17 | ** |
| 18 | * |
| 19 | * |
| 20 | * |
| 21 | * |
| 22 | * |
| 23 | * |
| 24 | * |
| 25 | * |
| 26 | * |

*** compound exhibited MMP13 IC$_{50}$ 1-500 nM
** compound exhibited MMP13 IC$_{50}$ 501-1000 nM
* compound exhibited MMP13 IC$_{50}$ >1000 nM In Vivo Studies Example 5

Tolerability of Compounds

This protocol is designed to assess the tolerability of the compounds of the invention in healthy DBA/1J mice to determine the "therapeutic window" as defined by the dosing range between efficacious (mouse therapeutic Collagen-Induced Arthritis model) and toxic doses.

5.1 Animals

DBA/1J nude mice are used (CERJ (France)), the mice were 10-11 weeks old, and had a body weight of approx 20 g.

5.2 Compounds Preparation

Compounds are prepared for a dosing regimen of 100 mg/kg/d, po, free base, in a standard volume of injection of 0.1 mL/10 g of mice (equivalent to 10 mg/1 mL). For solution preparations, compounds were dissolved in 0.5% methylcellulose and 1% DMSO, once a week.

5.3 Experimental groups

Groups are randomized based on body weight and treated for up to two weeks. Each group contained 5 mice and received either test compound at 100 mg/kg, a comparison compound at 100 mg/kg/d (Compound A) or vehicle on a daily basis in a dosing volume of 200 µL per mouse.

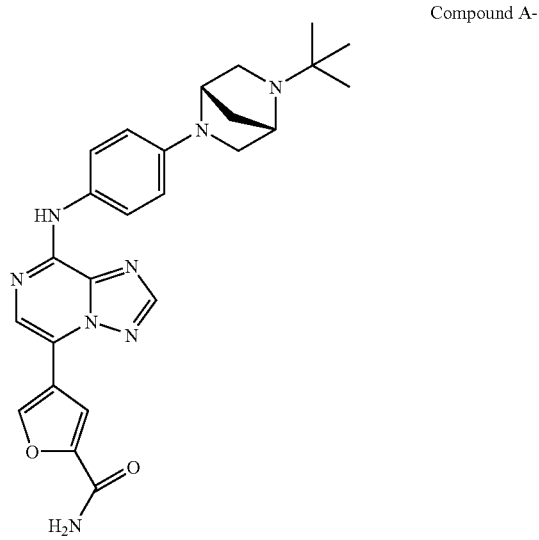

Compound A-

5.4 Animal Monitoring (Clinical signs and Body Weight)

Potential drug toxicity is monitored by observation every day and by recording body weights three times a week for weight loss. All statistical analyses were performed using Student's t test.

Figure 6A:
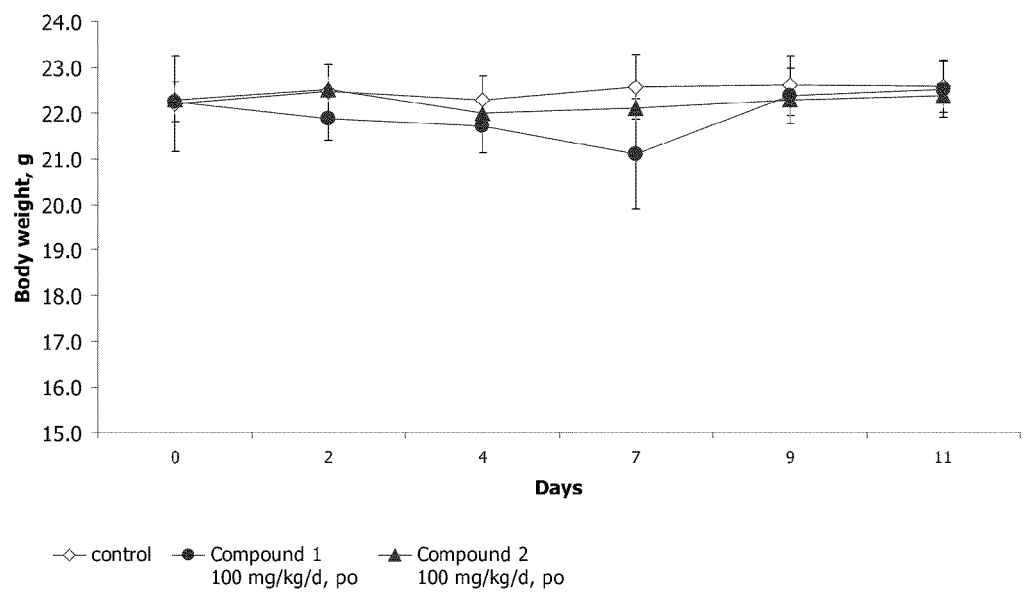
FIG. 6A This graph shows the results of tolerability study conducted with a compound of the invention, where the measured effect was against total body weight.
Figure 6B:
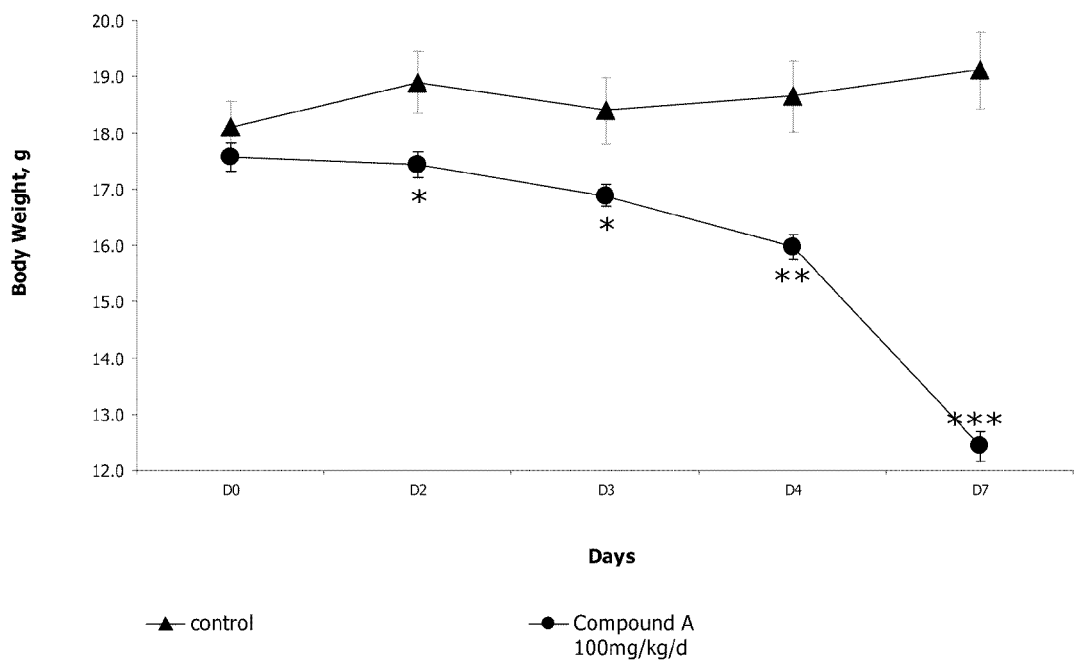
FIG. 6B This graph shows the results of tolability study against a comparative compound.
Figure 7:
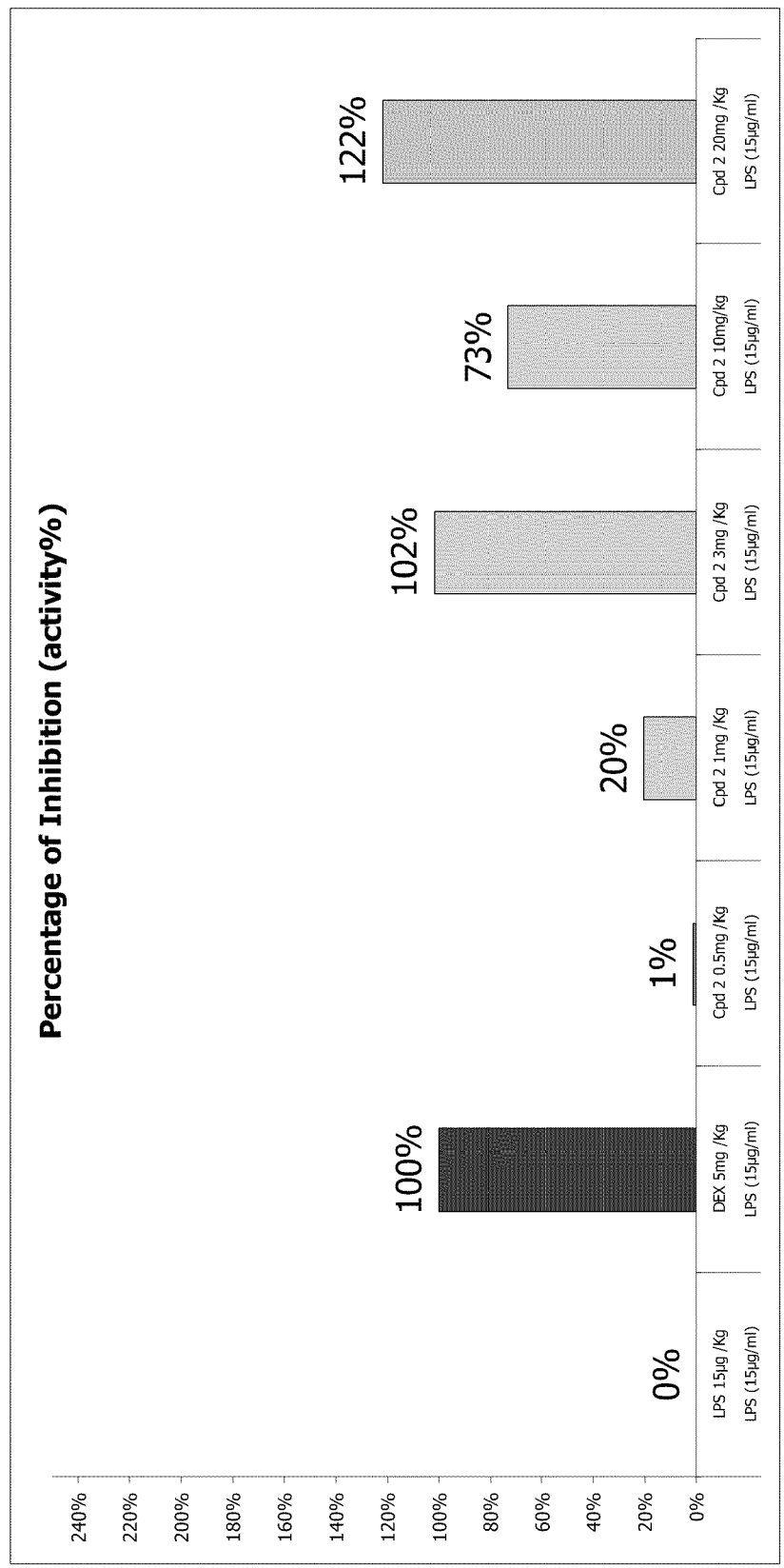
FIG. 7 This graph shows the percentage inhibition of TNF alpha release obtained with a compound of the invention, after injection of LPS (bacterial lipopolysaccharides) which is known to cause cholestasis in sepsis. The benchmark here is the well known dexamethasone (100% inhibition) (DEX).

To assess the general tolerability of the treatments, the total body weight is followed throughout the course of the study. FIG. 6A shows the effect of Compound 1 and Compound 2 on the total body weight, FIG. 6B shows the effect of a comparator compound A (see below for structure). The data indicates that the bridged compounds are tolerated better than the non-bridged compounds. In particular there was no statistically significant difference between the weight of the animals treated with compounds 1 or 2 at 100 mg/kg/d compared to the vehicle.

Example 6

CIA Model

Complete Freund Adjuvant/Collagen II (CFA/Coll II, bovine) is injected (1 mg/mL, 100 µL per animal) into the tail (intradermic) at the start of the experiment. Incomplete Freund Adjuvant/Collagen II (IFA/Coll II) is injected into the tail at the same level (1 mg/mL, 100 µL per animal) 21 days after CFA/Coll II injection.

Animals are then randomized based on score and assigned to treatment groups assuring an equal distribution of score in the different groups.

Treatment with either the test compound (1 mg/kg/d, 3 mg/kg/d or 30 mg/kg/d), positive control (Enbrel, 10 mg/kg/ 3×week, ip) or vehicle (Methyl Cellulose, 1% DMSO) starts at day 8 post IFA/Coll II-boost (i.e. day 28 of the experiment).

Animals are dosed daily with the test compound, positive control or vehicle for 14 days. The animals are scored daily for clinical symptoms, scoring is reported for the individual paws. During the treatment period the body weight of the animals is monitored. Bone protection is analysed by x-ray imaging.

Selected compounds of the invention were efficacious at 3 or 30 mg/kd/d.

Example 7

Septic Shock Model

Injection of lipopolysaccharide (LPS) induces a rapid release of soluble tumour necrosis factor (TNF-α) into the periphery. This model is used to analyse prospective blockers of TNF release in vivo.

Six BALB/cJ female mice (20 g) per group are treated at the intended dosing once, po. Thirty minutes later, LPS (15 µg/kg; E. coli serotype 0111:B4) is injected ip. Ninety minutes later, mice are euthanized and blood is collected. Circulating TNF alpha levels are determined using commercially available ELISA kits. Dexamethasone (5 µg/kg) is used as a reference anti-inflammatory compound. Selected compounds of the invention were efficacious at 3, 10 and 20 mg/kg, po.

Example 8

Mouse Collagen Antibody Induced Arthritis (CAIA) Model (Also Called Mouse Monoclonal AntiBody (MAB) Model)

Eight BALB/cJ female mice (20 g) per group are treated at the intended dosing once, po. The same day, 2 mg/mouse of a cocktail of four monoclonal antibodies (MDBiosciences; ref CIA-MAB-50) is injected i.v. LPS (50 µg/mouse; E. Coli serotype 55:B5) is administered i.p., three days later. Treatment with either the test compound, positive control (Enbrel, 10 mg/kg/3×week, i.p. or dexamethasone, 1 mg/kg, daily, p.o.) or vehicle (Methyl Cellulose, 1% DMSO) starts the day of the antibodies injection. Animals are dosed daily with the test compound, positive control or vehicle for up to 10 days. The animals are scored for clinical symptoms and scoring is reported for the individual paws. During the treatment period, the body weight of the animals is monitored.

REFERENCES REFERENCES

Choy E H, Panayi G S. (2001). N Engl J Med. 344: 907-16.
Firestein G S. (2003). Nature. 423:356-61.
Smolen J S, Steiner G. (2003). Nat Rev Drug Discov. 2: 473-88.
Lee D M, Weinblatt M E (2001). Lancet. 358: 903-11.
Kremer J. M., Westhovens R., Leon M., Di Giorgio E., Alten R., Steinfeld S., Russell A., Dougados M., Emery P., Nuamah I. F., Williams G. R., Becker J. -C., Hagerty D. T., Moreland L. W. (2003) N Engl J Med. 349:1907-1915.
Edwards J. C. W., Szczepanski L., Szechinski J., Filipowicz-Sosnowska A., Emery P., Close D. R., Stevens R. M., Shaw T. (2004) N Engl J Med. 350:2572-2581.
O'Dell J R, Leff R, Paulsen G, Haire C, Mallek J, Eckhoff P J, Fernandez A, Blakely K, Wees S, Stoner J, Hadley S, Felt J, Palmer W, Waytz P, Churchill M, Klassen L, Moore G. (2002) Arthritis Rheum. 46:1164-70.
St Clair E W, van der Heijde D M, Smolen J S, Maini R N, Bathon J M, Emery P, Keystone E, Schiff M, Kalden J R, Wang B, Dewoody K, Weiss R, Baker D; (2004) Combination of infliximab and methotrexate therapy for early rheumatoid arthritis: a randomized, controlled trial. Arthritis Rheum. 50 :3432-43.
Gomez-Reino J J, et al. (2003). Arthritis Rheum. 48: 2122-7.
O'Dell J R. (2004) Therapeutic strategies for rheumatoid arthritis. N Engl J Med. 350(25):2591-602.
New L, Jiang Y, Han J. (2003) Regulation of PRAK subcellular location by p38 MAP kinases. Mol Biol Cell. 14(6): 2603-16.
Shi Y, Kotlyarov A, Laabeta K, Gruber A D, Butt E, Marcus K, Meyer H E, Friedrich A, Volk H D, Gaestel M. (2003) Elimination of protein kinase MK5/PRAK activity by targeted homologous recombination. Mol Cell Biol. 23:7732-41.
Seternes O M, Mikalsen T, Johansen B, Michaelsen E, Armstrong C G, Morrice N A, Turgeon B, Meloche S, Moens U, Keyse S M. (2004) Activation of MK5/PRAK by the atypical MAP kinase ERK3 defines a novel signal transduction pathway. EMBO J. 23:4780-91.
Andreakos E, et al. (2003). Arthritis Rheum. 48: 1901-12.
Cunnane G, et al. (2001). Arthritis Rheum 44: 2263-74.
Coussens L M, et al. (2002). Science 295: 2387-92.
Creemers E E, et al. (2001). Circ Res. 2001 89:201-10
Gapski R, et al. (2004). J Periodontol. 75:441-52.
Reif S, Somech R, Brazovski E, Reich R, Belson A, Konikoff F M, Kessler A. (2005) Digestion. 71:124-130.
Rosenberg G A. (2002). Glia. 39:279-91.
Schanstra J P, et al. (2002). J Clin Invest. 110:371-9.
Suzuki R, et al. (2004). Treat Respir Med. 3:17-27.
US 2005/0009832
WO02/056888
WO99/64582
Bundgard, H., Design of Prodrugs, Elsevier, Amsterdam 1985
K. Widder et al, Methods in Enzymology, Ed. Academic Press, 42, (1985)
Advanced Drug Delivery Reviews, H. Bundgard, 8 ,1-38, (1992)
H. Bundgaard, et al, J. Pharm. Sci., 77,285 (1988);
N. Nakeya et al, Chem. Pharm. Bull., 32, 692 (1984);
Pro-drugs as Novel Delivery Systems, T. Higuchi and V. Stella, 14 A.C.S. Symposium Series, Bioreversible Carriers in Drug Design, E. B. Roche, ed., American Pharmaceutical Association and Pergamon Press, 1987
Remington's Pharmaceutical Sciences, 17th edition, 1985, Mack Publishing Company, Easton, Pa.
T. W. Greene and P. G. M. Wuts, *Protecting Groups in Organic Synthesis*, Second Edition, Wiley, New York, 1991
J. H. Jones et al., J. Med. Chem. 1969, 12, 285-87
H. Newman et al., J. Heterocycl. Chem, 1974, 11, 449-451
D. Barlocco et al., J. Med.Chem., 1998, 41, 674-681
DiMauro et al., J. Med. Chem.,2008, 51, 1681-1694
J. M. Keith et al., Bioorg. Med Chem Lett, 2008; 4838-4843

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A compound according to Formula Ia:

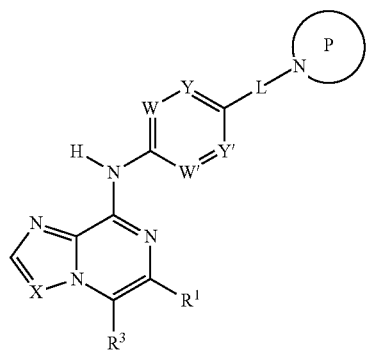

Ia wherein each of W, W', Y, and Y' is independently $CR^{2a}$ or N; provided that no more than two of W, W', Y, and Y' can be N at the same time;

X is N;

L is a single bond;

the ring P is:

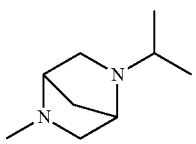 or 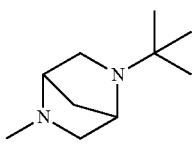

$R^1$ is H;

each $R^{2a}$ is H; and $R^3$ is selected from

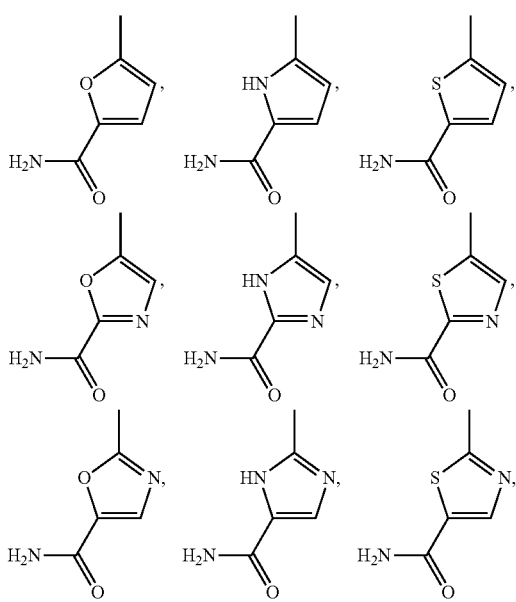

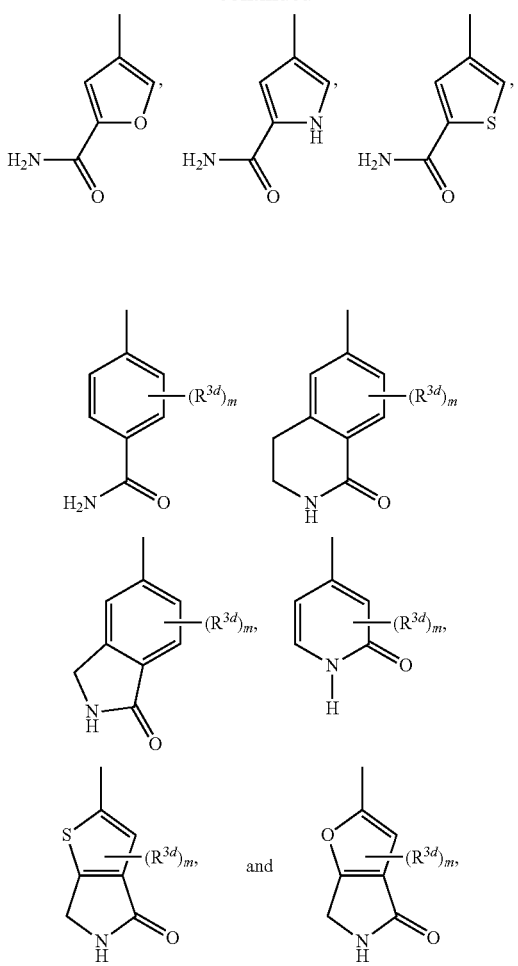

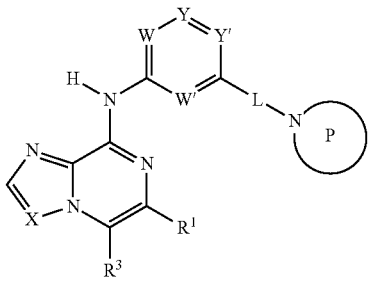

wherein m is selected from 0, 1 or 2 and each $R^{3d}$ is independently Me, Cl or F;

or a pharmaceutically acceptable salt thereof; and stereoisomers thereof.

2. A compound according to Formula Ib:

Ib wherein each of W, W', Y, and Y' is independently $CR^{2a}$ or N; provided that no more than two of W, W', Y, and Y' can be N at the same time;

X is N;

L is a single bond;

the ring P is:
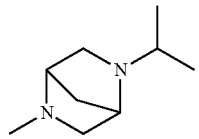 or 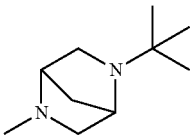
$R^1$ is H;
each $R^{2a}$ H; and
$R^3$ is selected from;
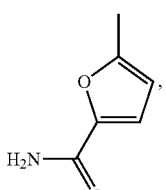 , 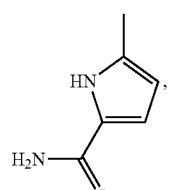 , 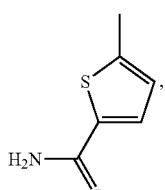 ,
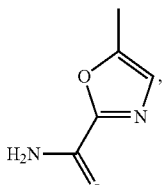 , 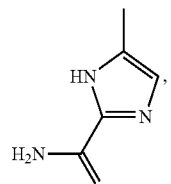 , 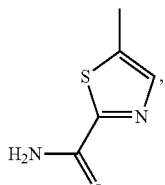 ,
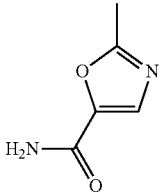 , 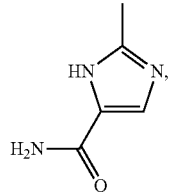 , 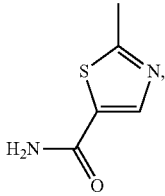 ,
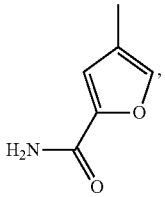 , 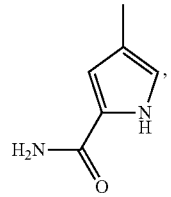 , 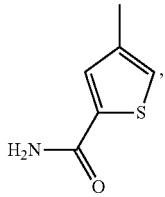 ,
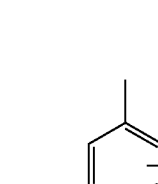 , 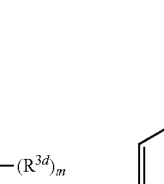 ,
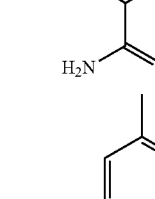 , 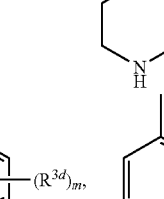 ,
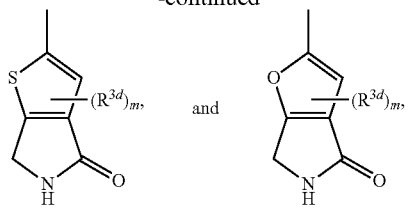 and 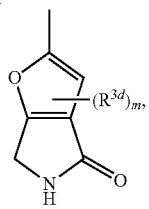
wherein m is selected from 0, 1 or 2 and each $R^{3d}$ is independently Me, Cl or F;
or a pharmaceutically acceptable salt thereof; and stereoisomers thereof.
3. A compound or a pharmaceutically acceptable salt according to claim 1 wherein the compound is according to formula IIa, IIb, IIc, or IId:
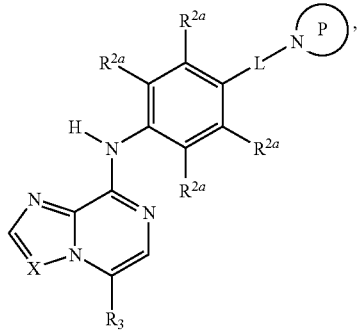
IIa
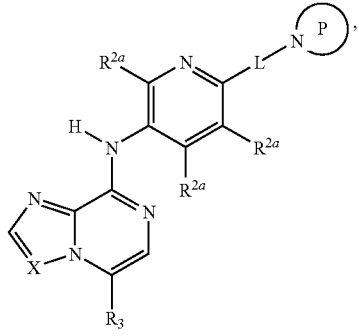
IIb
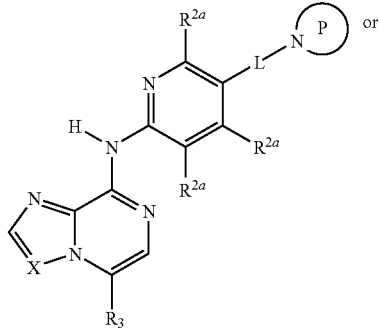
IIc IId

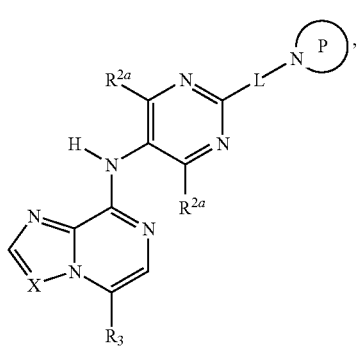

wherein L and the ring P are as in claim 1;
each $R^{2a}$ is H; and $R^3$ is as described in claim 1.

4. A compound or a pharmaceutically acceptable salt thereof according to claim 1, wherein $R^3$ is

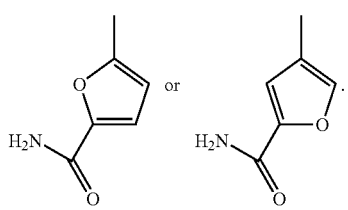

5. A compound or a pharmaceutically acceptable salt thereof according to claim 1, wherein the compound is according to formula Va, Vb, or Vc:

Va

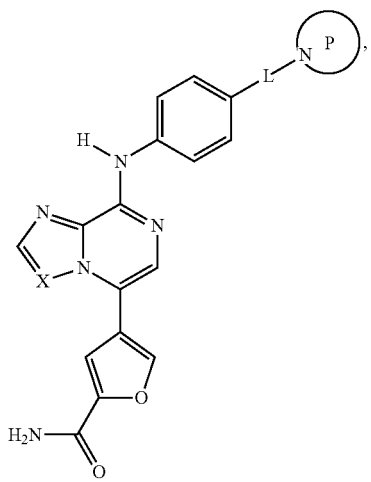

Vb

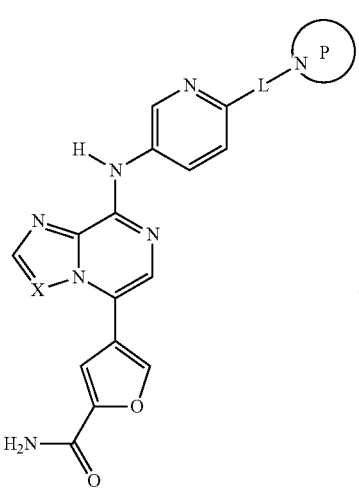

or

Vc

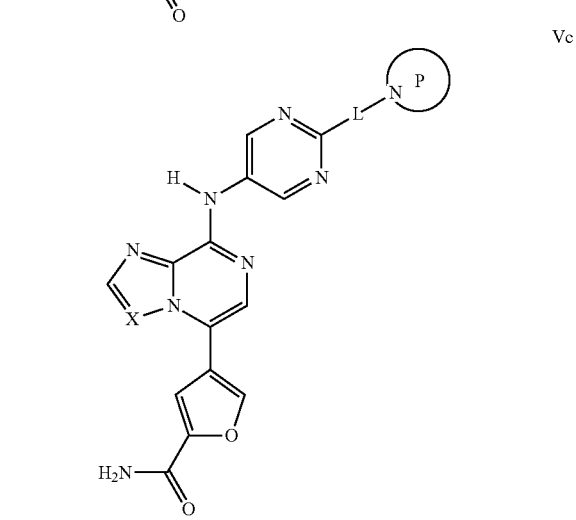

and X, L and the ring P are as in claim 1.

6. A compound or a pharmaceutically acceptable salt thereof according to claim 1, wherein L is a single bond; and the ring P is

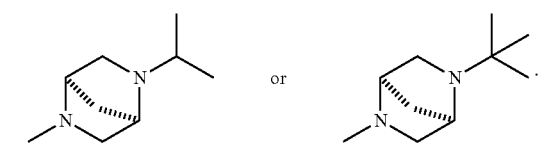

7. A compound or a pharmaceutically acceptable salt thereof according to claim 1, wherein L is a single bond; and the ring P is

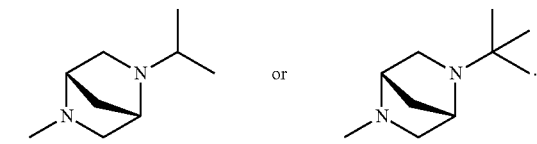

8. A compound or a pharmaceutically acceptable salt thereof according to claim 1, wherein the compound is selected from:

5-(8-(4-((1S,4S)-5-isopropyl-2,5-diazabicyclo[2.2.1]heptan-2-yl)phenylamino)-[1,2,4]triazolo[1,5-a]pyrazin-5-yl)isoindolin-1-one;

4-(8-(4-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide;

4-(8-(4-((1S,4R)-5-tert-butyl-2,5-diazabicyclo[2.2.1]heptan-2-yl)phenylamino)-[1,2,4]triazolo[1,5-a]pyrazin-5-yl)furan-2-carboxamide;

4-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-furan-2-carboxylic acid amide;

5-{8-(4-((1S,4S)-5-tert-butyl-2,5-diazabicyclo[2.2.1]heptan-2-yl)phenylamino)-[1,2,4]triazolo-[1,5-a]pyrazin-5-yl}-2,3-dihydro-isoindol-1-one; and 5-{8-(6-((1S,4S)-5-isopropyl-2,5-diazabicyclo[2.2.1]heptan-2-yl)pyridin-3-ylamino)-[1,2,4]triazolo[1,5-a]pyrazin-5-yl}-2,3-dihydro-isoindol-1-one;

and stereoisomers thereof.

9. A compound or a pharmaceutically acceptable salt thereof according to claim 2, wherein the compound is selected from:

4-(8-(3-((1S,4S)-5-isopropyl-2,5-diazabicyclo[2.2.1]heptan-2-yl)phenylamino)-[1,2,4]triazolo[1,5-a]pyrazin-5-yl)furan-2-carboxamide;

5-(8-(3-((1S,4S)-5-isopropyl-2,5-diazabicyclo[2.2.1]heptan-2-yl)phenylamino)-[1,2,4]triazolo[1,5-a]pyrazin-5-yl)isoindolin-1-one;

and stereoisomers thereof.

10. A compound or a pharmaceutically acceptable salt therof according to claim 1, wherein the compound is 4-(8-(4-((1S,4S)-5-isopropyl-2,5-diazabicyclo[2.2.1]heptan-2-yl)phenylamino-[1,2,4]triazolo[1,5-a]pyrazin-5-yl)furan-2-carboxamide.

11. A pharmaceutical composition comprising a pharmaceutically acceptable carrier and a pharmaceutically effective amount of a compound or a pharmaceutically acceptable salt thereof according to claim 1.

12. The pharmaceutical composition of claim 11, wherein the carrier is selected from a parenteral carrier, an oral carrier and a topical carrier.

* * * * *